(12) United States Patent
Bouchet et al.

(10) Patent No.: US 9,950,194 B2
(45) Date of Patent: Apr. 24, 2018

(54) PATIENT POSITIONING SYSTEM

(71) Applicant: Mevion Medical Systems, Inc., Littleton, MA (US)

(72) Inventors: Lionel G. Bouchet, Framingham, MA (US); Richard Bruce Rakes, Mount Juliet, TN (US)

(73) Assignee: Mevion Medical Systems, Inc., Littleton, MA (US)

( * ) Notice: Subject to any disclaimer, the term of this patent is extended or adjusted under 35 U.S.C. 154(b) by 18 days.

(21) Appl. No.: 14/481,609

(22) Filed: Sep. 9, 2014

(65) Prior Publication Data

US 2016/0067525 A1 Mar. 10, 2016

(51) Int. Cl.
*A61N 5/10* (2006.01)

(52) U.S. Cl.
CPC .......... *A61N 5/1049* (2013.01); *A61N 5/107* (2013.01); *A61N 5/1048* (2013.01); *A61N 5/1069* (2013.01); *A61N 2005/1052* (2013.01); *A61N 2005/1055* (2013.01); *A61N 2005/1059* (2013.01); *A61N 2005/1061* (2013.01); *A61N 2005/1087* (2013.01)

(58) Field of Classification Search
USPC ................................ 250/492.1; 600/407–427
See application file for complete search history.

(56) References Cited

U.S. PATENT DOCUMENTS

| | | | |
|---|---|---|---|
| 2,280,606 A | 4/1942 | Van et al. | |
| 2,492,324 A | 12/1949 | Salisbury | |
| 2,615,129 A | 10/1952 | McMillan | |
| 2,616,042 A | 10/1952 | Weeks | |
| 2,659,000 A | 11/1953 | Salisbury | |
| 2,701,304 A | 2/1955 | Dickinson | |
| 2,789,222 A | 4/1957 | Martin | |
| 3,175,131 A | 3/1965 | Burleigh et al. | |

(Continued)

FOREIGN PATENT DOCUMENTS

| | | |
|---|---|---|
| CA | 2629333 | 5/2007 |
| CN | 1377521 | 10/2002 |

(Continued)

OTHER PUBLICATIONS

Communication pursuant to Article 94(3) EPC for 15183802.6, 4 pages (dated May 18, 2016).

(Continued)

*Primary Examiner* — Phillip A Johnston
(74) *Attorney, Agent, or Firm* — Choate, Hall & Stewart LLP

(57) ABSTRACT

An example treatment system includes: a treatment couch for holding a patient; fiducials associated with the patient; an imaging system to capture an image of the fiducials and of an irradiation target while the patient is on the treatment couch, where the image is captured in a treatment room where treatment is to be performed; a mechanism to move the treatment couch; and a computer system programmed to align locations of the fiducials to the fiducials in the image, and to determine a location of the irradiation target relative to a treatment system based on locations of the fiducials and based on the image. The movement of the treatment couch into a treatment position in the treatment room may be based on the location of the irradiation target.

37 Claims, 20 Drawing Sheets

(56) References Cited

U.S. PATENT DOCUMENTS

| | | |
|---|---|---|
| 3,432,721 A | 3/1969 | Naydan et al. |
| 3,582,650 A | 6/1971 | Avery |
| 3,679,899 A | 7/1972 | Dimeff |
| 3,689,847 A | 9/1972 | Verster |
| 3,757,118 A | 9/1973 | Hodge et al. |
| 3,868,522 A | 2/1975 | Bigham et al. |
| 3,886,367 A | 5/1975 | Castle |
| 3,925,676 A | 12/1975 | Bigham et al. |
| 2,958,327 A | 5/1976 | Marancik et al. |
| 3,955,089 A | 5/1976 | McIntyre et al. |
| 3,958,327 A | 5/1976 | Marancik et al. |
| 3,992,625 A | 11/1976 | Schmidt et al. |
| 4,038,622 A | 7/1977 | Purcell |
| 4,047,068 A | 9/1977 | Ress et al. |
| 4,112,306 A | 9/1978 | Nunan |
| 4,129,784 A | 12/1978 | Tschunt et al. |
| 4,139,777 A | 2/1979 | Rautenbach |
| 4,197,510 A | 4/1980 | Szu |
| 4,220,866 A | 9/1980 | Symmons et al. |
| 4,230,129 A | 10/1980 | LeVeen |
| 4,256,966 A | 3/1981 | Heinz |
| 4,293,772 A | 10/1981 | Stieber |
| 4,336,505 A | 6/1982 | Meyer |
| 4,342,060 A | 7/1982 | Gibson |
| 4,345,210 A | 8/1982 | Tran |
| 4,353,033 A | 10/1982 | Karasawa |
| 4,425,506 A | 1/1984 | Brown et al. |
| 4,490,616 A | 12/1984 | Cipollina et al. |
| 4,507,614 A | 3/1985 | Prono et al. |
| 4,507,616 A | 3/1985 | Blosser et al. |
| 4,589,126 A | 5/1986 | Augustsson et al. |
| 4,598,208 A | 7/1986 | Brunelli et al. |
| 4,628,523 A | 12/1986 | Heflin |
| 4,633,125 A | 12/1986 | Blosser et al. |
| 4,641,057 A | 2/1987 | Blosser et al. |
| 4,641,104 A | 2/1987 | Blosser et al. |
| 4,651,007 A | 3/1987 | Perusek et al. |
| 4,680,565 A | 7/1987 | Jahnke |
| 4,705,955 A | 11/1987 | Mileikowsky |
| 4,710,722 A | 12/1987 | Jahnke |
| 4,726,046 A | 2/1988 | Nunan |
| 4,734,653 A | 3/1988 | Jahnke |
| 4,736,173 A | 4/1988 | Blosser et al. |
| 4,737,727 A | 4/1988 | Yamada et al. |
| 4,739,173 A | 4/1988 | Blosser et al. |
| 4,745,367 A | 5/1988 | Dustmann et al. |
| 4,754,147 A | 6/1988 | Maughan et al. |
| 4,763,483 A | 8/1988 | Olsen |
| 4,767,930 A | 8/1988 | Stieber et al. |
| 4,769,623 A | 9/1988 | Marsing et al. |
| 4,771,208 A | 9/1988 | Jongen et al. |
| 4,783,634 A | 11/1988 | Yamamoto et al. |
| 4,808,941 A | 2/1989 | Marsing |
| 4,812,658 A | 3/1989 | Koehler |
| 4,843,333 A | 6/1989 | Marsing et al. |
| 4,845,371 A | 7/1989 | Stieber |
| 4,865,284 A | 9/1989 | Gosis et al. |
| 4,868,843 A | 9/1989 | Nunan |
| 4,868,844 A | 9/1989 | Nunan |
| 4,870,287 A | 9/1989 | Cole et al. |
| 4,880,985 A | 11/1989 | Jones |
| 4,894,541 A | 1/1990 | Ono |
| 4,896,206 A | 1/1990 | Denham |
| 4,902,993 A | 2/1990 | Krevent |
| 4,904,949 A | 2/1990 | Wilson |
| 4,905,267 A | 2/1990 | Miller et al. |
| 4,917,344 A | 4/1990 | Prechter et al. |
| 4,943,781 A | 7/1990 | Wilson et al. |
| 4,945,478 A | 7/1990 | Merickel et al. |
| 4,968,915 A | 11/1990 | Wilson et al. |
| 4,987,309 A | 1/1991 | Klasen et al. |
| 4,992,744 A | 2/1991 | Fujita et al. |
| 4,996,496 A | 2/1991 | Kitamura et al. |
| 5,006,759 A | 4/1991 | Krispel |
| 5,010,562 A | 4/1991 | Hernandez et al. |
| 5,012,111 A | 4/1991 | Ueda |
| 5,017,789 A | 5/1991 | Young et al. |
| 5,017,882 A | 5/1991 | Finlan |
| 5,036,290 A | 7/1991 | Sonobe et al. |
| 5,039,057 A | 8/1991 | Prechter et al. |
| 5,039,867 A | 8/1991 | Nishihara et al. |
| 5,046,078 A | 9/1991 | Hernandez et al. |
| 5,072,123 A | 12/1991 | Johnsen |
| 5,111,042 A | 5/1992 | Sullivan et al. |
| 5,111,173 A | 5/1992 | Matsuda et al. |
| 5,117,194 A | 5/1992 | Nakanishi et al. |
| 5,117,212 A | 5/1992 | Yamamoto et al. |
| 5,117,829 A | 6/1992 | Miller et al. |
| 5,148,032 A | 9/1992 | Hernandez |
| 5,166,531 A | 11/1992 | Huntzinger |
| 5,189,687 A | 2/1993 | Bova et al. |
| 5,191,706 A | 3/1993 | Cosden |
| 5,240,218 A | 8/1993 | Dye |
| 5,260,579 A | 11/1993 | Yasuda et al. |
| 5,260,581 A | 11/1993 | Lesyna et al. |
| 5,278,533 A | 1/1994 | Kawaguchi |
| 5,285,166 A | 2/1994 | Hiramoto et al. |
| 5,317,164 A | 5/1994 | Kurokawa |
| 5,336,891 A | 8/1994 | Crewe |
| 5,341,104 A | 8/1994 | Anton et al. |
| 5,349,198 A | 9/1994 | Takanaka |
| 5,365,742 A | 11/1994 | Boffito et al. |
| 5,374,913 A | 12/1994 | Pissantezky et al. |
| 5,382,914 A | 1/1995 | Hamm et al. |
| 5,401,973 A | 3/1995 | McKeown et al. |
| 5,405,235 A | 4/1995 | Lebre et al. |
| 5,434,420 A | 7/1995 | McKeown et al. |
| 5,440,133 A | 8/1995 | Moyers et al. |
| 5,447,154 A | 9/1995 | Cinquin et al. |
| 5,451,794 A | 9/1995 | McKeown et al. |
| 5,461,773 A | 10/1995 | Kawaguchi |
| 5,463,291 A | 10/1995 | Carroll et al. |
| 5,464,411 A | 11/1995 | Schulte et al. |
| 5,492,922 A | 2/1996 | Palkowitz |
| 5,511,549 A | 4/1996 | Legg et al. |
| 5,521,469 A | 5/1996 | Laisne |
| 5,538,942 A | 7/1996 | Koyama et al. |
| 5,549,616 A | 8/1996 | Schulte et al. |
| 5,561,697 A | 10/1996 | Takafuji et al. |
| 5,585,642 A | 12/1996 | Britton et al. |
| 5,633,747 A | 5/1997 | Nikoonahad |
| 5,635,721 A | 6/1997 | Bardi et al. |
| 5,640,956 A | 6/1997 | Getzinger et al. |
| 5,668,371 A | 9/1997 | Deasy et al. |
| 5,672,878 A | 9/1997 | Yao |
| 5,690,107 A | 11/1997 | Hofmann |
| 5,691,679 A | 11/1997 | Ackermann et al. |
| 5,726,448 A | 3/1998 | Smith et al. |
| 5,727,554 A | 3/1998 | Kalend et al. |
| 5,730,745 A | 3/1998 | Schulte et al. |
| 5,737,506 A | 4/1998 | McKenna et al. |
| 5,751,781 A | 5/1998 | Brown et al. |
| 5,765,561 A | 6/1998 | Chen et al. |
| 5,776,050 A | 7/1998 | Chen et al. |
| 5,776,062 A | 7/1998 | Nields |
| 5,778,047 A | 7/1998 | Mansfield et al. |
| 5,783,914 A | 7/1998 | Hiramoto et al. |
| 5,784,431 A | 7/1998 | Kalend et al. |
| 5,797,924 A | 8/1998 | Schulte et al. |
| 5,800,355 A | 9/1998 | Hasegawa |
| 5,810,007 A | 9/1998 | Holupka et al. |
| 5,811,944 A | 9/1998 | Sampayan et al. |
| 5,818,058 A | 10/1998 | Nakanishi et al. |
| 5,820,552 A | 10/1998 | Crosby et al. |
| 5,821,705 A | 10/1998 | Caporasco et al. |
| 5,825,845 A | 10/1998 | Blair et al. |
| 5,825,908 A | 10/1998 | Pieper et al. |
| 5,833,627 A | 11/1998 | Shmulewitz et al. |
| 5,835,556 A | 11/1998 | Rogalla et al. |
| 5,841,237 A | 11/1998 | Alton |
| 5,846,043 A | 12/1998 | Spath |
| 5,851,180 A | 12/1998 | Crosby et al. |
| 5,851,182 A | 12/1998 | Sahadevan |
| 5,866,912 A | 2/1999 | Slater et al. |

(56) References Cited

U.S. PATENT DOCUMENTS

| | | |
|---|---|---|
| 5,871,445 A | 2/1999 | Bucholz |
| 5,874,811 A | 2/1999 | Finlan et al. |
| 5,891,034 A | 4/1999 | Bocholz |
| 5,895,926 A | 4/1999 | Britton et al. |
| 5,920,601 A | 7/1999 | Nigg et al. |
| 5,929,458 A | 7/1999 | Nemezawa et al. |
| 5,938,613 A | 8/1999 | Shmulewitz |
| 5,954,649 A | 9/1999 | Chia et al. |
| 5,957,844 A | 9/1999 | Dekel et al. |
| 5,963,615 A | 10/1999 | Egley et al. |
| 5,983,123 A | 11/1999 | Shmulewitz |
| 5,993,373 A | 11/1999 | Nonaka et al. |
| 5,999,840 A | 12/1999 | Grimson et al. |
| 6,008,499 A | 12/1999 | Hiramoto et al. |
| 6,016,439 A | 1/2000 | Acker |
| 6,019,724 A | 2/2000 | Gronningsaeter et al. |
| 6,021,343 A | 2/2000 | Foley et al. |
| 6,027,457 A | 2/2000 | Schmulewitz et al. |
| 6,032,066 A | 2/2000 | Lu et al. |
| 6,034,377 A | 3/2000 | Pu |
| 6,038,468 A | 3/2000 | Rex |
| 6,057,655 A | 5/2000 | Jongen |
| 6,061,426 A | 5/2000 | Linders et al. |
| 6,064,807 A | 5/2000 | Arai et al. |
| 6,066,851 A | 5/2000 | Madono et al. |
| 6,080,992 A | 6/2000 | Nonaka et al. |
| 6,087,670 A | 7/2000 | Hiramoto et al. |
| 6,094,760 A | 8/2000 | Nonaka et al. |
| 6,102,866 A | 8/2000 | Nields et al. |
| 6,118,845 A | 9/2000 | Simon et al. |
| 6,118,848 A | 9/2000 | Reiffel |
| 6,140,021 A | 10/2000 | Nakasuji et al. |
| 6,144,875 A | 11/2000 | Sachweikard et al. |
| 6,146,390 A | 11/2000 | Heilbrun et al. |
| 6,151,404 A | 11/2000 | Pieper |
| 6,158,708 A | 12/2000 | Egley et al. |
| 6,159,221 A | 12/2000 | Chakeres |
| 6,165,181 A | 12/2000 | Heilbrun et al. |
| 6,167,145 A | 12/2000 | Foley et al. |
| 6,193,657 B1 | 2/2001 | Drapkin |
| 6,207,952 B1 | 3/2001 | Kan et al. |
| 6,219,403 B1 | 4/2001 | Nishihara |
| 6,222,905 B1 | 4/2001 | Yoda et al. |
| 6,226,418 B1 | 5/2001 | Miller et al. |
| 6,226,548 B1 | 5/2001 | Foley et al. |
| 6,236,875 B1 | 5/2001 | Bucholz et al. |
| 6,241,657 B1 | 6/2001 | Chen et al. |
| 6,241,671 B1 | 6/2001 | Ritter et al. |
| 6,246,066 B1 | 6/2001 | Yuehu |
| 6,253,038 B1 | 6/2001 | Ito et al. |
| 6,256,591 B1 | 7/2001 | Yoda et al. |
| 6,261,299 B1 | 7/2001 | Chakeres |
| 6,265,837 B1 | 7/2001 | Akiyama et al. |
| 6,268,610 B1 | 7/2001 | Pu |
| 6,272,370 B1 | 8/2001 | Gillies et al. |
| 6,278,239 B1 | 8/2001 | Caporasco et al. |
| 6,279,579 B1 | 8/2001 | Riaziat et al. |
| 6,307,914 B1 | 10/2001 | Kunieda et al. |
| 6,316,776 B1 | 11/2001 | Hiramoto et al. |
| 6,325,758 B1 | 12/2001 | Carol et al. |
| 6,340,363 B1 | 1/2002 | Bolger et al. |
| 6,347,240 B1 | 2/2002 | Foley et al. |
| 6,348,058 B1 | 2/2002 | Melkent et al. |
| 6,366,021 B1 | 4/2002 | Meddaugh et al. |
| 6,369,585 B2 | 4/2002 | Yao |
| 6,370,224 B1 | 4/2002 | Simon et al. |
| 6,379,302 B1 | 4/2002 | Kessman et al. |
| 6,380,545 B1 | 4/2002 | Yan |
| 6,381,485 B1 | 4/2002 | Hunter et al. |
| 6,390,982 B1 | 5/2002 | Bova et al. |
| 6,402,762 B2 | 6/2002 | Hunter et al. |
| 6,406,482 B1 | 6/2002 | Chakeres |
| 6,407,505 B1 | 6/2002 | Bertsche |
| 6,408,107 B1 | 6/2002 | Miller et al. |
| 6,417,634 B1 | 7/2002 | Bergstrom |
| 6,433,336 B1 | 8/2002 | Jongen et al. |
| 6,433,349 B2 | 8/2002 | Akiyama et al. |
| 6,433,494 B1 | 8/2002 | Kulish et al. |
| 6,434,415 B1 | 8/2002 | Foley et al. |
| 6,441,569 B1 | 8/2002 | Janzow |
| 6,443,349 B1 | 9/2002 | Van Der Burg |
| 6,459,925 B1 | 10/2002 | Nields et al. |
| 6,463,317 B1 | 10/2002 | Kucharczyk et al. |
| 6,465,957 B1 | 10/2002 | Whitham et al. |
| 6,470,207 B1 | 10/2002 | Simon et al. |
| 6,472,834 B2 | 10/2002 | Hiramoto et al. |
| 6,476,403 B1 | 11/2002 | Dolinskii et al. |
| 6,477,400 B1 | 11/2002 | Barrick |
| 6,482,182 B1 | 11/2002 | Carroll et al. |
| 6,490,467 B1 | 12/2002 | Bucholz et al. |
| 6,491,699 B1 | 12/2002 | Henderson et al. |
| 6,491,702 B2 | 12/2002 | Heilbrun et al. |
| 6,492,922 B1 | 12/2002 | New |
| 6,493,424 B2 | 12/2002 | Whitham |
| 6,498,444 B1 | 12/2002 | Hanna et al. |
| 6,501,981 B1 | 12/2002 | Schweikard et al. |
| 6,519,316 B1 | 2/2003 | Collins |
| 6,533,794 B2 | 3/2003 | Chakeres |
| 6,549,802 B2 | 4/2003 | Thornton |
| 6,585,651 B2 | 7/2003 | Nolte et al. |
| 6,593,696 B2 | 7/2003 | Ding et al. |
| 6,594,336 B2 | 7/2003 | Nishizawa et al. |
| 6,600,164 B1 | 7/2003 | Badura et al. |
| 6,612,980 B2 | 9/2003 | Chen et al. |
| 6,617,598 B1 | 9/2003 | Matsuda |
| 6,621,889 B1 | 9/2003 | Mostafavi |
| 6,633,686 B1 | 10/2003 | Bakircioglu et al. |
| 6,639,234 B1 | 10/2003 | Badura et al. |
| 6,646,383 B2 | 11/2003 | Bertsche et al. |
| 6,669,635 B2 | 12/2003 | Kessman et al. |
| 6,670,618 B1 | 12/2003 | Hartmann et al. |
| 6,675,032 B2 | 1/2004 | Chen et al. |
| 6,683,318 B1 | 1/2004 | Haberer et al. |
| 6,683,426 B1 | 1/2004 | Kleeven |
| 6,690,960 B2 | 2/2004 | Chen et al. |
| 6,693,283 B2 | 2/2004 | Eickhoff et al. |
| 6,702,736 B2 | 3/2004 | Chen et al. |
| 6,710,362 B2 | 3/2004 | Kraft et al. |
| 6,713,773 B1 | 3/2004 | Lyons et al. |
| 6,713,976 B1 | 3/2004 | Zumoto et al. |
| 6,717,162 B1 | 4/2004 | Jongen |
| 6,736,831 B1 | 5/2004 | Hartmann et al. |
| 6,745,072 B1 | 6/2004 | Badura et al. |
| 6,769,806 B2 | 8/2004 | Moyers |
| 6,774,383 B2 | 8/2004 | Norimine et al. |
| 6,777,689 B2 | 8/2004 | Nelson |
| 6,777,700 B2 | 8/2004 | Yanagisawa et al. |
| 6,780,149 B1 | 8/2004 | Schulte |
| 6,796,943 B2 | 9/2004 | Mochizuki |
| 6,796,988 B2 | 9/2004 | Melkent et al. |
| 6,799,068 B1 | 9/2004 | Hartmann et al. |
| 6,800,866 B2 | 10/2004 | Amemiya et al. |
| 6,801,643 B2 | 10/2004 | Pieper |
| 6,803,591 B2 | 10/2004 | Muramatsu et al. |
| 6,814,694 B1 | 11/2004 | Pedroni |
| 6,822,244 B2 | 11/2004 | Beloussov et al. |
| 6,853,142 B2 | 2/2005 | Chistyakov |
| 6,853,703 B2 | 2/2005 | Svatos et al. |
| 6,864,770 B2 | 3/2005 | Nemoto et al. |
| 6,865,254 B2 | 3/2005 | Nafstadius |
| 6,872,213 B2 | 3/2005 | Chakeres |
| 6,873,123 B2 | 3/2005 | Marchand et al. |
| 6,891,177 B1 | 5/2005 | Kraft et al. |
| 6,891,924 B1 | 5/2005 | Yoda et al. |
| 6,892,090 B2 | 5/2005 | Verard et al. |
| 6,894,300 B2 | 5/2005 | Reimoser et al. |
| 6,897,451 B2 | 5/2005 | Kaercher et al. |
| 6,914,396 B1 | 7/2005 | Symons et al. |
| 6,920,347 B2 | 7/2005 | Simon et al. |
| 6,921,406 B1 | 7/2005 | Chakeres |
| 6,936,832 B2 | 8/2005 | Norimine et al. |
| 6,947,786 B2 | 9/2005 | Simon et al. |
| 6,953,943 B2 | 10/2005 | Yanagisawa et al. |
| 6,965,116 B1 | 11/2005 | Wagner et al. |

(56) References Cited

U.S. PATENT DOCUMENTS

| | | |
|---|---|---|
| 6,968,224 B2 | 11/2005 | Kessman et al. |
| 6,969,194 B1 | 11/2005 | Nafstadius |
| 6,978,166 B2 | 12/2005 | Foley et al. |
| 6,979,832 B2 | 12/2005 | Yanagisawa et al. |
| 6,984,835 B2 | 1/2006 | Harada |
| 6,990,368 B2 | 1/2006 | Simon et al. |
| 6,992,312 B2 | 1/2006 | Yanagisawa et al. |
| 6,993,112 B2 | 1/2006 | Hesse |
| 7,007,699 B2 | 3/2006 | Martinelli et al. |
| 7,008,105 B2 | 3/2006 | Amann et al. |
| 7,011,447 B2 | 3/2006 | Moyers |
| 7,012,267 B2 | 3/2006 | Moriyama et al. |
| 7,014,361 B1 | 3/2006 | Ein-Gal |
| 7,022,737 B2 | 4/2006 | Stamler et al. |
| 7,026,636 B2 | 4/2006 | Yanagisawa et al. |
| 7,038,403 B2 | 5/2006 | Mastrangeli et al. |
| 7,041,479 B2 | 5/2006 | Swartz et al. |
| 7,045,509 B2 | 5/2006 | Zerhusen |
| 7,045,781 B2 | 5/2006 | Adamec et al. |
| 7,046,830 B2 | 5/2006 | Gerard et al. |
| 7,048,716 B1 | 5/2006 | Kucharczyk et al. |
| 7,049,613 B2 | 5/2006 | Yanagisawa et al. |
| 7,053,389 B2 | 5/2006 | Yanagisawa et al. |
| 7,054,801 B2 | 5/2006 | Sakamoto et al. |
| RE39,133 E | 6/2006 | Clayton et al. |
| 7,060,870 B1 | 6/2006 | Stern et al. |
| 7,060,997 B2 | 6/2006 | Norimine et al. |
| 7,063,660 B2 | 6/2006 | Chen et al. |
| 7,071,479 B2 | 7/2006 | Yanagisawa et al. |
| 7,073,508 B2 | 7/2006 | Moyers |
| 7,081,619 B2 | 7/2006 | Bashkirov et al. |
| 7,084,410 B2 | 8/2006 | Beloussov et al. |
| 7,085,400 B1 | 8/2006 | Holsing et al. |
| 7,091,478 B2 | 8/2006 | Haberer |
| 7,094,587 B2 | 8/2006 | Meyers et al. |
| 7,098,463 B2 | 8/2006 | Adamovics |
| 7,102,144 B2 | 9/2006 | Matsuda et al. |
| 7,109,317 B1 | 9/2006 | Clemons et al. |
| 7,112,668 B2 | 9/2006 | Rastelli et al. |
| 7,122,811 B2 | 10/2006 | Matsuda et al. |
| 7,122,966 B2 | 10/2006 | Norling et al. |
| 7,122,978 B2 | 10/2006 | Nakanishi et al. |
| 7,125,663 B2 | 10/2006 | Schlegel et al. |
| 7,130,676 B2 | 10/2006 | Barrick |
| 7,135,678 B2 | 11/2006 | Wang et al. |
| 7,138,771 B2 | 11/2006 | Bechthold et al. |
| 7,141,421 B2 | 11/2006 | Adams et al. |
| 7,144,367 B2 | 12/2006 | Chen et al. |
| 7,145,336 B2 | 12/2006 | Brown |
| 7,149,333 B2 | 12/2006 | Pieper et al. |
| 7,154,107 B2 | 12/2006 | Yanagisawa et al. |
| 7,154,108 B2 | 12/2006 | Tadokoro et al. |
| 7,154,991 B2 | 12/2006 | Earnst et al. |
| 7,162,005 B2 | 1/2007 | Bjorkholm |
| 7,169,751 B2 | 1/2007 | Silos-Santiago et al. |
| 7,171,255 B2 | 1/2007 | Holupka et al. |
| 7,171,257 B2 | 1/2007 | Thomson |
| 7,173,264 B2 | 2/2007 | Moriyama et al. |
| 7,173,265 B2 | 2/2007 | Miller et al. |
| 7,173,385 B2 | 2/2007 | Caporaso et al. |
| 7,174,202 B2 | 2/2007 | Bladen et al. |
| 7,186,991 B2 | 3/2007 | Kato et al. |
| 7,187,800 B2 | 3/2007 | Hibbard |
| 7,193,227 B2 | 3/2007 | Hiramoto et al. |
| 7,197,170 B2 | 3/2007 | Dwyer et al. |
| 7,199,382 B2 | 4/2007 | Rigney et al. |
| 7,201,715 B2 | 4/2007 | Burdette et al. |
| 7,205,387 B2 | 4/2007 | Wang et al. |
| 7,208,748 B2 | 4/2007 | Sliski et al. |
| 7,212,608 B2 | 5/2007 | Nagamine et al. |
| 7,212,609 B2 | 5/2007 | Nagamine et al. |
| 7,217,276 B2 | 5/2007 | Henderson et al. |
| 7,221,733 B1 | 5/2007 | Takai et al. |
| 7,227,161 B2 | 6/2007 | Matsuda et al. |
| 7,229,626 B2 | 6/2007 | Donovan |
| 7,247,869 B2 | 7/2007 | Tadokoro et al. |
| 7,251,568 B2 | 7/2007 | Pittman et al. |
| 7,257,191 B2 | 8/2007 | Sommer |
| 7,258,971 B2 | 8/2007 | Karicheti et al. |
| 7,259,529 B2 | 8/2007 | Tanaka |
| 7,262,424 B2 | 8/2007 | Moriyama et al. |
| 7,262,565 B2 | 8/2007 | Fujisawa |
| 7,264,926 B2 | 9/2007 | Meyers |
| 7,268,358 B2 | 9/2007 | Ma et al. |
| 7,274,018 B2 | 9/2007 | Adamec et al. |
| 7,280,633 B2 | 10/2007 | Cheng et al. |
| 7,289,599 B2 | 10/2007 | Seppi et al. |
| 7,295,649 B2 | 11/2007 | Johnsen |
| 7,297,967 B2 | 11/2007 | Yanagisawa et al. |
| 7,301,016 B2 | 11/2007 | Meyers et al. |
| 7,301,162 B2 | 11/2007 | Matsuda et al. |
| 7,306,925 B2 | 12/2007 | Hallahan et al. |
| 7,307,264 B2 | 12/2007 | Brusasco et al. |
| 7,313,430 B2 | 12/2007 | Urquhart et al. |
| 7,317,192 B2 | 1/2008 | Ma |
| 7,318,805 B2 | 1/2008 | Schweikard et al. |
| 7,319,231 B2 | 1/2008 | Moriyama et al. |
| 7,319,336 B2 | 1/2008 | Bauer et al. |
| 7,331,713 B2 | 2/2008 | Moyers |
| 7,332,880 B2 | 2/2008 | Ina et al. |
| 7,345,291 B2 | 3/2008 | Kats |
| 7,345,292 B2 | 3/2008 | Moriyama et al. |
| 7,348,557 B2 | 3/2008 | Armit |
| 7,348,579 B2 | 3/2008 | Pedroni |
| 7,351,566 B2 | 4/2008 | Meyers et al. |
| 7,351,988 B2 | 4/2008 | Naumann et al. |
| 7,355,189 B2 | 4/2008 | Yanagisawa et al. |
| 7,357,934 B2 | 4/2008 | Donovan et al. |
| 7,366,562 B2 | 4/2008 | Dukesherer et al. |
| 7,368,740 B2 | 5/2008 | Beloussov et al. |
| 7,372,053 B2 | 5/2008 | Yamashita et al. |
| 7,378,672 B2 | 5/2008 | Harada |
| 7,381,979 B2 | 6/2008 | Yamashita et al. |
| 7,397,054 B2 | 7/2008 | Natori et al. |
| 7,397,901 B1 | 7/2008 | Johnsen |
| 7,398,309 B2 | 7/2008 | Baumann et al. |
| 7,402,392 B2 | 7/2008 | Hallahan et al. |
| 7,402,822 B2 | 7/2008 | Guertin et al. |
| 7,402,823 B2 | 7/2008 | Guertin et al. |
| 7,402,824 B2 | 7/2008 | Guertin et al. |
| 7,402,963 B2 | 7/2008 | Sliski |
| 7,405,407 B2 | 7/2008 | Hiramoto et al. |
| 7,411,054 B2 | 8/2008 | Meyers et al. |
| 7,425,717 B2 | 9/2008 | Matsuda et al. |
| 7,432,516 B2 | 10/2008 | Peggs et al. |
| 7,435,755 B2 | 10/2008 | Konopleva et al. |
| 7,438,685 B2 | 10/2008 | Burdette et al. |
| 7,439,528 B2 | 10/2008 | Nishiuchi et al. |
| 7,446,328 B2 | 11/2008 | Rigney et al. |
| 7,446,490 B2 | 11/2008 | Jongen et al. |
| 7,449,701 B2 | 11/2008 | Fujimaki et al. |
| 7,453,076 B2 | 11/2008 | Welch et al. |
| 7,465,944 B2 | 12/2008 | Ueno et al. |
| 7,466,085 B2 | 12/2008 | Nutt |
| 7,468,506 B2 | 12/2008 | Rogers et al. |
| 7,473,913 B2 | 1/2009 | Hermann et al. |
| 7,476,867 B2 | 1/2009 | Fritsch et al. |
| 7,476,883 B2 | 1/2009 | Nutt |
| 7,482,606 B2 | 1/2009 | Groezinger et al. |
| 7,485,308 B2 | 2/2009 | Meyers et al. |
| 7,488,598 B2 | 2/2009 | Ealick et al. |
| 7,492,556 B2 | 2/2009 | Atkins et al. |
| 7,496,398 B2 | 2/2009 | Nields et al. |
| 7,507,975 B2 | 3/2009 | Mohr |
| 7,525,104 B2 | 4/2009 | Harada |
| 7,531,818 B2 | 5/2009 | Brahme |
| 7,541,905 B2 | 6/2009 | Antaya |
| 7,542,791 B2 | 6/2009 | Mire et al. |
| 7,547,901 B2 | 6/2009 | Guertin et al. |
| 7,554,096 B2 | 6/2009 | Ward et al. |
| 7,554,097 B2 | 6/2009 | Ward et al. |
| 7,555,103 B2 | 6/2009 | Johnsen |
| RE40,852 E | 7/2009 | Martinelli et al. |
| 7,557,358 B2 | 7/2009 | Ward et al. |

(56) References Cited

U.S. PATENT DOCUMENTS

| | | |
|---|---|---|
| 7,557,359 B2 | 7/2009 | Ward et al. |
| 7,557,360 B2 | 7/2009 | Ward et al. |
| 7,557,361 B2 | 7/2009 | Ward et al. |
| 7,560,715 B2 | 7/2009 | Pedroni |
| 7,560,717 B2 | 7/2009 | Matsuda et al. |
| 7,567,694 B2 | 7/2009 | Lu et al. |
| 7,567,834 B2 | 7/2009 | Clayton et al. |
| 7,570,791 B2 | 8/2009 | Frank et al. |
| 7,574,251 B2 | 8/2009 | Lu et al. |
| 7,576,499 B2 | 8/2009 | Caporaso et al. |
| 7,579,603 B2 | 8/2009 | Birgy et al. |
| 7,579,610 B2 | 8/2009 | Grozinger et al. |
| 7,582,866 B2 | 9/2009 | Furuhashi et al. |
| 7,582,885 B2 | 9/2009 | Katagiri et al. |
| 7,582,886 B2 | 9/2009 | Trbojevic |
| 7,586,112 B2 | 9/2009 | Chiba et al. |
| 7,598,497 B2 | 10/2009 | Yamamoto et al. |
| 7,599,730 B2 | 10/2009 | Hunter et al. |
| 7,606,613 B2 | 10/2009 | Simon et al. |
| 7,609,009 B2 | 10/2009 | Tanaka et al. |
| 7,609,809 B2 | 10/2009 | Kapatoes et al. |
| 7,609,811 B1 | 10/2009 | Siljamaki et al. |
| 7,611,879 B2 | 11/2009 | Meyers et al. |
| 7,615,942 B2 | 11/2009 | Sanders et al. |
| 7,620,147 B2 | 11/2009 | Gertner et al. |
| 7,623,250 B2 | 11/2009 | Moctezuma de la Barrera et al. |
| RE41,066 E | 12/2009 | Martinelli et al. |
| 7,626,347 B2 | 12/2009 | Sliski |
| 7,629,598 B2 | 12/2009 | Harada |
| 7,630,753 B2 | 12/2009 | Simon et al. |
| 7,634,304 B2 | 12/2009 | Falco et al. |
| 7,635,722 B1 | 12/2009 | Bachynsky et al. |
| 7,636,595 B2 | 12/2009 | Marquart et al. |
| 7,639,853 B2 | 12/2009 | Olivera et al. |
| 7,639,854 B2 | 12/2009 | Schnarr et al. |
| 7,643,661 B2 | 1/2010 | Ruchala et al. |
| 7,646,898 B1 | 1/2010 | Nowinski et al. |
| 7,656,258 B1 | 2/2010 | Antaya et al. |
| 7,657,300 B2 | 2/2010 | Hunter et al. |
| 7,659,521 B2 | 2/2010 | Pedroni |
| 7,659,528 B2 | 2/2010 | Uematsu |
| 7,660,623 B2 | 2/2010 | Hunter et al. |
| 7,662,097 B2 | 2/2010 | Falco et al. |
| 7,666,849 B2 | 2/2010 | Steitz et al. |
| 7,668,291 B2 | 2/2010 | Nord et al. |
| 7,671,043 B2 | 3/2010 | Maguire |
| 7,672,429 B2 | 3/2010 | Urano et al. |
| 7,672,705 B2 | 3/2010 | Lachaine et al. |
| 7,679,073 B2 | 3/2010 | Urano et al. |
| 7,682,078 B2 | 3/2010 | Rietzel |
| 7,692,166 B2 | 4/2010 | Muraki et al. |
| 7,692,168 B2 | 4/2010 | Moriyama et al. |
| 7,693,260 B2 | 4/2010 | Gertner et al. |
| 7,695,192 B2 | 4/2010 | Henderson et al. |
| 7,696,316 B2 | 4/2010 | Kapeller-Libermann et al. |
| 7,696,499 B2 | 4/2010 | Miller et al. |
| 7,696,847 B2 | 4/2010 | Antaya |
| 7,697,972 B2 | 4/2010 | Verard et al. |
| 7,701,677 B2 | 4/2010 | Schultz et al. |
| 7,702,137 B2 | 4/2010 | Dwyer et al. |
| 7,709,818 B2 | 5/2010 | Matsuda et al. |
| 7,710,051 B2 | 5/2010 | Caporaso et al. |
| 7,718,982 B2 | 5/2010 | Sliski |
| 7,724,870 B2 | 5/2010 | Maltz et al. |
| 7,728,311 B2 | 6/2010 | Gall |
| 7,729,744 B2 | 6/2010 | Falco et al. |
| 7,732,182 B2 | 6/2010 | Meyers et al. |
| 7,732,194 B2 | 6/2010 | Pellenz et al. |
| 7,745,608 B2 | 6/2010 | Manoharan et al. |
| 7,746,978 B2 | 6/2010 | Cheng et al. |
| 7,751,865 B2 | 7/2010 | Jascob et al. |
| 7,755,305 B2 | 7/2010 | Umezawa et al. |
| 7,759,642 B2 | 7/2010 | Nir |
| 7,763,035 B2 | 7/2010 | Melkent et al. |
| 7,763,867 B2 | 7/2010 | Birgy et al. |
| 7,767,988 B2 | 8/2010 | Kaiser et al. |
| 7,770,231 B2 | 8/2010 | Prater et al. |
| 7,772,577 B2 | 8/2010 | Saito et al. |
| 7,773,723 B2 | 8/2010 | Nord et al. |
| 7,773,788 B2 | 8/2010 | Lu et al. |
| 7,776,055 B2 | 8/2010 | Kienzle, III |
| 7,778,488 B2 | 8/2010 | Nord et al. |
| 7,783,010 B2 | 8/2010 | Clayton |
| 7,784,127 B2 | 8/2010 | Kuro et al. |
| 7,786,451 B2 | 8/2010 | Ward et al. |
| 7,786,452 B2 | 8/2010 | Ward et al. |
| 7,789,560 B2 | 9/2010 | Moyers |
| 7,791,051 B2 | 9/2010 | Beloussov et al. |
| 7,795,305 B2 | 9/2010 | Konopleva et al. |
| 7,796,731 B2 | 9/2010 | Nord et al. |
| 7,797,032 B2 | 9/2010 | Martinelli et al. |
| 7,801,269 B2 | 9/2010 | Cravens et al. |
| 7,801,270 B2 | 9/2010 | Nord et al. |
| 7,801,271 B2 | 9/2010 | Gertner et al. |
| 7,801,585 B1 | 9/2010 | Weinstock |
| 7,801,988 B2 | 9/2010 | Baumann et al. |
| 7,807,982 B2 | 10/2010 | Nishiuchi et al. |
| 7,809,107 B2 | 10/2010 | Nord et al. |
| 7,811,587 B2 | 10/2010 | Donovan |
| 7,812,319 B2 | 10/2010 | Diehl et al. |
| 7,812,326 B2 | 10/2010 | Grozinger et al. |
| 7,816,657 B2 | 10/2010 | Hansmann et al. |
| 7,817,778 B2 | 10/2010 | Nord et al. |
| 7,817,836 B2 | 10/2010 | Chao et al. |
| 7,818,044 B2 | 10/2010 | Dukesherer et al. |
| 7,831,082 B2 | 11/2010 | Holsing et al. |
| 7,834,334 B2 | 11/2010 | Grozinger et al. |
| 7,834,336 B2 | 11/2010 | Boeh et al. |
| 7,835,492 B1 | 11/2010 | Sahadevan |
| 7,835,494 B2 | 11/2010 | Nord et al. |
| 7,835,502 B2 | 11/2010 | Spence et al. |
| 7,835,778 B2 | 11/2010 | Foley et al. |
| 7,835,784 B2 | 11/2010 | Mire et al. |
| 7,839,972 B2 | 11/2010 | Ruchala et al. |
| 7,839,973 B2 | 11/2010 | Nord et al. |
| 7,840,253 B2 | 11/2010 | Tremblay et al. |
| 7,846,737 B2 | 12/2010 | Schlegel |
| 7,848,488 B2 | 12/2010 | Mansfield |
| 7,853,305 B2 | 12/2010 | Simon et al. |
| 7,853,312 B2 | 12/2010 | Thornton |
| 7,853,313 B2 | 12/2010 | Thomson |
| 7,857,756 B2 | 12/2010 | Warren et al. |
| 7,860,216 B2 | 12/2010 | Jongen et al. |
| 7,860,550 B2 | 12/2010 | Saracen et al. |
| 7,863,415 B2 | 1/2011 | Gorin et al. |
| 7,867,729 B2 | 1/2011 | Meyers et al. |
| 7,868,301 B2 | 1/2011 | Diehl |
| 7,875,861 B2 | 1/2011 | Huttenberger et al. |
| 7,875,868 B2 | 1/2011 | Moriyama et al. |
| 7,879,989 B2 | 2/2011 | Meyers et al. |
| 7,881,431 B2 | 2/2011 | Aoi et al. |
| 7,881,770 B2 | 2/2011 | Melkent et al. |
| 7,889,906 B2 | 2/2011 | Smith et al. |
| 7,892,764 B2 | 2/2011 | Xiong et al. |
| 7,894,574 B1 | 2/2011 | Nord et al. |
| RE42,194 E | 3/2011 | Foley et al. |
| RE42,226 E | 3/2011 | Foley et al. |
| 7,897,147 B2 | 3/2011 | Dada |
| 7,906,102 B2 | 3/2011 | Hallahan et al. |
| 7,906,769 B2 | 3/2011 | Blasche et al. |
| 7,912,179 B2 | 3/2011 | Gertner et al. |
| 7,914,734 B2 | 3/2011 | Livingston |
| 7,919,765 B2 | 4/2011 | Timmer |
| 7,920,040 B2 | 4/2011 | Antaya et al. |
| 7,920,675 B2 | 4/2011 | Lomax et al. |
| 7,925,328 B2 | 4/2011 | Urquhart et al. |
| 7,928,415 B2 | 4/2011 | Bert et al. |
| 7,932,239 B2 | 4/2011 | Raines et al. |
| 7,933,640 B2 | 4/2011 | Kienzle, III |
| 7,934,869 B2 | 5/2011 | Ivanov et al. |
| 7,935,677 B2 | 5/2011 | Ljubimova et al. |
| 7,939,809 B2 | 5/2011 | Balakin |
| 7,940,881 B2 | 5/2011 | Jongen et al. |
| 7,940,894 B2 | 5/2011 | Balakin |

(56) References Cited

U.S. PATENT DOCUMENTS

| | | | |
|---|---|---|---|
| 7,943,913 B2 | 5/2011 | Balakin | |
| 7,947,652 B2 | 5/2011 | Lin et al. | |
| 7,947,969 B2 | 5/2011 | Pu | |
| 7,949,096 B2 | 5/2011 | Cheng et al. | |
| 7,949,386 B2 | 5/2011 | Buly et al. | |
| 7,950,587 B2 | 5/2011 | Henson et al. | |
| 7,953,203 B2 | 5/2011 | Gertner et al. | |
| 7,953,471 B2 | 5/2011 | Clayton et al. | |
| 7,957,508 B2 | 6/2011 | Brooks et al. | |
| 7,960,710 B2 | 6/2011 | Kruip et al. | |
| 7,961,844 B2 | 6/2011 | Takeda et al. | |
| 7,961,845 B2 | 6/2011 | Gertner et al. | |
| 7,966,075 B2 | 6/2011 | Johnson et al. | |
| 7,968,675 B2 | 6/2011 | Hallahan et al. | |
| 7,971,341 B2 | 7/2011 | Dukesherer et al. | |
| 7,973,145 B2 | 7/2011 | Ohta et al. | |
| 7,974,677 B2 | 7/2011 | Mire et al. | |
| 7,977,648 B2 | 7/2011 | Westerly et al. | |
| 7,977,656 B2 | 7/2011 | Fujimaki et al. | |
| 7,978,818 B2 | 7/2011 | Gertner et al. | |
| 7,978,819 B2 | 7/2011 | Gertner et al. | |
| 7,982,198 B2 | 7/2011 | Nishiuchi et al. | |
| 7,982,416 B2 | 7/2011 | Tanaka et al. | |
| 7,984,715 B2 | 7/2011 | Moyers | |
| 7,986,768 B2 | 7/2011 | Nord et al. | |
| 7,987,053 B2 | 7/2011 | Schaffner | |
| 7,989,785 B2 | 8/2011 | Emhofer et al. | |
| 7,990,524 B2 | 8/2011 | Jureller et al. | |
| 7,996,064 B2 | 8/2011 | Simon et al. | |
| 7,997,553 B2 | 8/2011 | Sloan et al. | |
| 7,998,062 B2 | 8/2011 | Gilboa | |
| 7,998,460 B2 | 8/2011 | Monje et al. | |
| 8,000,442 B2 | 8/2011 | Lachaine et al. | |
| 8,002,465 B2 | 8/2011 | Ahn | |
| 8,002,466 B2 | 8/2011 | Von Neubeck et al. | |
| 8,003,964 B2 | 8/2011 | Stark et al. | |
| 8,009,803 B2 | 8/2011 | Nord et al. | |
| 8,009,804 B2 | 8/2011 | Siljamaki et al. | |
| 8,012,945 B2 | 9/2011 | Hallahan et al. | |
| 8,026,218 B2 | 9/2011 | Hruby et al. | |
| 8,034,791 B2 | 10/2011 | Weichselbaum et al. | |
| 8,039,822 B2 | 10/2011 | Rietzel | |
| 8,041,006 B2 | 10/2011 | Boyden et al. | |
| 8,044,364 B2 | 10/2011 | Yamamoto | |
| 8,045,679 B2 | 10/2011 | Balakin | |
| 8,046,052 B2 | 10/2011 | Verard et al. | |
| 8,046,053 B2 | 10/2011 | Foley et al. | |
| 8,048,872 B2 | 11/2011 | Curd et al. | |
| 8,049,176 B1 | 11/2011 | Majewski et al. | |
| 8,049,187 B2 | 11/2011 | Tachikawa | |
| 8,053,508 B2 | 11/2011 | Korkut et al. | |
| 8,053,739 B2 | 11/2011 | Rietzel | |
| 8,053,745 B2 | 11/2011 | Moore | |
| 8,053,746 B2 | 11/2011 | Timmer et al. | |
| 8,057,407 B2 | 11/2011 | Martinelli et al. | |
| 8,060,185 B2 | 11/2011 | Hunter et al. | |
| 8,062,892 B2 | 11/2011 | Schlegel et al. | |
| 8,064,988 B2 | 11/2011 | Weinstock | |
| 8,067,748 B2 | 11/2011 | Balakin | |
| 8,069,675 B2 | 12/2011 | Radovinsky et al. | |
| 8,071,315 B2 | 12/2011 | Reed et al. | |
| 8,071,562 B2 | 12/2011 | Bader et al. | |
| 8,071,732 B2 | 12/2011 | Gaiger et al. | |
| 8,071,966 B2 | 12/2011 | Kaiser et al. | |
| 8,074,662 B2 | 12/2011 | Hunter et al. | |
| 8,080,801 B2 | 12/2011 | Safai | |
| 8,085,899 B2 | 12/2011 | Nord et al. | |
| 8,086,299 B2 | 12/2011 | Adler et al. | |
| 8,089,054 B2 | 1/2012 | Balakin | |
| 8,093,425 B2 | 1/2012 | Koya et al. | |
| 8,093,564 B2 | 1/2012 | Balakin | |
| 8,093,568 B2 | 1/2012 | Mackie et al. | |
| 8,100,132 B2 | 1/2012 | Markstroem | |
| 8,101,157 B2 | 1/2012 | Hallahn | |
| 8,105,339 B2 | 1/2012 | Melkent et al. | |
| 8,111,125 B2 | 2/2012 | Antaya et al. | |
| 8,112,292 B2 | 2/2012 | Simon | |
| 8,123,697 B2 | 2/2012 | Daum et al. | |
| 8,129,699 B2 | 3/2012 | Balakin | |
| 8,135,198 B2 | 3/2012 | Lachaine et al. | |
| 8,135,201 B2 | 3/2012 | Smith et al. | |
| 8,144,832 B2 | 3/2012 | Balakin | |
| RE43,328 E | 4/2012 | Foley et al. | |
| 8,153,989 B2 | 4/2012 | Tachikawa et al. | |
| 8,160,205 B2 | 4/2012 | Saracen et al. | |
| 8,164,074 B2 | 4/2012 | Boyden et al. | |
| 8,165,658 B2 | 4/2012 | Waynik et al. | |
| 8,168,958 B2 | 5/2012 | Boyden et al. | |
| 8,171,580 B2 * | 5/2012 | Wilson | A61G 7/103 |
| | | | 5/81.1 HS |
| 8,173,429 B2 | 5/2012 | Pellenz et al. | |
| 8,173,981 B2 | 5/2012 | Trbojevic | |
| 8,173,983 B1 | 5/2012 | Sahadevan | |
| 8,175,681 B2 | 5/2012 | Hartmann et al. | |
| 8,178,859 B2 | 5/2012 | Balakin | |
| 8,184,772 B2 | 5/2012 | Gertner et al. | |
| 8,188,688 B2 | 5/2012 | Balakin | |
| 8,189,738 B2 | 5/2012 | Dussault et al. | |
| 8,189,889 B2 | 5/2012 | Pearlstein et al. | |
| 8,193,182 B2 | 6/2012 | Ren et al. | |
| 8,198,607 B2 | 6/2012 | Balakin | |
| 8,200,314 B2 | 6/2012 | Bladen et al. | |
| 8,221,480 B2 | 7/2012 | Boyden et al. | |
| 8,222,613 B2 | 7/2012 | Tajiri et al. | |
| 8,227,204 B2 | 7/2012 | Boyden et al. | |
| 8,227,768 B2 | 7/2012 | Smick et al. | |
| 8,229,069 B2 | 7/2012 | Gertner et al. | |
| 8,229,072 B2 | 7/2012 | Balakin | |
| 8,229,073 B2 | 7/2012 | Gertner et al. | |
| 8,232,536 B2 | 7/2012 | Harada | |
| 8,238,517 B2 | 8/2012 | Gertner et al. | |
| 8,239,001 B2 | 8/2012 | Verard et al. | |
| 8,249,317 B2 | 8/2012 | Falco et al. | |
| 8,254,521 B2 | 8/2012 | Brooks et al. | |
| 8,256,233 B2 | 9/2012 | Boyden | |
| 8,258,305 B2 | 9/2012 | Hauske | |
| 8,263,823 B2 | 9/2012 | Fu | |
| 8,269,198 B2 | 9/2012 | Dilmanian et al. | |
| 8,271,069 B2 | 9/2012 | Jascob et al. | |
| 8,272,384 B2 | 9/2012 | Wiberg et al. | |
| 8,273,743 B2 | 9/2012 | Koehler et al. | |
| 8,273,869 B2 | 9/2012 | Fitzgerald et al. | |
| RE43,750 E | 10/2012 | Martinelli et al. | |
| 8,278,278 B2 | 10/2012 | Malkas et al. | |
| 8,283,384 B2 | 10/2012 | Stewart et al. | |
| 8,288,742 B2 | 10/2012 | Balakin | |
| 8,290,572 B2 | 10/2012 | Martinelli et al. | |
| 8,291,717 B2 | 10/2012 | Radovinsky et al. | |
| 8,294,127 B2 | 10/2012 | Tachibana | |
| 8,295,435 B2 | 10/2012 | Wang et al. | |
| 8,295,437 B2 | 10/2012 | Gertner et al. | |
| 8,304,725 B2 | 11/2012 | Komuro et al. | |
| 8,304,750 B2 | 11/2012 | Preikszas et al. | |
| 8,306,186 B2 | 11/2012 | Gertner et al. | |
| 8,309,941 B2 | 11/2012 | Balakin | |
| 8,320,653 B2 | 11/2012 | Holsing et al. | |
| 8,326,398 B2 | 12/2012 | Weinstock | |
| 8,330,132 B2 | 12/2012 | Guertin et al. | |
| 8,331,531 B2 | 12/2012 | Fahrig et al. | |
| 8,334,520 B2 | 12/2012 | Otaka et al. | |
| 8,335,397 B2 | 12/2012 | Takane et al. | |
| RE43,952 E | 1/2013 | Uhl et al. | |
| 8,344,028 B2 | 1/2013 | Xu et al. | |
| 8,344,340 B2 | 1/2013 | Gall | |
| 8,348,846 B2 | 1/2013 | Gunther et al. | |
| 8,350,214 B2 | 1/2013 | Otaki et al. | |
| 8,359,730 B2 | 1/2013 | Burg et al. | |
| 8,364,242 B2 | 1/2013 | Li | |
| 8,344,125 B2 | 2/2013 | Manoharan et al. | |
| 8,366,618 B2 | 2/2013 | Falco et al. | |
| 8,368,038 B2 | 2/2013 | Balakin | |
| 8,368,043 B2 | 2/2013 | Havelange et al. | |
| 8,369,592 B2 | 2/2013 | Leroy et al. | |
| 8,372,816 B2 | 2/2013 | Brown | |

(56) References Cited

U.S. PATENT DOCUMENTS

| | | |
|---|---|---|
| 8,373,143 B2 | 2/2013 | Balakin |
| 8,373,145 B2 | 2/2013 | Balakin |
| 8,378,299 B2 | 2/2013 | Frosien |
| 8,378,311 B2 | 2/2013 | Balakin |
| 8,378,321 B2 | 2/2013 | Balakin |
| 8,382,943 B2 | 2/2013 | Clark |
| 8,383,671 B1 | 2/2013 | Consigny |
| 8,384,053 B2 | 2/2013 | Balakin |
| 8,395,131 B2 | 2/2013 | Wu et al. |
| 8,388,932 B2 | 3/2013 | Hallahan et al. |
| 8,389,949 B2 | 3/2013 | Harada et al. |
| 8,393,821 B2 | 3/2013 | Wiberg et al. |
| 8,399,866 B2 | 3/2013 | Balakin |
| 8,401,148 B2 | 3/2013 | Lu et al. |
| 8,401,616 B2 | 3/2013 | Verard et al. |
| 8,405,042 B2 | 3/2013 | Honda et al. |
| 8,405,056 B2 | 3/2013 | Amaldi et al. |
| 8,410,075 B2 | 4/2013 | Keana et al. |
| 8,415,643 B2 | 4/2013 | Balakin |
| 8,416,918 B2 | 4/2013 | Nord et al. |
| 8,421,041 B2 | 4/2013 | Balakin |
| 8,426,833 B2 | 4/2013 | Trbojevic |
| 8,428,690 B2 | 4/2013 | Li et al. |
| 8,436,323 B2 | 5/2013 | Iseki et al. |
| 8,436,327 B2 | 5/2013 | Balakin |
| 8,440,987 B2 | 5/2013 | Stephani et al. |
| 8,442,185 B2 | 5/2013 | Gertner et al. |
| 8,444,564 B2 | 5/2013 | Mahfouz et al. |
| 8,445,872 B2 | 5/2013 | Behrens et al. |
| 8,447,403 B2 | 5/2013 | Sharma et al. |
| 8,447,404 B2 | 5/2013 | Sharma et al. |
| 8,447,414 B2 | 5/2013 | Johnson et al. |
| 8,452,068 B2 | 5/2013 | Averbuch et al. |
| RE44,305 E | 6/2013 | Foley et al. |
| 8,455,686 B2 | 6/2013 | Koya et al. |
| 8,457,277 B2 | 6/2013 | Gertner et al. |
| 8,457,760 B2 | 6/2013 | Johnson et al. |
| 8,461,199 B2 | 6/2013 | Masazumi et al. |
| 8,461,328 B2 | 6/2013 | Babu et al. |
| 8,466,441 B2 | 6/2013 | Iwata et al. |
| 8,467,497 B2 | 6/2013 | Lu et al. |
| 8,467,589 B2 | 6/2013 | Averbuch et al. |
| 8,467,851 B2 | 6/2013 | Mire et al. |
| 8,467,853 B2 | 6/2013 | Hunter et al. |
| 8,472,583 B2 | 6/2013 | Star-Lack et al. |
| 8,473,026 B2 | 6/2013 | Ferre et al. |
| 8,473,032 B2 | 6/2013 | Averbuch |
| 8,470,990 B2 | 7/2013 | Steitz et al. |
| 8,481,001 B2 | 7/2013 | Lamb et al. |
| 8,481,498 B1 | 7/2013 | Hoffman |
| 8,481,739 B2 | 7/2013 | Muthuppalaniappan et al. |
| 8,482,606 B2 | 7/2013 | Razzaque et al. |
| 8,483,357 B2 | 7/2013 | Siljamaki et al. |
| 8,485,861 B2 | 7/2013 | Boyden et al. |
| 8,487,278 B2 | 7/2013 | Balakin |
| 8,492,379 B2 | 7/2013 | Kassion et al. |
| 8,494,116 B2 | 7/2013 | Gertner et al. |
| 8,494,613 B2 | 7/2013 | Markowitz et al. |
| 8,494,614 B2 | 7/2013 | Markowitz et al. |
| 8,497,272 B2 | 7/2013 | Sun et al. |
| 8,507,661 B2 | 8/2013 | Manoharan et al. |
| 8,509,383 B2 | 8/2013 | Lu et al. |
| 8,509,913 B2 | 8/2013 | Johnson et al. |
| 8,513,266 B2 | 8/2013 | Lamb et al. |
| 8,518,031 B2 | 8/2013 | Boyden et al. |
| 8,519,365 B2 | 8/2013 | Balakin |
| 8,414,356 B2 | 9/2013 | Boyden et al. |
| 8,527,032 B2 | 9/2013 | Li |
| 8,529,426 B2 | 9/2013 | Boyden et al. |
| 8,536,547 B2 | 9/2013 | Maurer et al. |
| 8,545,806 B2 | 10/2013 | Boyden et al. |
| 8,545,856 B2 | 10/2013 | Boyden et al. |
| 8,545,857 B2 | 10/2013 | Boyden et al. |
| 8,546,322 B2 | 10/2013 | Gorin et al. |
| 8,548,565 B2 | 10/2013 | Hunter et al. |
| 8,549,732 B2 | 10/2013 | Burg et al. |
| 8,551,506 B2 | 10/2013 | Boyden et al. |
| 8,552,406 B2 | 10/2013 | Phaneuf et al. |
| 8,552,408 B2 | 10/2013 | Hanawa et al. |
| 8,554,307 B2 | 10/2013 | Razzaque et al. |
| 8,562,964 B2 | 10/2013 | Ljubimova et al. |
| 8,563,012 B2 | 10/2013 | Boyden et al. |
| 8,567,405 B2 | 10/2013 | Arn et al. |
| 8,568,363 B2 | 10/2013 | Boyden et al. |
| 8,569,323 B2 | 10/2013 | Ren et al. |
| 8,569,717 B2 | 10/2013 | Balakin |
| 8,581,004 B2 | 11/2013 | Kowalczyk-Przewloka et al. |
| 8,581,215 B2 | 11/2013 | Balakin |
| 8,581,525 B2 | 11/2013 | Antaya et al. |
| 8,585,598 B2 | 11/2013 | Razzaque et al. |
| 8,586,366 B2 | 11/2013 | Hiroki et al. |
| 8,586,727 B2 | 12/2013 | Fitzgerald et al. |
| 8,598,139 B2 | 12/2013 | Fitzgerald et al. |
| 8,603,494 B2 | 12/2013 | Boyden et al. |
| 8,603,495 B2 | 12/2013 | Boyden et al. |
| 8,603,496 B2 | 12/2013 | Boyden et al. |
| 8,604,032 B2 | 12/2013 | Ren et al. |
| 8,607,385 B2 | 12/2013 | Isham |
| 8,609,720 B2 | 12/2013 | Chen et al. |
| 8,611,984 B2 | 12/2013 | Greenburg et al. |
| 8,613,694 B2 | 12/2013 | Walsh |
| 8,613,937 B2 | 12/2013 | Boyden et al. |
| 8,614,554 B2 | 12/2013 | Balakin |
| 8,617,521 B2 | 12/2013 | Hallahan et al. |
| 8,618,521 B2 | 12/2013 | Loo et al. |
| 8,625,739 B2 | 1/2014 | Balakin |
| 8,627,822 B2 | 1/2014 | Balakin |
| 8,634,897 B2 | 1/2014 | Simon et al. |
| 8,634,898 B2 | 1/2014 | Adler et al. |
| 8,637,818 B2 | 1/2014 | Balakin |
| 8,637,833 B2 | 1/2014 | Balakin |
| 8,641,621 B2 | 2/2014 | Razzaque et al. |
| 8,642,607 B2 | 2/2014 | Muthuppalaniappan et al. |
| 8,644,907 B2 | 2/2014 | Hartmann et al. |
| 8,644,910 B2 | 2/2014 | Rousso et al. |
| 8,653,314 B2 | 2/2014 | Pelati et al. |
| 8,653,473 B2 | 2/2014 | Yajima |
| 9,108,048 B2 * | 8/2015 | Maurer, Jr. .......... A61B 6/5247 |
| 2002/0172317 A1 | 11/2002 | Maksimchuk et al. |
| 2003/0048080 A1 | 3/2003 | Amemiya et al. |
| 2003/0125622 A1 | 7/2003 | Schweikard et al. |
| 2003/0136924 A1 | 7/2003 | Kraft et al. |
| 2003/0152197 A1 | 8/2003 | Moyers |
| 2003/0163015 A1 | 8/2003 | Yanagisawa et al. |
| 2003/0183779 A1 | 10/2003 | Norimine et al. |
| 2003/0206614 A1 | 11/2003 | Kendrick et al. |
| 2003/0234369 A1 | 12/2003 | Glukhoy |
| 2004/0000650 A1 | 1/2004 | Yanagisawa et al. |
| 2004/0017888 A1 | 1/2004 | Seppi et al. |
| 2004/0056212 A1 | 3/2004 | Yanagisawa et al. |
| 2004/0061077 A1 | 4/2004 | Muramatsu et al. |
| 2004/0061078 A1 | 4/2004 | Muramatsu et al. |
| 2004/0085023 A1 | 5/2004 | Chistyakov |
| 2004/0098445 A1 | 5/2004 | Baumann et al. |
| 2004/0111134 A1 | 6/2004 | Muramatsu et al. |
| 2004/0118081 A1 | 6/2004 | Reimoser et al. |
| 2004/0149934 A1 | 8/2004 | Yanagisawa et al. |
| 2004/0159795 A1 | 8/2004 | Kaercher et al. |
| 2004/0173763 A1 | 9/2004 | Moriyama et al. |
| 2004/0174958 A1 | 9/2004 | Moriyama et al. |
| 2004/0183033 A1 | 9/2004 | Moriyama et al. |
| 2004/0183035 A1 | 9/2004 | Yanagisawa et al. |
| 2004/0200982 A1 | 10/2004 | Moriyama et al. |
| 2004/0200983 A1 | 10/2004 | Fujimaki et al. |
| 2004/0213381 A1 | 10/2004 | Harada |
| 2004/0227104 A1 | 11/2004 | Matsuda et al. |
| 2004/0232356 A1 | 11/2004 | Norimine et al. |
| 2004/0240626 A1 | 12/2004 | Moyers |
| 2005/0058245 A1 | 3/2005 | Ein-Gal |
| 2005/0089141 A1 | 4/2005 | Brown |
| 2005/0161618 A1 | 7/2005 | Pedroni |
| 2005/0184686 A1 | 8/2005 | Caporaso et al. |
| 2005/0228255 A1 | 10/2005 | Saracen et al. |
| 2005/0234327 A1 | 10/2005 | Saracen et al. |

(56) References Cited

U.S. PATENT DOCUMENTS

| | | |
|---|---|---|
| 2005/0247890 A1 | 11/2005 | Norimine et al. |
| 2006/0017015 A1 | 1/2006 | Sliski et al. |
| 2006/0067468 A1 | 3/2006 | Rietzel |
| 2006/0126792 A1 | 6/2006 | Li |
| 2006/0145088 A1 | 7/2006 | Ma |
| 2006/0175991 A1 | 8/2006 | Fujisawa |
| 2006/0284562 A1 | 12/2006 | Hruby et al. |
| 2007/0001128 A1 | 1/2007 | Sliski et al. |
| 2007/0013273 A1 | 1/2007 | Albert et al. |
| 2007/0014654 A1 | 1/2007 | Haverfield et al. |
| 2007/0023699 A1 | 2/2007 | Yamashita et al. |
| 2007/0029510 A1 | 2/2007 | Hermann et al. |
| 2007/0051904 A1 | 3/2007 | Kaiser et al. |
| 2007/0092812 A1 | 4/2007 | Caporasco et al. |
| 2007/0114945 A1 | 5/2007 | Mattaboni et al. |
| 2007/0145916 A1 | 6/2007 | Caporasco et al. |
| 2007/0171015 A1 | 7/2007 | Antaya |
| 2007/0181519 A1 | 8/2007 | Khoshnevis |
| 2007/0284548 A1 | 12/2007 | Kaiser et al. |
| 2008/0093567 A1 | 4/2008 | Gall |
| 2008/0218102 A1 | 9/2008 | Sliski |
| 2009/0096179 A1 | 4/2009 | Stark et al. |
| 2009/0140671 A1 | 6/2009 | O'Neal et al. |
| 2009/0140672 A1 | 6/2009 | Gall et al. |
| 2009/0200483 A1 | 8/2009 | Gall et al. |
| 2010/0045213 A1 | 2/2010 | Sliski et al. |
| 2010/0230617 A1 | 9/2010 | Gall |
| 2010/0308235 A1 | 12/2010 | Sliski |
| 2011/0285327 A1 | 11/2011 | Begg et al. |
| 2011/0299919 A1 | 12/2011 | Stark |
| 2013/0053616 A1 | 2/2013 | Gall |
| 2013/0127375 A1 | 5/2013 | Sliski |
| 2013/0131424 A1 | 5/2013 | Sliski |
| 2013/0237425 A1 | 9/2013 | Leigh et al. |
| 2014/0028220 A1 | 1/2014 | Bromberg et al. |
| 2014/0042934 A1 | 2/2014 | Hiroshi |
| 2014/0097920 A1 | 4/2014 | Goldie et al. |

FOREIGN PATENT DOCUMENTS

| | | |
|---|---|---|
| CN | 1537657 A | 10/2004 |
| CN | 1816243 A | 8/2006 |
| CN | 101932361 | 12/2010 |
| CN | 101933405 | 12/2010 |
| CN | 101933406 | 12/2010 |
| CN | 101061759 | 5/2011 |
| DE | 2753397 | 6/1978 |
| DE | 31 48 100 | 6/1983 |
| DE | 35 30 446 | 8/1984 |
| DE | 41 01 094 C1 | 5/1992 |
| DE | 4411171 | 10/1995 |
| EP | 0 194 728 | 9/1986 |
| EP | 0 277 521 | 8/1988 |
| EP | 0 208 163 | 1/1989 |
| EP | 0 222 786 | 7/1990 |
| EP | 0 221 987 | 1/1991 |
| EP | 0 499 253 | 8/1992 |
| EP | 0 306 966 | 4/1995 |
| EP | 0 388 123 | 5/1995 |
| EP | 0 465 597 | 5/1997 |
| EP | 0 911 064 | 6/1998 |
| EP | 0 864 337 | 9/1998 |
| EP | 0 776 595 | 12/1998 |
| EP | 1 069 809 | 1/2001 |
| EP | 1 153 398 | 4/2001 |
| EP | 1 294 445 | 3/2003 |
| EP | 1 348 465 | 10/2003 |
| EP | 1 358 908 | 11/2003 |
| EP | 1 371 390 | 12/2003 |
| EP | 1 402 923 | 3/2004 |
| EP | 1 430 932 | 6/2004 |
| EP | 1 454 653 | 9/2004 |
| EP | 1 454 654 | 9/2004 |
| EP | 1 454 655 | 9/2004 |
| EP | 1 454 656 | 9/2004 |
| EP | 1 454 657 | 9/2004 |
| EP | 1 477 206 | 11/2004 |
| EP | 1 738 798 | 1/2007 |
| EP | 1 826 778 | 8/2007 |
| EP | 1 949 404 | 7/2008 |
| EP | 2183753 | 7/2008 |
| EP | 2394498 | 2/2010 |
| EP | 2232961 | 9/2010 |
| EP | 2232962 | 9/2010 |
| EP | 2227295 | 5/2011 |
| EP | 1 605 742 | 6/2011 |
| EP | 2363170 | 9/2011 |
| EP | 2363171 | 9/2011 |
| EP | 2995348 | 3/2016 |
| FR | 2 560 421 | 8/1985 |
| FR | 2911843 | 8/2008 |
| GB | 0 957 342 | 5/1964 |
| GB | 2 015 821 | 9/1979 |
| GB | 2 361 523 | 10/2001 |
| JP | 43-23267 | 10/1968 |
| JP | U48-108098 | 12/1973 |
| JP | 57-162527 | 10/1982 |
| JP | 58-141000 | 8/1983 |
| JP | 61-80800 | 4/1986 |
| JP | 61-225798 | 10/1986 |
| JP | 62-150804 | 7/1987 |
| JP | 62-186500 | 8/1987 |
| JP | 10-071213 | 3/1988 |
| JP | 63-149344 | 6/1988 |
| JP | 63-218200 | 9/1988 |
| JP | 63-226899 | 9/1988 |
| JP | 64-89621 | 4/1989 |
| JP | 01-276797 | 11/1989 |
| JP | 01-302700 | 12/1989 |
| JP | 4-94198 | 3/1992 |
| JP | 04-128717 | 4/1992 |
| JP | 04-129768 | 4/1992 |
| JP | 04-273409 | 9/1992 |
| JP | 04-337300 | 11/1992 |
| JP | 05-341352 | 12/1993 |
| JP | 06-233831 | 8/1994 |
| JP | 06-036893 | 10/1994 |
| JP | 07-260939 | 10/1995 |
| JP | 07-263196 | 10/1995 |
| JP | 08-173890 | 7/1996 |
| JP | 08-264298 | 10/1996 |
| JP | 09-162585 | 6/1997 |
| JP | 11-47287 | 2/1999 |
| JP | 11-102800 | 4/1999 |
| JP | 11-243295 | 9/1999 |
| JP | 2000-243309 | 9/2000 |
| JP | 2000-294399 | 10/2000 |
| JP | 2001-6900 | 1/2001 |
| JP | 2001-009050 | 1/2001 |
| JP | 2001-129103 | 5/2001 |
| JP | 2001-346893 | 12/2001 |
| JP | 2002-164686 | 6/2002 |
| JP | A2003-504628 | 2/2003 |
| JP | 2003-517755 | 5/2003 |
| JP | 2004-031115 A | 1/2004 |
| JP | 2005-526578 | 9/2005 |
| JP | 2006-032282 | 2/2006 |
| JP | 05-046928 | 3/2008 |
| JP | 2008-507826 | 3/2008 |
| JP | 2009-515671 | 4/2009 |
| JP | 2009-516905 | 4/2009 |
| JP | 2010-536130 | 11/2010 |
| JP | 2011-505191 | 2/2011 |
| JP | 2011-505670 | 2/2011 |
| JP | 2011-507151 | 3/2011 |
| SU | 300137 | 11/1969 |
| SU | 569 635 | 8/1977 |
| TW | 200930160 | 7/2009 |
| TW | 200934682 | 8/2009 |
| TW | 200939908 | 9/2009 |
| TW | 200940120 | 10/2009 |
| WO | WO 1986/07229 | 12/1986 |
| WO | WO 1990/012413 | 10/1990 |
| WO | WO 1992/03028 | 2/1992 |

(56) References Cited

FOREIGN PATENT DOCUMENTS

| WO | WO 1993/02536 | 2/1993 |
|---|---|---|
| WO | WO 1998/17342 | 4/1998 |
| WO | WO-99/27839 A2 | 6/1999 |
| WO | WO 1999/27839 | 6/1999 |
| WO | WO 1999/39385 | 8/1999 |
| WO | WO 2000/40064 | 7/2000 |
| WO | WO 2000/49624 | 8/2000 |
| WO | WO 2001/026230 | 4/2001 |
| WO | WO 2001/026569 | 4/2001 |
| WO | WO 2002/007817 | 1/2002 |
| WO | WO-02/100485 A1 | 12/2002 |
| WO | WO 2002/100485 | 12/2002 |
| WO | WO 2003/039212 | 5/2003 |
| WO | WO 2003/092812 | 11/2003 |
| WO | WO 2004/026401 | 4/2004 |
| WO | WO 2004/101070 | 11/2004 |
| WO | WO 2005/099578 | 10/2005 |
| WO | WO 2006-012467 | 2/2006 |
| WO | WO 2006/083703 | 8/2006 |
| WO | WO 2006/124434 | 11/2006 |
| WO | WO 2007/061937 | 5/2007 |
| WO | WO 2007/084701 | 7/2007 |
| WO | WO 2007/130164 | 11/2007 |
| WO | WO 2007/145906 | 12/2007 |
| WO | WO 2008/030911 | 3/2008 |
| WO | WO 2008/081480 | 10/2008 |
| WO | WO 2009/048745 | 4/2009 |
| WO | WO 2009/070173 | 6/2009 |
| WO | WO 2009/070588 | 6/2009 |
| WO | WO 2009/073480 | 6/2009 |
| WO | WO 2014/018706 | 1/2014 |
| WO | WO 2014/018876 | 1/2014 |

OTHER PUBLICATIONS

Communication pursuant to Article 94(3) EPC for EP15183802.6-1666, 4 pages (dated Feb. 23, 2017).
"Beam Delivery and Properties," *Journal of the ICRU*, 2007, 7(2):20 pages.
"510(k) Summary: Ion Beam Applications S.A.", FDA, Jul. 12, 2001, 5 pages.
"510(k) Summary: Optivus Proton Beam Therapy System", Jul. 21, 2000, 5 pages.
"An Accelerated Collaboration Meets with Beaming Success," Lawrence Livermore National Laboratory, Apr. 12, 2006, S&TR, Livermore, California, pp. 1-3, http://www.llnl.gov/str/April06/Caporaso.html.
"CPAC Highlights Its Proton Therapy Program at ESTRO Annual Meeting", TomoTherapy Incorporated, Sep. 18, 2008, Madison, Wisconsin, pp. 1-2.
"Indiana's mega-million proton therapy cancer center welcomes its first patients" [online] Press release, Health & Medicine Week, 2004, retrieved from NewsRx.com, Mar. 1, 2004, pp. 119-120.
"LLNL, UC Davis Team Up to Fight Cancer," Lawrence Livermore National Laboratory, Apr. 28, 2006, SF-06-04-02, Livermore, California, pp. 1-4.
"Patent Assignee Search Paul Scherrer Institute," Library Services at Fish & Richardson P.C., Mar. 20, 2007, 40 pages.
"Patent Prior Art Search for 'Proton Therapy System'," Library Services at Fish & Richardson P.C., Mar. 20, 2007, 46 pages.
"Superconducting Cyclotron Contract" awarded by Paul Scherrer Institute (PSI), Villigen, Switzerland, http://www.accel.de/News/superconducting_cyclotron_contract.htm, Jan. 2009, 1 page.
"The Davis 76-Inch Isochronous Cyclotron", Beam on: Crocker Nuclear Laboratory, University of California, 2009, 1 page.
"The K100 Neutron-therapy Cyclotron," National Superconducting Cyclotron Laboratory at Michigan State University (NSCL), retrieved from: http://www.nscl.msu.edu/tech/accelerators/k100, Feb. 2005, 1 page.
"The K250 Proton therapy Cyclotron," National Superconducting Cyclotron Laboratory at Michigan State University (NSCL), retrieved from: http://www.nscl.msu.edu/tech/accelerators/k250.html, Feb. 2005, 2 pages.

"The K250 Proton-therapy Cyclotron Photo Illustration," National Superconducting Cyclotron Laboratory at Michigan State University (NSCL), retrieved from: http://www.nscl.msu.edu/media/image/experimental-equipment-technology/250.html, Feb. 2005, 1 page.
18th Japan Conference on Radiation and Radioisotopes [Japanese], Nov. 25-27, 1987, 9 pages.
Abrosimov et al., "1000MeV Proton Beam Therapy facility at Petersburg Nuclear Physics Institute Synchrocyclotron," Medical Radiology (Moscow) 32, 10 (1987) revised in Journal of Physics, Conference Series 41, 2006, pp. 424-432, Institute of Physics Publishing Limited.
Abrosimov et al., "Neutron Time-of-flight Spectrometer Gneis at the Gatchina 1 GeV Protron Syncrhocyclotron", Mar. 9, 1985 and revised form Jul. 31, 1985, Lemingrad Nuclear Physics Institute, Gatchina, 188350, USSR (15 pages).
Adachi et al., "A 150MeV FFAG Synchrotron with "Return-Yoke Free" Magent," *Proceedings of the 2001 Particle Accelerator Conference*, Chicago, 2001, 3 pages.
Ageyev et al., "The IHEP Accelerating and Storage Complex (UNK) Status Report," *11th International Conference on High-Energy Accelerators*, 1980, pp. 60-70.
Agosteo et al., "Maze Design of a gantry room for proton therapy," *Nuclear Instruments & Methods in Physics Research*, 1996, Section A, 382, pp. 573-582.
Alexeev et al., "R4 Design of Superconducting Magents for Proton Synchrotrons," *Proceedings of the Fifth International Cryogenic Engineering Conference*, 1974, pp. 531-533.
Allardyce et al., "Performance and Prospects of the Reconstructed CERN 600 MeV Synchrocyclotron," *IEEE Transactions on Nuclear Science USA*, Jun. 1977, ns-24:(3)1631-1633.
Alonso, "Magnetically Scanned Ion Beams for Radiation Therapy," Accelerator & Fusion Research Division, Lawrence Berkeley Laboratory, Berkeley, CA, Oct. 1988, 13 pages.
Amaldi et al., "The Italian project for a hadrontherapy centre" *Nuclear Instruments and Methods in Physics Research A*, 1995, 360, pp. 297-301.
Amaldi, "Overview of the world landscape of Hadrontherapy and the projects of the TERA foundation," Physica Medica, An International journal Devoted to the Applications of Physics to Medicine and Biology, Jul. 1998, vol. XIV, Supplement 1, 6th Workshop on Heavy Charged Particles in Biology and Medicine, Instituto Scientific Europeo (ISE), Sep. 29-Oct. 1, 1977, Baveno, pp. 76-85.
Anferov et al., "Status of the Midwest Proton Radiotherapy Institute," Proceedings of the 2003 Particle Accelerator Conference, 2003, pp. 699-701.
Anferov et al., "The Indiana University Midwest Proton Radiation Institute," Proceedings of the 2001 Particle Accelerator Conference, 2001, Chicago, pp. 645-647.
Appun, "Various problems of magnet fabrication for high-energy accelerators," *Journal for All Engineers Interested in the Nuclear Field*, 1967, pp. 10-16 (1967) [Lang.: German], English bibliographic information (http://www.osti.gov/energycitations/product.biblio.jsp?osti_id=4442292).
Arduini et al. "Physical specifications of clinical proton beams from a synchrotron," *Med. Phys*, Jun. 1996, 23 (6): 939-951.
Badano et al., "Proton-Ion Medical Machine Study (PIMMS) Part I," PIMMS, Jan. 1999, 238 pages.
Beeckman et al., "Preliminary design of a reduced cost proton therapy facility using a compact, high field isochronous cyclotron," *Nuclear Instruments and Methods in Physics Research* B56/57, 1991, pp. 1201-1204.
Bellomo et al., "The Superconducting Cyclotron Program at Michigan State University," *Bulletin of the American Physical Society*, Sep. 1980, 25(7):767.
Benedikt and Carli, "Matching to Gantries for Medical Synchrotrons" *IEEE Proceedings of the 1997 Particle Accelerator Conference*, 1997, pp. 1379-1381.
Bieth et al., "A Very Compact Protontherapy Facility Based on an Extensive Use of High Temperature Superconductors (HTS)" *Cyclotrons and their Applications 1998*, Proceedings of the Fifteenth International Conference on Cyclotrons and their Applications, Caen, Jun. 14-19, 1998, pp. 669-672.

(56) References Cited

OTHER PUBLICATIONS

Bigham, "Magnetic Trim Rods for Superconducting Cyclotrons," Nuclear Instruments and Methods (North-Holland Publishing Co.), 1975, 141:223-228.
Bimbot, "First Studies of the External Beam from the Orsay S.C. 200 MeV," Institut de Physique Nucleaire, BP 1, Orsay, France, *IEEE*, 1979, pp. 1923-1926.
Blackmore et al., "Operation of the Triumf Proton Therapy Facility," *IEEE Proceedings of the 1997 Particle Accelerator Conference*, May 12-16, 19973:3831-3833.
Bloch, "The Midwest Proton Therapy Center," Application of Accelerators in Research and Industry, Proceedings of the Fourteenth Int'l. Conf., Part Two, Nov. 1996, pp. 1253-1255.
Blosser et al., "Problems and Accomplishments of Superconducting Cyclotrons," Proceedings of the 14$^{th}$ International Conference, Cyclotrons and Their Applications, Oct. 1995, pp. 674-684.
Blosser et al., "Superconducting Cyclotrons", Seventh International Conference on Cyclotrons and their Applications, Aug. 19-22, 1975, pp. 584-594.
Blosser et al., "A Compact Superconducting Cyclotron for the Production of High Intensity Protons," Proceedings of the 1997 Particle Accelerator Conference, May 12-16, 1997, 1:1054-1056.
Blosser et al., "Advances in Superconducting Cyclotrons at Michigan State University," Proceedings of the 11$^{th}$ International Conference on Cyclotrons and their Applications, Oct. 1986, pp. 157-167, Tokyo.
Blosser et al., "Characteristics of a 400 (Q2/A) MeV Super-Conducting Heavy-Ion Cyclotron," Bulletin of the American Physical Society, Oct. 1974, p. 1026.
Blosser et al., "Medical Accelerator Projects at Michigan State Univ." IEEE Proceedings of the 1989 Particle Accelerator Conference, Mar. 20-23, 1989, 2:742-746.
Blosser et al., "Superconducting Cyclotron for Medical Application", *IEEE Transactions on Magnetics*, Mar. 1989, 25(2): 1746-1754.
Blosser, "Application of Superconductivity in Cyclotron Construction," *Ninth International Conference on Cyclotrons and their Applications*, Sep. 1981, pp. 147-157.
Blosser, "Applications of Superconducting Cyclotrons," Twelfth International Conference on Cyclotrons and Their Applications, May 8-12, 1989, pp. 137-144.
Blosser, "Future Cyclotrons," AIP, *The Sixth International Cyclotron Conference*, 1972, pp. 16-32.
Blosser, "Medical Cyclotrons," *Physics Today*, Special Issue Physical Review Centenary, Oct. 1993, pp. 70-73.
Blosser, "Preliminary Design Study Exploring Building Features Required for a Proton Therapy Facility for the Ontario Cancer Institute", Mar. 1991, MSUCL-760a, 53 pages.
Blosser, "Progress on the Coupled Superconducting Cyclotron Project," *Bulletin of the American Physical Society*, Apr. 1981, 26(4):558.
Blosser, "Synchrocyclotron Improvement Programs," *IEEE Transactions on Nuclear Science USA*, Jun. 1969, 16(3):Part I, pp. 405-414.
Blosser, "The Michigan State University Superconducting Cyclotron Program," Nuclear Science, Apr. 1979, NS-26(2):2040-2047.
Blosser, H., Present and Future Superconducting Cyclotrons, *Bulletin of the American Physical Society*, Feb. 1987, 32(2):171 Particle Accelerator Conference, Washington, D.C.
Blosser, H.G., "Superconducting Cyclotrons at Michigan State University", Nuclear Instruments & Methods in Physics Research, 1987,vol. B 24/25, part II, pp. 752-756.
Botha et al., "A New Multidisciplinary Separated-Sector Cyclotron Facility," *IEEE Transactions on Nuclear Science*, 1977, NS-24(3):1118-1120.
Chichili et al., "Fabrication of Nb3 Sn Shell-Type Coils with Pre-Preg Ceramic Insulation," American Institute of Physics Conference Proceedings, AIP USA, No. 711, (XP-002436709, ISSN: 0094-243X), 2004, pp. 450-457.

Chong et al., Radiology Clinic North American 7, 3319, 1969, 27 pages.
Chu et al., "Performance Specifications for Proton Medical Facility," Lawrence Berkeley Laboratory, University of California, Mar. 1993, 128 pages.
Chu et al., "Instrumentation for Treatment of Cancer Using Proton and Light-ion Beams," Review of Scientific Instruments, Aug. 1993, 64 (8):2055-2122.
Chu, "Instrumentation in Medical Systems," Accelerator and Fusion Research Division, Lawrence Berkeley Laboratory, University of California, Berkeley, CA, May 1995, 9 pages.
Cole et al., "Design and Application of a Proton Therapy Accelerator," Fermi National Accelerator Laboratory, *IEEE*, 1985, 5 pages.
Collins, et al., "The Indiana University Proton Therapy System," Proceedings of EPAC 2006, Edinburgh, Scotland, 2006, 3 pages.
Conradi et al., "Proposed New Facilities for Proton Therapy at iThemba Labs," *Proceedings of EPAC*, 2002, pp. 560-562.
Copy of C/E Source of Ions for Use in Sychro-Cyclotrons Search, Jan. 31, 2005, 9 pages.
Copy of Source Search "Cites of U.S. and Foreign Patents/Published applications in the name of Mitsubishi Denki Kabushiki Kaisha and Containing the Keywords (Proton and Synchrocyclotron)," Jan. 2005, 8 pages.
Cosgrove et al., "Microdosimetric Studies on the Orsay Proton Synchrocyclotron at 73 and 200 MeV," *Radiation Protection Dosimetry*, 1997, 70(1-4):493-496.
Coupland, "High-field (5 T) pulsed superconducting dipole magnet," *Proceedings of the Institution of Electrical Engineers*, Jul. 1974, 121(7):771-778.
Coutrakon et al. "Proton Synchrotrons for Cancer Therapy," Application of Accelerators in Research and Industry—Sixteenth International Conf., American Institute of Physics, Nov. 1-5, 2000, vol. 576, pp. 861-864.
Coutrakon et al., "A prototype beam delivery system for the proton medical accelerator at Loma Linda," *Medical Physics*, Nov./Dec. 1991, 18(6):1093-1099.
Cuttone, "Applications of a Particle Accelerators in Medical Physics," Istituto Nazionale di Fisica Nucleare-Laboratori Nazionali del Sud, V.S. Sofia, 44 Cantania, Italy, Jan. 2010, 17 pages.
Dahl P, "Superconducting Magnet System," American Institute of Physics, AIP Conference Proceedings, 1987-1988, 2: 1329-1376.
Dialog Search, Jan. 31, 2005, 17 pages.
Dugan et al., "Tevatron Status" IEEE, Particle Accelerator Conference, Accelerator Science & Technology, 1989, pp. 426-430.
Eickhoff et al., "The Proposed Accelerator Facility for Light Ion Cancer Therapy in Heidelberg," Proceedings of the 1999 Particle Accelerator Conference, New York, 1999, pp. 2513-2515.
Enchevich et al., "Minimizing Phase Losses in the 680 MeV Synchrocyclotron by Correcting the Accelerating Voltage Amplitude," *Atonmaya Energiya*, 1969, 26:(3):315-316.
Endo et al., "Compact Proton and Carbon Ion Synchrotrons for Radiation Therapy," Proceedings of EPAC 2002, Paris France, 2002, pp. 2733-2735.
Flanz et al., "Treating Patients with the NPTC Accelerator Based Proton Treatment Facility," Proceedings of the 2003 Particle Accelerator Conference, 2003, pp. 690-693.
Flanz et al., "Large Medical Gantries," Particle Accelerator Conference, Massachusetts General Hospital, 1995, pp. 1-5.
Flanz et al., "Operation of a Cyclotron Based Proton Therapy Facility", Massachusetts General Hospital, Boston, MA 02114, pp. 1-4, retrieved from Internet in 2009.
Flanz et al., "The Northeast Proton Therapy Center at Massachusetts General Hospital," Fifth Workshop on Heavy Charge Particles in Biology and Medicine, GSI, Darmstadt, Aug. 1995, 11 pages.
Flood and Frazier, "The Wide-Band Driven RF System for the Berkeley 88-Inch Cyclotron," American Institute of Physics, Conference Proceedings., No. 9, 1972, 459-466.
Foster and Kashikhin, "Superconducting Superferric Dipole Magent with Cold Iron Core for the VLHC," *IEEE Transactions on Applied Superconductivity*, Mar. 2002, 12(1):111-115.

(56) References Cited

OTHER PUBLICATIONS

Friesel et al., "Design and Construction Progress on the IUCF Midwest Proton Radiation Institute," Proceedings of EPAC 2002, 2002, pp. 2736-2738.

Fukumoto et al., "A Proton Therapy Facility Plan" Cyclotrons and their Applications, Proceedings of the 13th International Conference, Vancouver, Canada, Jul. 6-10, 1992, pp. 258-261.

Fukumoto, "Cyclotron Versus Synchrotron for Proton Beam Therapy," KEK Prepr., No. 95-122, Oct. 1995, pp. 533-536.

Goto et al., "Progress on the Sector Magnets for the Riken SRC," American Institute of Physics, CP600, Cyclotrons and Their Applications 2001, Sixteenth International Conference, 2001, pp. 319-323.

Graffman et al., "Design Studies for a 200 MeV Proton Clinic for Radiotherapy," AIP Conference Proceedings: Cyclotrons—1972, 1972, No. 9, pp. 603-615.

Graffman et al., *Acta Radiol. Therapy Phys. Biol.* 1970, 9, 1 (1970).

Graffman, et. al. "Proton radiotherapy with the Uppsala cyclotron. Experience and plans" *Strahlentherapie*, 1985, 161(12):764-770.

Hede, "Research Groups Promoting Proton Therapy 'Lite,'" Journal of the National Cancer Institute, Dec. 6, 2006, 98(23):1682-1684.

Heinz, "Superconducting Pulsed Magnetic Systems for High-Energy Synchrotrons," *Proceedings of the Fourth International Cryogenic Engineering Conference*, May 24-26, 1972, pp. 55-63.

Hentschel et al., "Plans for the German National Neutron Therapy Centre with a Hospital-Based 70 MeV Proton Cyclotron at University Hospital Essen/Germany," Cyclotrons and their Applications, Proceedings of the Fifteenth International Conference on Cyclotrons and their Applications, Caen, Franco, Jun. 14-19, 1998, pp. 21-23.

Hepburn et al., "Superconducting Cyclotron Neutron Source for Therapy," *International Journal of Radiation Oncology Biology Physics*, vol. 3 complete, 1977, pp. 387-391.

Hirabayashi, "Development of Superconducting Magnets for Beam Lines and Accelerator at KEK," *IEEE Transaction on Magnetics*, Jan. 1981, Mag-17(1):728-731.

Ishibashi and McInturff, "Winding Design Study of Superconducting 10 T Dipoles for a Synchrotron," *IEEE Transactions on Magnetics*, May 1983, MAG-19(3):1364-1367.

Ishibashi and McInturff, "Stress Analysis of Superconducting 10T Magnets for Synchrotron," Proceedings of the Ninth International Cryogenic Engineering Conference, May 11-14, 1982, pp. 513-516.

Jahnke et al., "First Superconducting Prototype Magnets for a Compact Synchrotron Radiation Source in Operation," *IEEE Transactions on Magnetics*, Mar. 1988, 24(2):1230-1232.

Jones and Dershem, "Synchrotron Radiation from Proton in a 20 TEV, 10 TESLA Superconducting Super Collider" *Proceedings of the 12th International Conference on High-Energy Accelerator*, Aug. 11-16, 1983, pp. 138-140.

Jones and Mills, "The South African National Accelerator Centre: Particle Therapy and Isotope Production Programmes," *Radiation Physics and Chemistry*, Apr.-Jun. 1998, 51(4-6):571-578.

Jones et al., "Status Report of the NAC Particle Therapy Programme," *Stralentherapie und Onkologie*, vol. 175, Suppl. II, Jun. 1999, pp. 30-32.

Jones, "Progress with the 200 MeV Cyclotron Facility at the National Accelerator Centre," Commission of the European Communities Radiation Protection Proceedings, Fifth Symposium on Neutron Dosimetry, Sep. 17-21, 1984, vol. II, pp. 989-998.

Jones, "Present Status and Future Trends of Heavy Particle Radiotherapy," Cyclotrons and their Applications 1998, Proceedings of the Fifteenth International Conference on Cyclotrons and their Applications, Jun. 14-19, 1998, pp. 13-20.

Jongen et al., "Development of a Low-cost Compact Cyclotron System for Proton Therapy," *National Institute of Radiol. Sci*,1991, No. 81, pp. 189-200.

Jongen et al., "Progress report on the IBA-SHI small cyclotron for cancer therapy" *Nuclear Instruments and Methods in Physics Research*, Section B, vol. 79, issue 1-4, 1993, pp. 885-889.

Jongen et al., "The proton therapy system for the NPTC: Equipment Description and progress report," *Nuclear Instruments and methods in physics research*, 1996, Section B, 113(1): 522-525.

Jongen et al., "The proton therapy system for MGH's NPTC: equipment description and progress report," *Bulletin du Cancer/Radiotherapie, Proceedings of the meeting of the European Heavy Particle Therapy Group*, 1996, 83(Suppl. 1):219-222.

Kanai et al., "Three-dimensional Beam Scanning for Proton Therapy," Nuclear Instruments and Methods in Physic Research, Sep. 1, 1983, The Netherlands, 214(23):491-496.

Karlin et al., "Medical Radiology" (Moscow), 1983, 28, 13.

Karlin et al., "The State and Prospects in the Development of the Medical Proton Tract on the Synchrocyclotron in Gatchina," *Med. Radiol.*, Moscow, 28(3):28-32 (Mar. 1983)(German with English Abstract on end of page 32).

Kats and Druzhinin, "Comparison of Methods for Irradiation Prone Patients," *Atomic Energy*, Feb. 2003, 94(2):120-123.

Kats and Onosovskii, "A Simple, Compact, Flat System for the Irradiation of a Lying Patient with a Proton Beam from Different Directions," *Instruments and Experimental Techniques*, 1996, 39(1):132-134.

Kats and Onosovskii, "A Planar Magnetooptical System for the Irradiation of a Lying Patient with a Proton Beam from Various Directions," *Instruments and Experimental Techniques*, 1996, 39(1):127-131.

Khoroshkov et al.,"Moscow Hospital-Based Proton Therapy Facility Design," *Am. Journal Clinical Oncology: CCT*, Apr. 1994, 17(2):109-114.

Kim and Blosser, "Optimized Magnet for a 250 MeV Proton Radiotherapy Cyclotron," Cyclotrons and Their Applications 2001, May 2001, *Sixteenth International Conference*, pp. 345-347.

Kim and Yun, "A Light-Ion Superconducting Cyclotron System for Multi-Disciplinary Users," *Journal of the Korean Physical Society*, Sep. 2003, 43(3):325-331.

Kim et al., "Construction of 8T Magnet Test Stand for Cyclotron Studies," *IEEE Transactions on Applied Superconductivity*, Mar. 1993, 3(1):266-268.

Kim et al., "Design Study of a Superconducting Cyclotron for Heavy Ion Therapy," *Cyclotrons and Their Applications 2001, Sixteenth International Conference*, May 13-17, 2001, pp. 324-326.

Kim et al., "Trim Coil System for the Riken Cyclotron Ring Cyclotron," *Proceedings of the 1997 Particle Accelerator Conference, IEEE*, Dec. 1981, vol. 3, pp. 214-235 or 3422-3424, 1998.

Kim, "An Eight Tesla Superconducting Magnet for Cyclotron Studies," Ph.D. Dissertation, Michigan State University, Department of Physics and Astronomy, 1994, 138 pages.

Kimstrand, "Beam Modelling for Treatment Planning of Scanned Proton Beams," Digital Comprehensive Summaries of Uppsala dissertations from the Faculty of Medicine 330, Uppsala Universitet, 2008, 58 pages.

Kishida and Yano, "Beam Transport System for the RIKEN SSC (II)," *Scientific Papers of the Institute of Physical and Chemical Research*, Dec. 1981, 75(4):214-235.

Koehler et al., "Range Modulators for Protons and Heavy Ions," *Nuclear Instruments and Methods*, 1975, vol. 131, pp. 437-440.

Koto and Tsujii, "Future of Particle Therapy," Japanese Journal of Cancer Clinics, 2001, 47(1):95-98 [Lang.: Japanese], English abstract (http://sciencelinksjp/j-east/article/200206/000020020601A0511453.php).

Kraft et al., "Hadrontherapy in Oncology," U. Amaldi and Larrsson, editors Elsevier Science, 1994, 390 pages.

Krevet et al., "Design of a Strongly Curved Superconducting Bending Magnet for a Compact Synchrotron Light Source," *Advances in Cryogenic Engineering*, 1988, vol. 33, pp. 25-32.

Laisne et al., "The Orsay 200 MeV Synchrocyclotron," *IEEE Transactions on Nuclear Science*, Apr. 1979, NS-26(2):1919-1922.

Larsson et al., *Nature*, 1958, 182:1222.

Larsson, "Biomedical Program for the Converted 200-MeV Synchrocyclotron at the Gustaf Werner Institute," *Radiation Research*, 1985, 104:S310-S318.

Lawrence et al., "Heavy particles in acromegaly and Cushing's Disease," in Endocrine and Norendocrine Hormone Producing Tumors (Year Book Medical Chicago, 1973, pp. 29-61.

(56) References Cited

OTHER PUBLICATIONS

Lawrence et al., "Successful Treatment of Acromegaly: Metabolic and Clinical Studies in 145 Patients," *The Journal of Clinical Endocrinology and Metabolism*, Aug. 1970, 31(2), 21 pages.
Lawrence et al., "Treatment of Pituitary Tumors," (Excerpta medica, Amsterdam/American Elsevier, New York, 1973, pp. 253-262.
Lawrence, *Cancer*, 1957, 10:795.
Lecroy et al., "Viewing Probe for High Voltage Pulses," *Review of Scientific Instruments USA*, Dec. 1960, 31(12):1354.
Lin et al., "Principles and 10 Year Experience of the Beam Monitor System at the PSI Scanned Proton Therapy Facility", Center for Proton Radiation Therapy, Paul Scherrer Institute, CH-5232, Villigen PSI, Switzerland, 2007, 21 pages.
Linfoot et al., "Acromegaly," in Hormonal Proteins and Peptides, edited by C.H. Li, 1975, pp. 191-246.
Literature Author and Keyword Search, Feb. 14, 2005, 44 pages.
Literature Keyword Search, Jan. 24, 2005, 98 pages.
Literature Search and Keyword Search for Synchrocyclotron, Jan. 25, 2005, 68 pages.
Literature Search by Company Name/Component Source, Jan. 24, 2005, 111 pages.
Literature Search, Jan. 26, 2005, 37 pages.
Livingston et al., "A capillary ion source for the cyclotron," *Review Science Instruments*, Feb. 1939, 10:63.
Mandrillon, "High Energy Medical Accelerators," *EPAC 90, 2nd European Particle Accelerator Conference*, Jun. 12-16, 1990, 2:54-58.
Marchand et al., "IBA Proton Pencil Beam Scanning: an Innovative Solution for Cancer Treatment," Proceedings of EPAC 2000, Vienna, Austria, 3 pages.
Marti et al., "High Intensity Operation of a Superconducting Cyclotron," *Proceedings of the 14the International Conference, Cyclotrons and Their Applications*, Oct. 1995, pp. 45-48 (Oct. 1995).
Martin, "Operational Experience with Superconducting Synchrotron Magnets" *Proceedings of the 1987 IEEE Particle Accelerator Conference*, Mar. 16-19, 1987, vol. 3 of 3:1379-1382.
Meote et al., "ETOILE Hadrontherapy Project Review of Design Studies" *Proceedings of EPAC 2002*, 2002, pp. 2745-2747.
Miyamoto et al., "Development of the Proton Therapy System," *The Hitachi Hyoron*, 79(10):775-779 (1997) [Lang: Japanese], English abstract (http://www.hitachi.com/rev/1998/revfeb98/rev4706.htm).
Montelius et al., "The Narrow Proton Beam Therapy Unit at the Svedberg Laboratory in Uppsala," *ACTA Oncologica*, 1991, 30:739-745.
Moser et al., "Nonlinear Beam Optics with Real Fields in Compact Storage Rings," Nuclear Instruments & Methods in Physics Research/Section B, B30, Feb. 1988, No. 1, pp. 105-109.
Moyers et al., "A Continuously Variable Thickness Scatterer for Proton Beams Using Self-compensating Dual Linear Wedges" Lorna Linda University Medical Center, Dept. of Radiation Medicine, Lorna Linda, CA, Nov. 2, 1992, 21 pages.
National Cancer Institute Funding (Senate—Sep. 21, 1992) (www.thomas.loc.gov/cgi-bin/query/z?r102:S21SE2-712 (2 pages)
Nicholson, "Applications of Proton Beam Therapy," *Journal of the American Society of Radiologic Technologists*, May/Jun. 1996, 67(5): 439-441.
Nolen et al., "The Integrated Cryogenic—Superconducting Beam Transport System Planned for MSU," *Proceedings of the 12th International Conference on High-Energy Accelerators*, Aug. 1983, pp. 549-551.
Norimine et al., "A Design of a Rotating Gantry with Easy Steering for Proton Therapy," *Proceedings of EPAC 2002*, 2002, pp. 2751-2753.
Ogino, Takashi, "Heavy Charged Particle Radiotherapy-Proton Beam", Division of Radiation Oncology, National Cancer Hospital East, Kashiwa, Japan, Dec. 2003, 7 pages.
Okumura et al., "Overview and Future Prospect of Proton Radiotherapy," *Japanese Journal of Cancer Clinics*, 1997, 43(2):209-214 [Lang.: Japanese].
Okumura et al., "Proton Radiotherapy" *Japanese Journal of Cancer and Chemotherapy*, 1993, 10. 20(14):2149-2155[Lang.: Japanese].
Outstanding from Search Reports, "Accelerator of Polarized Portons at Fermilab," 2005, 20 pages.
Paganetti et al., "Proton Beam Radiotherapy—The State of the Art," Springer Verlag, Heidelberg, ISBN 3-540-00321-5, Oct. 2005,36 pages.
Palmer and Tollestrup, "Superconducting Magnet Technology for Accelerators," *Annual Review of Nuclear and Particle Science*, 1984, vol. 34, pp. 247-284.
Patent Assignee and Keyword Searches for Synchrocyclotron, Jan. 25, 2005, 78 pages.
Pavlovic, "Beam-optics study of the gantry beam delivery system for light-ion cancer therapy," *Nuclear Instruments and Methods in Physics Research*, Section A, Nov. 1997, 399(2):439-454(16).
Pedroni and Enge, "Beam optics design of compact gantry for proton therapy" *Medical & Biological Engineering & Computing*, May 1995, 33(3):271-277.
Pedroni and Jermann, "SGSMP: Bulletin Mar. 2002 Proscan Project, Progress Report on the PROSCAN Project of PSI" [online] retrieved from www.sgsmp.ch/protA23.htm, Mar. 2002, 5 pages.
Pedroni et al., "A Novel Gantry for Proton Therapy at the Paul Scherrer Institute," *Cycloctrons and Their Applications 2001: Sixteenth International Conference. AIP Conference Proceedings*, 2001, 600:13-17.
Pedroni et al., "The 200-MeV proton therapy project at the Paul Scherrer Institute: Conceptual design and practical realization," *Medical Physics*, Jan. 1995, 22(1):37-53.
Pedroni, "Accelerators for Charged Particle Therapy: Performance Criteria from the User Point of View," *Cyclotrons and their Applications, Proceedings of the 13th International Conference*, Jul. 6-10, 1992, pp. 226-233.
Pedroni, "Latest Developments in Proton Therapy" *Proceedings of EPAC 2000*, pp. 240-244, 2000.
Pedroni, "Status of Proton Therapy: results and future trends," Paul Scherrer Institute, Division of Radiation Medicine, 1994, 5 pages.
Peggs et al., "A Survey of Hadron Therapy Accelerator Technologies," Particle Accelerator Conference, Jun. 25-29, 2007, 7 pages.
Potts et al., "MPWP6-Therapy III: Treatment Aids and Techniques" *Medical Physics*, Sep./Oct. 1988, 15(5):798.
Pourrahimi et al., "Powder Metallurgy Processed Nb3Sn(Ta) Wire for High Field NMR magnets," *IEEE Transactions on Applied Superconductivity*, Jun. 1995, 5(2):1603-1606.
Prieels et al., "The IBA State-of-the-Art Proton Therapy System, Performances and Recent Results," *Application of Accelerators in Research and industry—Sixteenth Int'l. Conf., American Institute of Physics*, Nov. 1-5, 2000, 576:857-860.
Rabin et al., "Compact Designs for Comprehensive Proton Beam Clinical Facilities," *Nuclear Instruments & Methods in Physics Research*, Apr. 1989, Section B, vol. 40-41, Part II, pp. 1335-1339.
Research & Development Magazine, "Proton Therapy Center Nearing Completion." Aug. 1999, 41(9):2 pages, (www.rdmag.com).
Resmini "Design Characteristics of the K=800 Superconducting Cyclotron at M.S.U.," Cyclotron Laboratory, Michigan State University, East Lansing, Michigan 48824, IEEE Transaction on Nuclear Science, vol. NS-26, No. 2, Apr. 1979, 8 pages.
RetroSearch "Berkeley 88-Inch Cyclotron 'RF' or 'Frequency Control'," Jan. 21, 2005, 36 pages.
RetroSearch "Berkeley 88-Inch Cyclotron," Jan. 24, 2005, 170 pages.
RetroSearch "Bernard Gottschalk, Cyclotron, Beams, Compensated Upstream Modulator, Compensated Scatter," Jan. 21, 2005, 20 pages.
RetroSearch "Cyclotron with 'RF' or 'Frequency Control'," Jan. 21, 2005, 49 pages.
RetroSearch Gottschalk, Bernard, Harvard Cyclotron Wheel, Jan. 21, 2005, 20 pages.
RetroSearch "Loma Linda University Beam Compensation," Jan. 21, 2005, 60 pages.
RetroSearch "Loma Linda University, Beam Compensation Foil Wedge," Jan. 21, 2005, 15 pages.
Revised Patent Keyword Search, Jan. 25, 2005, 88 pages.

(56) References Cited

OTHER PUBLICATIONS

Rifuggiato et, al., "Status Report of the LNS Superconducting Cyclotron" *Nukleonika*, 2003, 48: S131-S134, Supplement 2.
Rode, "Tevatron Cryogenic System," *Proceedings of the 12th International Conference on High-energy Accelerators, Fermilab*, Aug. 11-16, 1983, pp. 529-535.
Salzburger et al., "Superconducting Synchrotron Magnets Supraleitende Synchrotronmagnete," Siemens A.G., Erlangen (West Germany). Abteilung Technische Physik, Report No. BMFT-FB-T-75-25, Oct. 1975, p. 147, Journal Announcement: GRAI7619; STAR1415, Subm-Sponsored by Bundesmin. Fuer Forsch. U. Technol. In German; English Summary.
Schillo et al,. "Compact Superconducting 250 MeV Proton Cyclotron for the PSI Proscan Proton Therapy Project," *Cyclotrons and Their Applications 2001, Sixteenth International Conference*, 2001, pp. 37-39.
Schneider et al., "Nevis Synchrocyclotron Conversion Program—RF System," *IEEE Transactions on Nuclear Science USA*, Jun. 1969, ns 16(3): 430-433.
Schneider et al., "Superconducting Cyclotrons," IEEE Transactions on Magnetics, vol. MAG-11, No. 2, Mar. 1975, New York, pp. 443-446.
Schreuder et al., "The Non-orthogonal Fixed Beam Arrangement for the Second Proton Therapy Facility at the National Accelerator Centre," *Application of Accelerators in Research and Industry, American Institute of Physics, Proceedings of the Fifteenth International Conference*, Nov. 1998, Part Two, pp. 963-966.
Schreuder, "Recent Developments in Superconducting Cyclotrons," *Proceedings of the 1995 Particle Accelerator Conference*, May 1-5, 1995, vol. 1, pp. 317-321.
Schubert and Blosser, "Conceptual Design of a High Field Ultra-Compact Cyclotron for Nuclear Physics Research," *Proceedings of the 1997 Particle Accelerator Conference*, May 12-16 1997, vol. 1, 3 pp. 1060-1062.
Schubert, "Extending the Feasibility Boundary of the Isochronous Cyclotron," Dissertation submitted to Michigan State University, 1997, Abstract http://adsabs.harvard.edu/abs/1998PhDT...147S.
Schubert et al., "Progress toward an experiment to study the effect of RF grounding in an internal ion source on axial oscillations of the beam in a cyclotron," National Superconducting Cyclotron Laboratory, Michigan State University, Report MSUCL-760, CP600, Cyclotrons and their Applications 2011, Sixteenth International Conference, 2001, pp. 274-276.
Shelaev et al., "Design Features of a Model Superconducting Synchrotron of JINR," *Proceedings of the 12th International Conference on High-energy Accelerators*, Aug. 11-16, 1983, pp. 416-418.
Shintomi et. Al, "Technology and Materials for the Superconducting Super Collider (SSC) Project," [Lang.: Japanese], The Iron and Steel Institute of Japan 00211575, 78(8): 1305-1313, 1992, http://ci.nii.ac.jp/naid/110001493249/en/.
Sisterson, "World Wide Proton Therapy Experience in 1997," *The American Insitute of Physics, Applications of Accelerators in Research and Industry, Proceedings of the Fifteenth International Conference*, Part Two, Nov. 1998, pp. 959-962.
Sisterson, "Clinical use of proton and ion beams from a world-wide perspective," *Nuclear Instruments and Methods in Physics Research*, Section B, 1989, 40-41:1350-1353.
Slater et al., "Developing a Clinical Proton Accelerator Facility: Consortium-Assisted Technology Transfer," *Conference Record of the 1991 IEEE Particle Accelerator Conference: Accelerator Science and Technology*, vol. 1, May 6-9, 1991, pp. 532-536.
Slater et al., "Development of a Hospital-Based Proton Beam Treatment Center," *International Journal of Radiation Oncology Biology Physics*, Apr. 1988, 14(4):761-775.
Smith et al., "The Northeast Proton Therapy Center at Massachusetts General Hospital" *Journal of Brachytherapy International*, Jan. 1997, pp. 137-139.

Snyder and Marti, "Central region design studies for a proposed 250 MeV proton cyclotron," *Nuclear Instruments and Methods in Physics Research*, Section A, 1995, vol. 355, pp. 618-623.
Soga, "Progress of Particle Therapy in Japan," Application of Accelerators in Research and Industry, American Institute of Physics, Sixteenth International Conference, Nov. 2000, pp. 869-872.
Spiller et al., "The GSI Synchrotron Facility Proposal for Acceleration of High Intensity Ion and Proton Beams" *Proceedings of the 2003 Particle Accelerator Conference*, May 12-16, 2003, vol. 1, pp. 589-591.
Stanford et al., "Method of Temperature Control in Microwave Ferroelectric Measurements," Sperry Microwave Electronics Company, Clearwater, Florida, Sep. 19, 1960, 1 page.
Tadashi et al., "Large superconducting super collider (SSC) in the planning and materials technology," 78(8):1305-1313, The Iron and Steel Institute of Japan 00211575, Aug. 1992.
Takada, "Conceptual Design of a Proton Rotating Gantry for Cancer Therapy," *Japanese Journal of Medical Physics*, 1995, 15(4):270-284.
Takayama et al., "Compact Cyclotron for Proton Therapy," *Proceedings of the $8^{th}$ Symposium on Accelerator Science and Technology*, Japan, Nov. 25-27, 1991, pp. 380-382.
Teng, "The Fermilab Tevatron," Coral Gables 1981, Proceedings, Gauge Theories, Massive Neutrinos, and Proton Decay, 1981, pp. 43-62.
The Journal of Practical Pharmacy, 1995, 46(1):97-103 [Japanese].
Tilly, et al., "Development and verification of the pulsed scanned proton beam at the Svedberg Laboratory in Uppsala", Physics in Medicine and Biology, Phys. Med. Biol. 52, pp. 2741-2454, 2007.
Tobias et al., *Cancer Research*, 1958, 18, 121 (1958).
Tom, "The Use of Compact Cyclotrons for Producing Fast Neutrons for Therapy in a Rotatable Isocentric Gantry," *IEEE Transaction on Nuclear Science*, Apr. 1979, 26(2):2294-2298.
Toyoda, "Proton Therapy System", Sumitomo Heavy Industries, Ltd., 2000, 5 pages.
Trinks et. al., "The Tritron: A Superconducting Separated-Orbit Cyclotron," *Nuclear Instruments and Methods in Physics Research*, Section A, 1986, vol. 244, pp. 273-282.
Tsuji, "The Future and Progress of Proton Beam Radiotherapy," *Journal of Japanese Society for Therapeutic Radiology and Oncology*, 1994, 6(2):63-76.
UC Davis School of Medicine, "Unlikely Partners Turn Military Defense into Cancer Offense", Current Issue Summer 2008, Sacramento, California, pp. 1-2.
Umegaki et al., "Development of an Advanced Proton Beam Therapy System for Cancer Treatment" *Hitachi Hyoron*, 2003, 85(9):605-608 [Lang.: Japanese], English abstract, http://www.hitachi.com/ICSFiles/afieldfile/2004/06/01/r2003_04_104.pdf or http://www.hitachi.com/rev/archive/2003/2005649_12606.html (full text) [Hitachi, 52(4), Dec. 2003].
Umezawa et al., "Beam Commissioning of the new Proton Therapy System for University of Tsukuba," *Proceedings of the 2001 Particle Accelerator Conference*, vol. 1, Jun. 18-22, 2001, pp. 648-650.
Van Steenbergen, "Superconducting Synchroton Development at BNL," *Proceedings of the 8th International Conference on High-Energy Accelerators CERN 1971*, 1971, pp. 196-198.
Van Steenbergen, "The CMS, A Cold Magnet Synchrotron to Upgrade the Proton Energy Range of the BNL Facility," *IEEE Transactions on Nuclear Science*, Jun. 1971, 18(3):694-698.
Vandeplassche et al., "235 MeV Cyclotron for MGH's Northeast Proton Therapy Center (NPTC): Present Status," EPAC 96, *Fifth European Partical Accelerator Conference*, vol. 3, Jun. 10-14, 1996, pp. 2650-2652.
Vorobiev et al., "Concepts of a Compact Achromatic Proton Gantry with a Wide Scanning Field", Nuclear Instruments and Methods in Physics Research, Section A., 1998, 406(2):307-310.
Vrenken et al., "A Design of a Compact Gantry for Proton Therapy with 2D-Scanning," *Nuclear Instruments and Methods in Physics Research*, Section A, 1999, 426(2):618-624.
Wikipedia, "Cyclotron" http://en.wikipedia.org/wiki/Cyclotron (originally visited Oct. 6, 2005, revisited Jan. 28, 2009), 7pages.
Wikipedia, "Synchrotron" http://en.wikipedia.org/wiki/Synchrotron (originally visited Oct. 6, 2005, revisited Jan. 28, 2009), 7 pages.

(56) References Cited

OTHER PUBLICATIONS

Worldwide Patent Assignee Search, Jan. 24, 2005, 224 pages.
Worldwide Patent Keyword Search, Jan. 24, 2005, 94 pages.
Wu, "Conceptual Design and Orbit Dynamics in a 250 MeV Superconducting Synchrocyclotron," Ph.D. Dissertation, Michigan State University, Department of Physics and Astronomy, 1990, 172 pages.
York et al., "Present Status and Future Possibilities at NSCL-MSU," EPAC 94, Fourth European Particle Accelerator Conference, pp. 554-556, Jun. 1994.
York et al., "The NSCL Coupled Cyclotron Project—Overview and Status," *Proceedings of the Fifteenth International Conference on Cyclotrons and their Applications*, Jun. 1998, pp. 687-691.
Yudelev et al., "Hospital Based Superconducting Cyclotron for Neutron Therapy: Medical Physics Perspective," *Cyclotrons and their applications 2001, 16th International Conference. American Institute of Physics Conference Proceedings*, vol. 600, May 13-17, 2001, pp. 40-43.
Zherbin et al., "Proton Beam Therapy at the Leningrad Synchrocyclotron (Clinicomethodological Aspects and Therapeutic Results)", Aug. 1987, 32(8):17-22, (German with English abstract on pp. 21-22).
U.S. Appl. No. 61/676,377, filed Jul. 27, 2012, including the USPTO electronic file for U.S. Appl. No. 61/676,377.
U.S. Appl. No. 13/949,459, filed Jul. 24, 2013, including the USPTO electronic file for U.S. Appl. No. 13/949,459.
U.S. Appl. No. 13/830,792, filed Mar. 14, 2013, including the USPTO electronic file for U.S. Appl. No. 13/830,792.
European Search Report from corresponding European Application 15183802.6 dated Feb. 8, 2016 (4 pages).
IP.com, "Invalidity Search: Voxel Scanning pulsed dose with decreasing intensity", *IP Solutions with a higher IQ*, May 21, 2013 (18 pages).f.
Orion, "Precision patient positioning system: Synchronicity with six degrees of freedom", www.leoni-healthcare.com.
Communication pursuant to Article 94(3) EPC for EP15183802.6, 4 pages (dated Sep. 12, 2017).

\* cited by examiner

PATIENT POSITIONING SYSTEM

TECHNICAL FIELD

This disclosure relates generally to a patient positioning system for use in medical applications, such as proton therapy.

BACKGROUND

Some particle therapy systems use an accelerator to generate a particle beam for treating afflictions, such as tumors. In some particle therapy systems, particles are accelerated in orbits inside a cavity in the presence of a magnetic field, and are removed from the cavity through an extraction channel. A magnetic field regenerator generates a magnetic field bump near the outside of the cavity to distort the pitch and angle of some orbits so that they precess towards, and eventually into, the extraction channel. A beam, comprised of the particles (the "particle beam"), exits the extraction channel.

The particle beam is used to treat a patient. Typically, a tumor is targeted with the particle beam in order to destroy all or part of the tumor. Application of the particle beam to an appropriate site includes positioning the patient so that the beam can be applied to the target.

SUMMARY

An example method for positioning a patient for treatment may comprise: associating fiducials with the patient; capturing an image of the fiducials and of an irradiation target while the patient is on a treatment couch, where the image is captured in a treatment room where treatment is to be performed; determining locations of the fiducials in the treatment room; determining locations of the fiducials in the image; determining a location of the irradiation target relative to a treatment system based on locations of the fiducials in the treatment room and in the image; and moving the treatment couch into a treatment position in the treatment room based on the location of the irradiation target. The example method may include one or more of the following features, either alone or in combination.

The image may be captured using an imaging system configured to capture internal images of the patient and of the fiducials. Determining the location of the fiducials in the treatment room may be performed using an imaging system that is configured to capture external images of the fiducials.

The image may comprise one or more of the following: an X-ray radiograph image, a computed tomography (CT) image that is captured by a CT imaging device, a magnetic resonance imaging (MRI) image that is captured by an MRI imaging device, a positron emission tomography (PET) image that is captured by a PET device, an image captured by a video surface imaging device, or an image captured by a SPECT/CT device. The image may comprise a three-dimensional (3D) image or a two-dimensional (2D) image.

The example method may further comprise treating the patient at the treatment position. Treating the patient may comprise irradiating the patient with protons using a treatment system comprising a particle accelerator system. The particle accelerator system may have an isocenter, and the isocenter may comprise the treatment position.

Determining the location of the irradiation target relative to the treatment system may comprise: determining, from the image, a location of the irradiation target relative to locations of the fiducials; determining locations of the fiducials relative to a reference coordinate system external to the image; and determining the location of the irradiation target relative to the treatment system based on the locations of the fiducials relative to the reference coordinate system and the location of the irradiation target from the image. The treatment system may have an isocenter. Moving the treatment couch into the treatment position may comprise moving the treatment couch so that the location of the irradiation target corresponds to the location of the isocenter. The reference coordinate system external to the image may be part of a real world space that includes the treatment system.

The example method may comprise securing the patient to the treatment couch relative to the fiducials; or securing the fiducials relative to the patient.

Moving the treatment couch into the treatment position may be performed using a robotic mechanism that moves the treatment couch automatically from an imaging position where the image is captured to the treatment position while the patient remains on the treatment couch. Moving the treatment couch may be performed manually while the patient remains on the treatment couch.

Associating fiducials with the patient may comprise arranging fiducials on the patient. Associating fiducials with the patient may comprise identifying anatomical landmarks on the patient, and designating the anatomical landmarks to be the fiducials. Associating fiducials with the patient may comprise arranging a frame over at least part of the patient, and securing the fiducials to the frame.

The example method may further comprise: determining an orientation of the irradiation target based on locations of the fiducials in the treatment room and in the image; and orienting the treatment based on the orientation of the irradiation target.

The example method may further comprise: tracking movement of the fiducials over time; and controlling movement of the treatment couch based on movement of the fiducials and/or controlling treatment based on movement of the fiducials. Capturing the image of the fiducials may comprise capturing the image at different times. The example method may further comprise: identifying movement of the fiducials based on different positions of the fiducials at different times; and controlling treatment based on the movement.

An example treatment system comprises: a treatment couch for holding a patient; fiducials associated with the patient; an imaging system to capture an image of the fiducials and of an irradiation target while the patient is on the treatment couch, where the image is captured in a treatment room where treatment is to be performed; a mechanism to move the treatment couch; and a computer system programmed to align locations of the fiducials to the fiducials in the image, and to determine a location of the irradiation target relative to a treatment system based on locations of the fiducials and based on the image. The movement of the treatment couch into a treatment position in the treatment room may be based on the location of the irradiation target. The example treatment system may include one or more of the following features, either alone or in combination.

The imaging system may be configured to capture internal images of the patient and of the fiducials. The imaging system may be a first imaging system and the treatment system may also comprise a second imaging system that is configured to capture external images of the fiducials.

The imaging system may comprise one or more of the following: an X-ray device to capture a radiograph image, a computed tomography (CT) device to capture a CT image, a magnetic resonance imaging (MRI) device to capture an MRI image, a positron emission tomography (PET) device to capture a PET image, an image captured by a video surface imaging device, or an image captured by a SPECT/CT device. The image may comprise a three-dimensional (3D) image or a two-dimensional (2D) image.

The example treatment system may comprise a particle accelerator system to treat the patient at the treatment position. Treating the patient may comprise irradiating the patient with protons output by the particle accelerator system. The particle accelerator system may have an isocenter, where the isocenter comprises the treatment position.

Determining the location of the irradiation target relative to the treatment system may comprise: determining, from the image, a location of the irradiation target relative to locations of the fiducials; determining locations of the fiducials relative to a reference coordinate system external to the image; and determining the location of the irradiation target relative to the treatment system based on the locations of the fiducials relative to the reference coordinate system and the location of the irradiation target from the image.

The treatment system may have an isocenter. Moving the treatment couch into the treatment position may comprise moving the treatment couch so that the location of the irradiation target corresponds to the location of the isocenter.

The reference coordinate system external to the image may be part of a real world space that includes the treatment system. The example system may comprise restraints to secure the patient to the treatment couch. The mechanism may comprise a robotic mechanism, which is configured to automatically move the treatment couch from an imaging position where the image is captured to the treatment position while the patient remains on the treatment couch.

The mechanism may be controllable to manually move the treatment couch while the patient remains on the treatment couch. The fiducials may be arranged on the patient. The fiducials may comprise anatomical landmarks on the patient. There may be a frame over at least part of the patient, and the fiducials may be secured to the frame.

The computer system may be programmed to perform operations comprising: determining an orientation of the irradiation target based on locations of the fiducials in the treatment room and in the image; and orienting the treatment based on the orientation of the irradiation target. The computer system may be programmed to perform operations comprising: tracking movement of the fiducials over time; and controlling movement of the treatment couch based on movement of the fiducials. The computer system may be programmed to perform operations comprising: tracking movement of the fiducials over time; and controlling treatment based on movement of the fiducials. Capturing the image of the fiducials may comprise capturing the image at different times; and the computer system may be programmed to perform operations comprising: identifying movement of the fiducials based on different positions of the fiducials at different times; and controlling treatment based on the movement.

Two or more of the features described in this disclosure, including those described in this summary section, may be combined to form implementations not specifically described herein.

Control of the various systems described herein, or portions thereof, may be implemented via a computer program product that includes instructions that are stored on one or more non-transitory machine-readable storage media, and that are executable on one or more processing devices (e.g., microprocessor(s), application-specific integrated circuit(s), programmed logic such as field programmable gate array(s), or the like). The systems described herein, or portions thereof, may be implemented as an apparatus, method, or electronic system that may include one or more processing devices and computer memory to store executable instructions to implement control of the stated functions.

The details of one or more implementations are set forth in the accompanying drawings and the description below. Other features, objects, and advantages will be apparent from the description and drawings, and from the claims.

DESCRIPTION OF THE DRAWINGS

Like reference symbols in the various drawings indicate like elements.

DETAILED DESCRIPTION

Described herein are examples of systems to position a patient for medical treatment. In some implementations, the example systems are used to position the patient for treatment using radiotherapy, such as proton or ion therapy. In some implementations, the proton or ion therapy may be performed using a system such as that described below. However, the example systems described herein may be used to position a patient for any type of medical treatment, and are not limited to radiotherapy or to use with proton or ion therapy.

Figure 1:
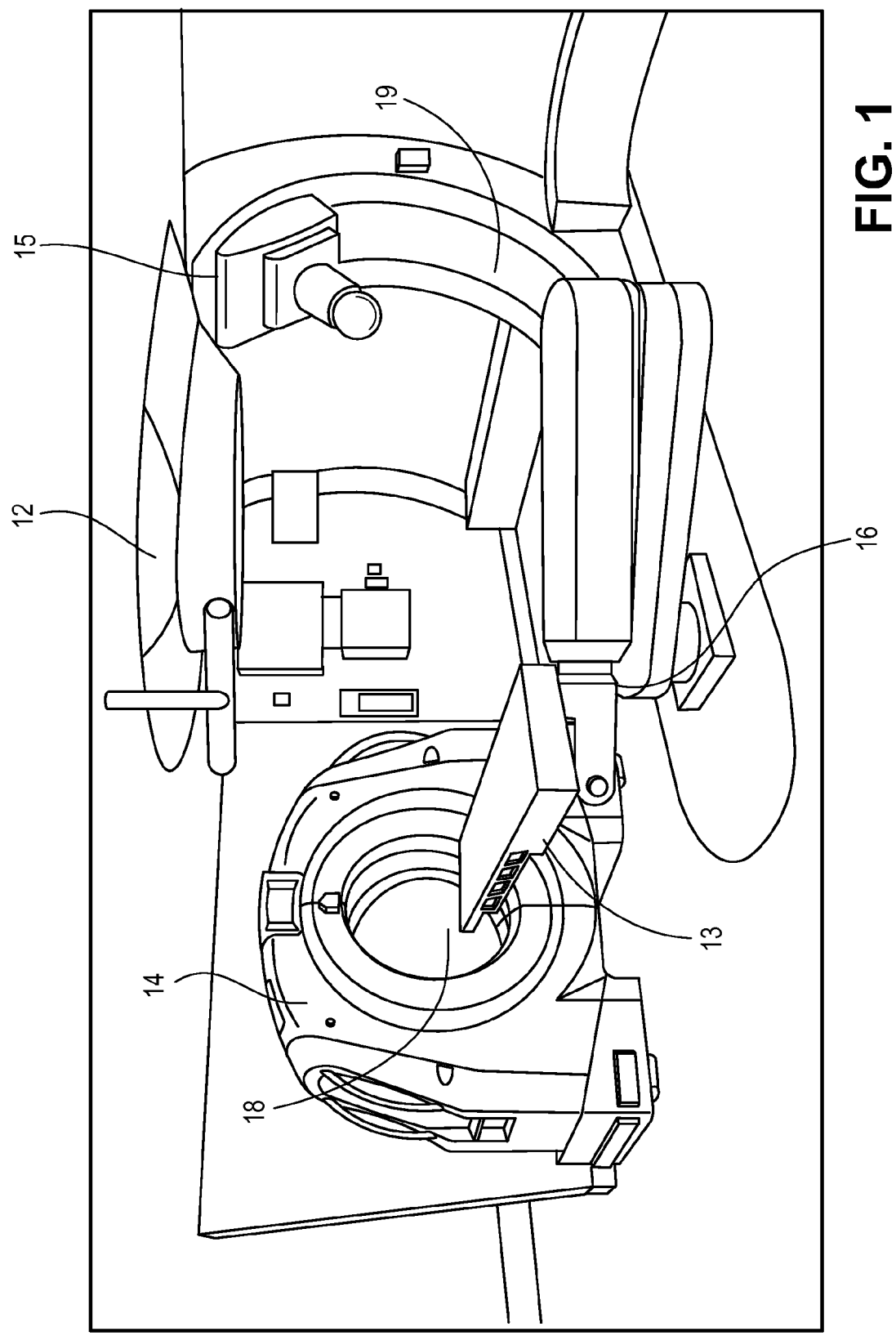
FIG. 1 is a diagram showing a perspective view of a treatment system in a treatment space.

FIG. 1 shows an example of a treatment space 12. Generally, the treatment space is the location where treatment of a patient is to be performed. For example, it may be a single room or multiple rooms. In this example, treatment space 12 includes, among other things, a treatment couch 13, an imaging system 14, and a proton therapy system 15. In other implementations, there may be different and/or additional components than those described herein.

In this example, treatment couch 13 includes a platform on which a patient may be disposed. The platform also may include one or more restraints (not shown) for holding the patient in place during movement of the couch and during treatment. The platform may, or may not, be padded and/or have a shape (e.g., an indentation) that corresponds to the shape of part of the patient. For example, prior to treatment, the patient may be placed in a mold that confirms that the contours of the back half of the patient, and the resulting molded structure may be incorporated into the platform of the treatment couch. A mold, such as this, incorporated into the treatment couch may reduce patient motion during movement of the treatment couch and during treatment.

A movement mechanism may move the treatment couch automatically from one position in treatment space 12 to another position in treatment space 12. For example, the movement mechanism may include a robotic arm 16 that is controllable to move the patient in six degrees of freedom, as described below. In some implementations, a manual mechanism, such as a manually movable arm, may replace the robotic arm, and be used to manually position the treatment couch. In some implementations, the couch may not be robotic. In some implementations, movement of the treatment couch may include a combination of robotic and manual positioning. Movement of the treatment couch typically occurs while the patient remains in place on the couch. For example, the treatment couch, with the patient thereon, may be moved between imaging position 18 and treatment position 19. In the imaging position, an image of the patient is captured. As described in more detail below, that image is used to position the patient for treatment in the treatment position.

In this regard, the treatment system is configured to determine the location of an irradiation target, such as a tumor, and to position the patient so that the irradiation target is in an appropriate position for treatment to be applied by proton therapy system 15. To this end, the movement mechanism (such as robotic arm 16) is configured to move treatment couch 13 between an imaging position 18 and a treatment position 19, which are both within treatment space 12, typically while the patient remains on the treatment couch. Movement may be automatic (e.g., without manual intervention) or may include a manual component. Once the patient is on the couch for imaging, in some implementations the example systems described herein do not require the patient to move off of the couch until treatment is completed. The movement mechanism may be responsive to commands from a computer system (not shown in FIG. 1) as described below, in order to position the patient relatively precisely at the treatment position.

In some implementations, the imaging system can be a three-dimensional (3D) imaging system. In some implementations, the imaging system can be a two-dimensional (2D) imaging system. In some implementations, imaging system 14 is a computed tomography (CT) system; however, in other implementations, different types of imaging systems may be used instead of, or in addition to, a CT system. For example, the imaging system may be, or include, one or more of the following types of imaging systems: a CT system, an X-ray device to capture a radiograph image, a magnetic resonance imaging (MRI) device to capture an MRI image, a positron emission tomography (PET) device to capture a PET image, a SPECT/CT device (where SPECT is Single-photon emission computed tomography), and/or a video surface imaging device, or any combination of these imaging devices (e.g., a combination of PET/CT, PET/MRI and/or SPECT/CT devices). In some implementations, images may be captured at different points in time so as to enable tracking of movement of a fiducial due, e.g., to patient movement, such as breathing or the like.

In some implementations, imaging system 14 includes an area (e.g., a hole) for receiving a patient and for capturing a 3D image of the patient. In the CT example, the image may include internal anatomical structures, such as organs, tumors, and bones, any of which may be an irradiation target (or fiducial, as described below). Imaging system 14 captures one or more images of the patient, or a selected part of the patient, typically the part of the patient where proton therapy is to be applied. These images are used to position the patient for treatment.

Figure 2:
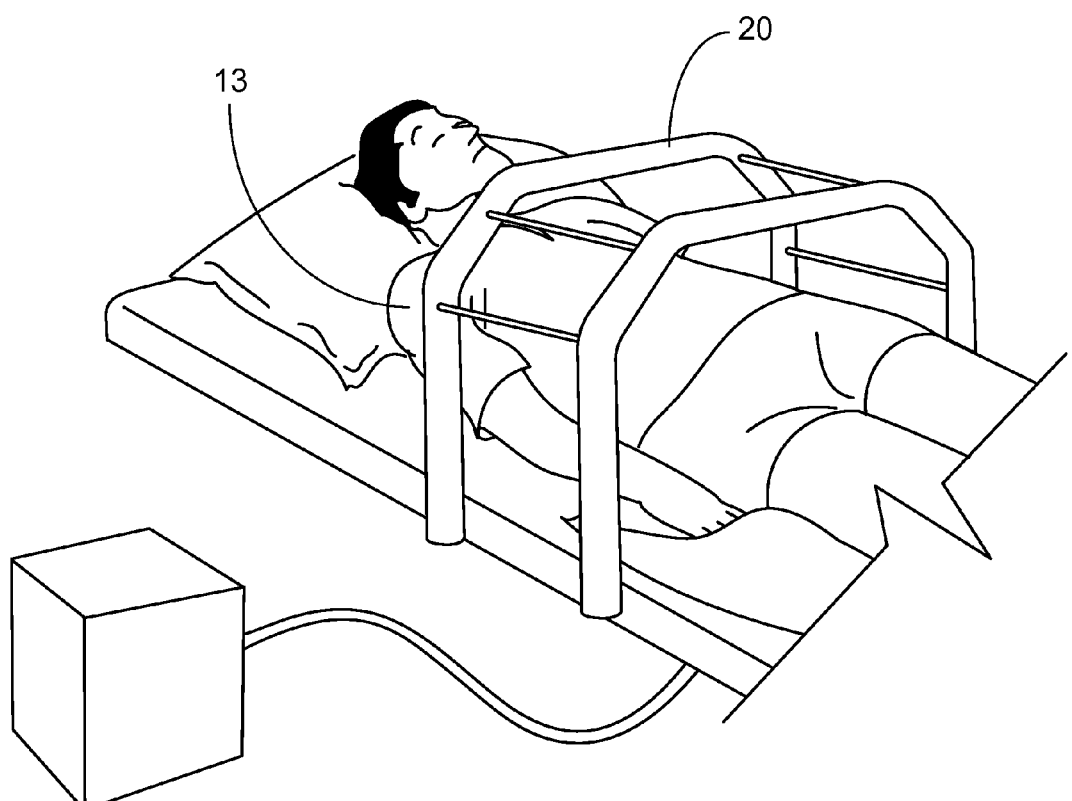
FIG. 2 is a diagram showing a perspective view of a treatment couch and fiducials arranged thereon.

In some implementations, the treatment couch may include one or more fiducials arranged thereon. Examples of fiducials 20 are shown in FIG. 2. These fiducials are typically made of metal or other material that shows-up on images, such as CT images. The fiducials may be arranged at areas around the patient, e.g., at and/or around parts of the patient where proton therapy is to be applied. In some implementations, at least three fiducials are arranged relative to the patient to enable use of a triangulation process to locate the irradiation target in both the CT image and the real-world. In other implementations more or less fiducials may be used. For example, in some implementations, one, two, four, five, six, seven, eight, nine, ten, and so forth fiducials may be used.

In some implementations, the fiducials may be secured directly to the treatment couch. In some implementations, the fiducials may be secured directly to the patient. In some implementations, the fiducials may be integrated in the treatment couch. In some implementations, a frame (shown in the figure) may be arranged over at least part of the patient, and the fiducials may be secured to the frame. In some implementations, the fiducials may be anatomical landmarks on or inside the patient. For example, the system may identify structural elements of a person's anatomy, such as teeth, bone, or the like, and designate those structural elements as fiducials. In some implementations, fiducials may be a combination of any two or more of the foregoing, e.g., anatomical structures and/or structural elements secured to the treatment couch, to the patient, to a frame, or the like.

The fiducials may have any appropriate shape; however, they are distinguishable from other structures on or in the patient and on or in the treatment couch. For example, the fiducials may be spherical, cubical, or polyhedral in shape. In some examples, the fiducials are fixed to the treatment couch rigidly, e.g., so that the fiducials do not move in response to movement of either the patient or the treatment couch. The arrangement of the fiducials may be dependent upon the location of the irradiation target, the type of treatment to be performed, the type of image to be captured, and so forth. Imaging system 14 captures images of the patient and fiducials. Those images are used to position the patient for treatment.

As noted above, in some implementations, robotic arm 16 moves treatment couch 13 from imaging position 18 to treatment position 19. There, the patient (not shown in FIG. 1) on the treatment couch is treated using proton therapy, at least in this example implementation. The location to which the treatment is to be applied is determined, in part, based upon the image captured by imaging system 14. In this regard, in example implementations, (i) the imaging system captures an image of the fiducials and of an irradiation target while the patient is on the treatment couch; (ii) the robotic arm moves the treatment couch towards a treatment position after the image(s) are captured; and (iii) a computer system performs operations that include determining real-world locations of the fiducials following movement of the treatment couch, aligning locations of the fiducials to the locations of the fiducials in the image, determining a location of the irradiation target relative to a treatment system based on locations of the fiducials and based on the image, and controlling movement of the robotic arm so as to move the treatment couch (and thus the irradiation target) into the treatment position, which may be, for example, an isocenter of the proton therapy system. In some implementations, the isocenter of the irradiation target, which may be identified during the treatment planning phase, is positioned at the isocenter of the proton therapy system.

In some implementations, a second imaging system is associated with (e.g., part of or in communication with) the treatment system of FIG. 1. The second imaging system may be configured to capture images in the treatment space, and need not necessarily be capable of capturing images of patient internal structures, although the second imaging system may be configured to capture images of the patient's internal structures, in some cases. The second imaging system may be used alone, or in concert with, a computing system to detect real-world locations of the fiducials in the treatment space. The locations of the fiducials are detected relative to one or more reference points in a 3D space that defines the treatment space. For example, the treatment space may be defined within a 3D coordinate system, and the locations of the fiducials may be identified by appropriate coordinates in that coordinate system. Accordingly, in some implementations, the locations of the fiducials are detected relative to the reference coordinate system.

Figure 3:
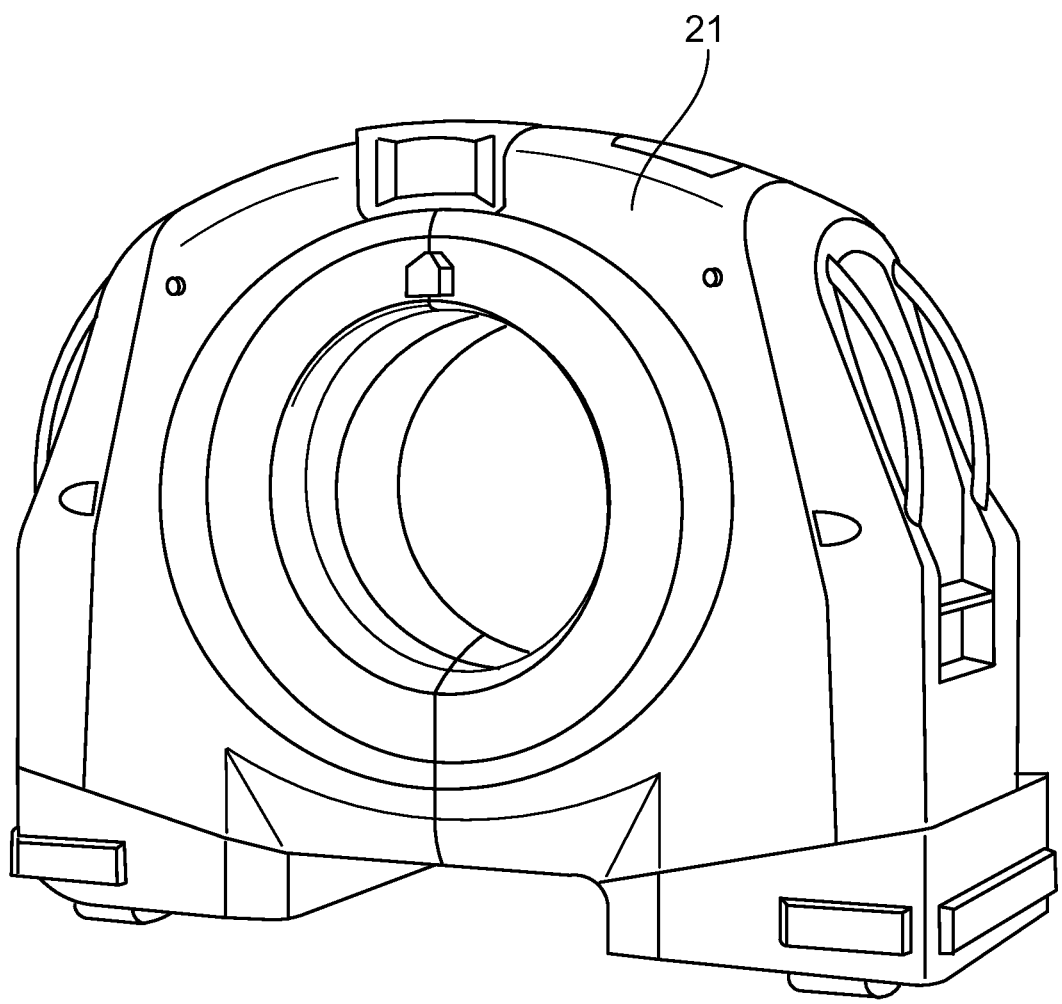
FIG. 3 is a perspective view of an imaging device that may be used in the treatment system of FIG. 1.

FIG. 3 shows an example of a portable CT scanner 21 that may function as imaging system 14. In this example, portable CT scanner 21 is a BodyTom® scanner from NeuroLogica Corp.; however, in other implementations, different types of imaging devices may be used that can be portable or not portable. In other implementations, the imaging apparatus may be mounted on, or near, to the proton therapy system, rather than being the CT scanner. The imaging apparatus may include cameras or the like that are used to identify the fiducials in the real-world coordinate system, and to communicate with a computer system (not shown in FIG. 3) to identify the locations of the fiducials in the coordinate system. The computer system may include one or more processing devices, examples of which are described below, that may exchange communications with all or part of the components of the treatment system, including the CT scanner, the proton therapy system, the second imaging system, the movement mechanism for the treatment couch, and so forth.

The fiducials are also arranged within a local 3D coordinate system. The location and orientation of this local 3D coordinate system are stored in computer memory. During movement of the treatment couch (and thus the patient), this local coordinate system is aligned to the treatment space 3D coordinate system.

Figure 4:
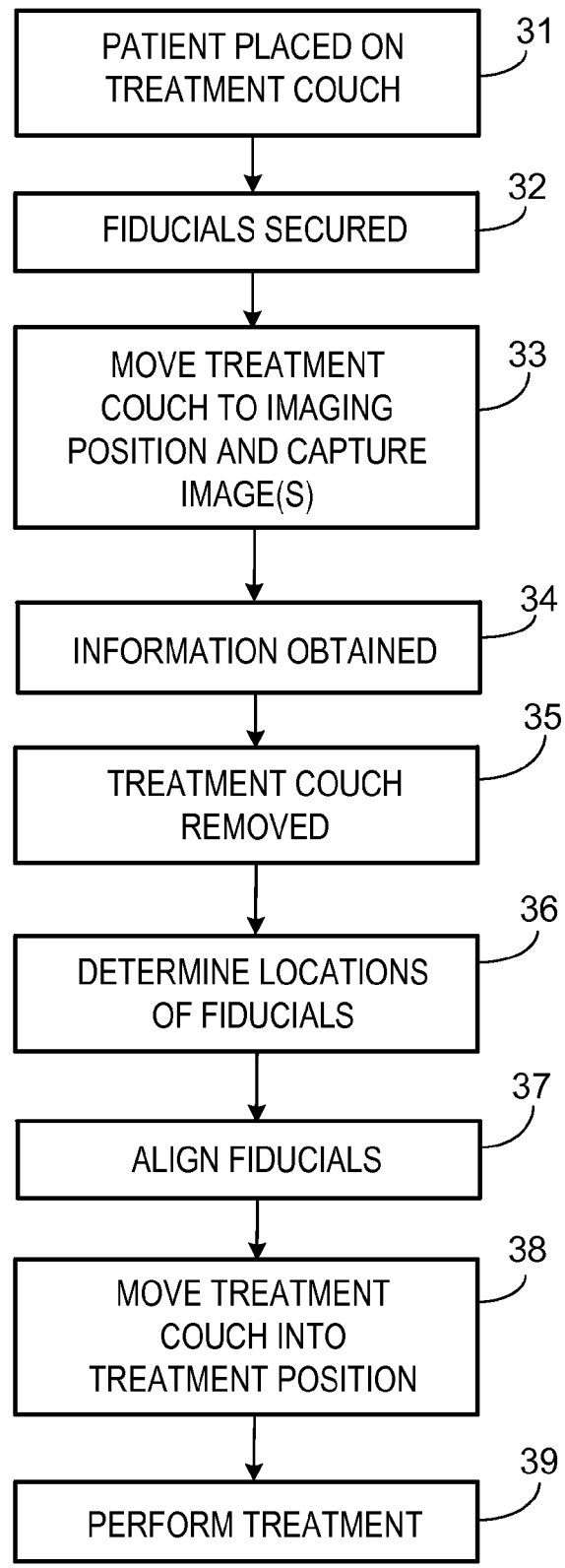
FIG. 4 is a flowchart showing a process that may be performed by the treatment system of FIG. 1.
Figure 5:
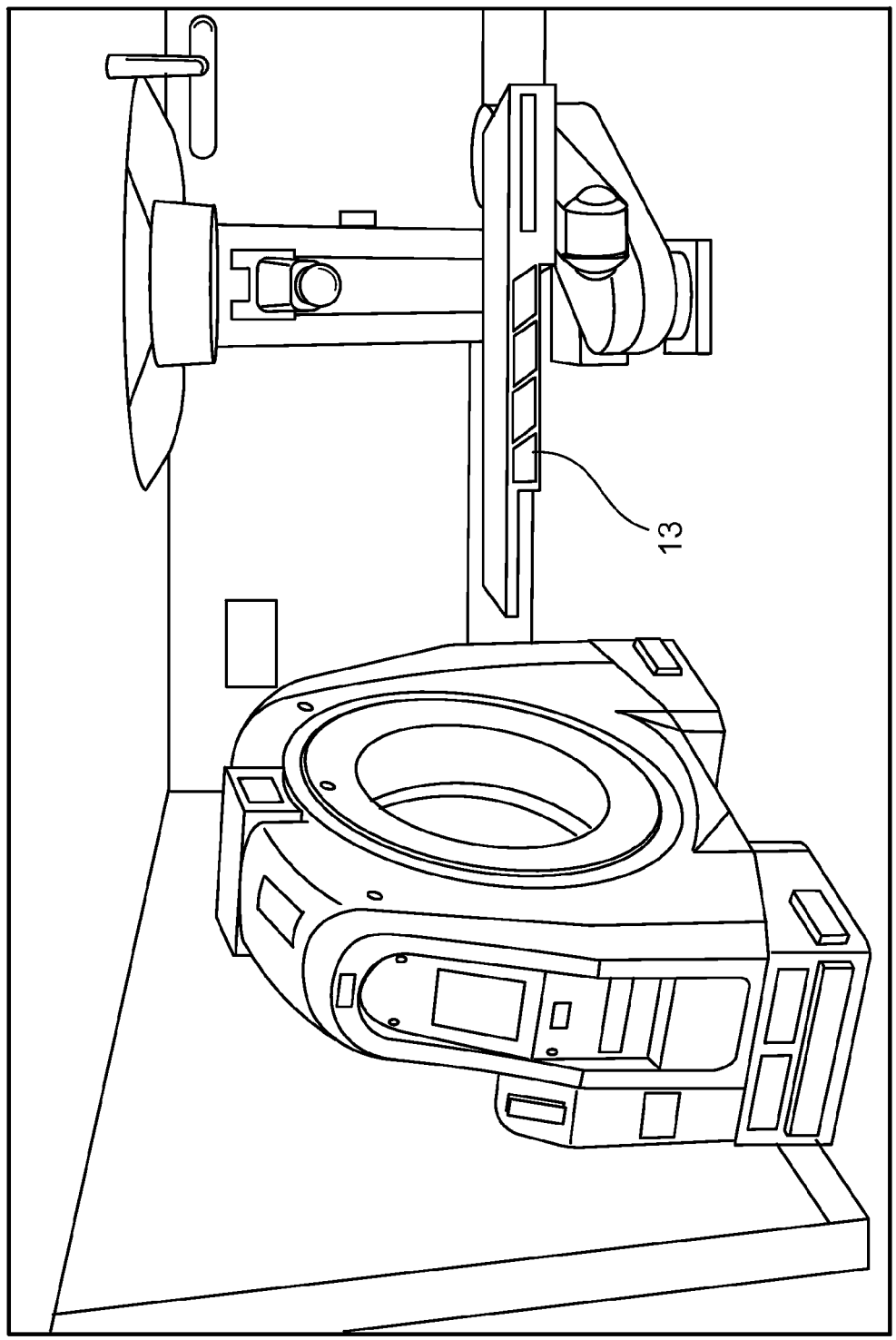
FIG. 5 is a diagram showing a perspective view of the treatment system of FIG. 1.

Referring to FIG. 4, an example process is shown for capturing stereotactic images in a treatment system, and for using those images to position a patient for treatment. Referring also to FIG. 5, in this example implementation, a patient (not shown) is placed (31) on treatment couch 13, and fiducials are arranged, and secured, (32) directly to positions on the treatment couch near to the part of the patient to be treated (e.g., near to the irradiation target). The proximity of the fiducials to the irradiation target may vary depending upon the size of the target, the type of treatment to be performed, and other factors. Placement of the fiducials is typically performed in the treatment space, which includes both imaging system 14 and proton therapy system 15 (see, e.g., FIG. 1). As explained above, fiducials may be placed elsewhere, or anatomical structures may be used as fiducials.

Figure 6:
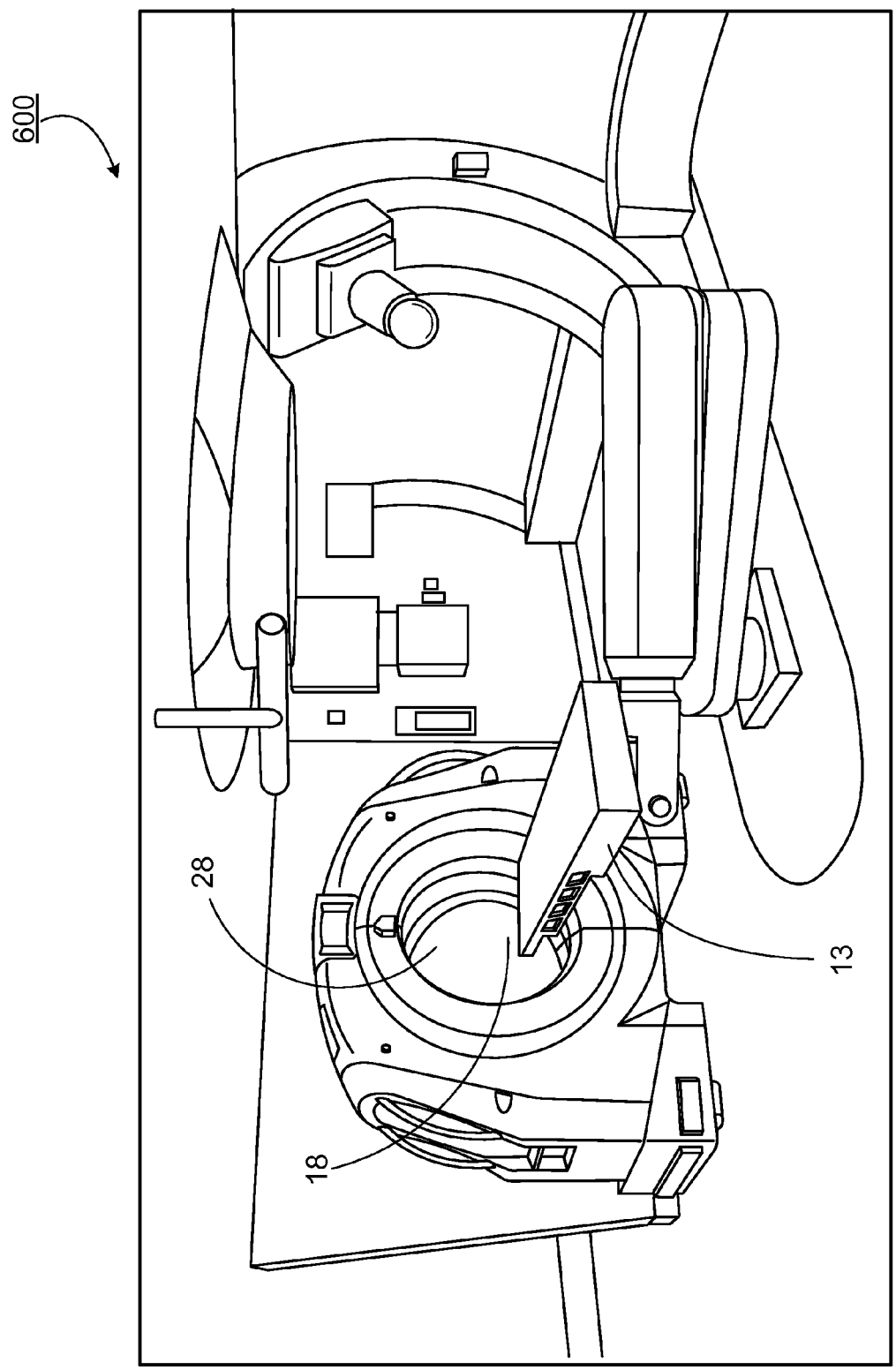
FIG. 6 is a diagram showing a perspective view of the treatment system of FIG. 1 in a configuration to capture images.

In the example of FIGS. 2 and 5, fiducials 20 may be secured directly to the treatment couch using a structure that is secured to the treatment couch. Referring to FIG. 6, treatment couch 13 is moved to the imaging position 18 by robotic arm 16. In this example, the imaging position includes opening 28 of CT scanner 21. Imaging system 14 captures (33) one or more images of the fiducials and of an irradiation target (e.g., a tumor) while the patient is on the treatment couch. The image is captured in the treatment space, e.g., the same room in which treatment by proton therapy system 15 is to be performed. The captured image(s) are stored in memory, which may be on imaging system 14, on a computer system (not shown) associated with the treatment system, or elsewhere.

In this example, the images are 3D in nature such that, either alone or in combination, the images provide information about the location of the fiducials and the location of the irradiation target in 3D space. The information may also be indicative of the relative positions of the fiducials and the irradiation target, and the angles and distances between individual fiducials and between individual fiducials and the radiation target. In some example implementations, this information is obtained (34) by identifying the fiducials and the irradiation target in the image, and by analyzing images to determine the locations of the fiducials and the size and location of the irradiation target based on the locations of the fiducials (and, in some cases, based on the size and/or shape of the fiducials). This information may be stored in memory, which may be on imaging system 14, on a computer system (not shown) associated with the treatment system, or elsewhere.

In some implementations, the treatment couch may be moved (35) from the imaging position towards the treatment position 19. For example, the treatment couch may be moved from a location near to the imaging system towards a location near to the proton therapy system. The treatment couch, however, is not yet in the treatment position, since the location of the irradiation target is not yet known to the computer system that controls the positioning of the treatment couch. Rather, the treatment couch is moved into a position where the second imaging system can detect the fiducials. In some implementations, in the imaging position, the treatment couch may already be in a position where the second imaging system can detect the fiducials; therefore, movement (35) may not be necessary. In any event, the treatment couch, in particular the portion of the treatment couch containing the fiducials, is moved into, or remains in, the field of view of the imaging apparatus in the second imaging system (which is used to detect the location of the fiducials in the real-world (3D coordinate) space.

In the example implementation shown in the figures, cameras (not shown) are used to determine (36) locations of the fiducials in the real-world treatment space. The cameras may include one or more appropriate imaging devices that are capable of capturing images of the fiducials, at least. This may be done by capturing images of the fiducials when the treatment couch is within the field of view of the cameras. The resulting images may be analyzed to determine the locations of the fiducials in the treatment space. For example, the treatment space may be part of, or define, a 3D coordinate system (e.g., an XYZ Cartesian coordinate system). The treatment space may be modeled in the computer system, with the various components of the treatment system at appropriate coordinates. Images of the fiducials taken by the cameras may be analyzed to identify where, in the 3D coordinate system, the fiducials are actually located. For example, the coordinates of the fiducials in the treatment room 3D coordinate space may be stored. This information may be stored in memory, which may be on second imaging system 14, on a computer system (not shown) associated with the treatment system, or elsewhere.

The actual locations of the fiducials in the 3D coordinate system are aligned (37) to the locations of the fiducials in the CT image. More specifically, the fiducials from the CT image are placed at the locations of the actual fiducials in the 3D coordinate system, and the other structures from the CT image are placed at appropriate locations in the 3D coordinate system relative to the fiducials. This may be done, e.g., in a virtual simulation (e.g., rendering) of the treatment space. For example, the actual locations of the fiducials may be identified in the simulation, and the fiducials from the CT image, along with other structures from the CT image, may be placed at appropriate points in the simulation. By placing the fiducials and other structures from the CT image in the 3D coordinate system, it is possible to locate the structures in the 3D coordinate system and, thus, in the real-world space of the treatment system. In addition, the local 3D coordinate system established during treatment planning is aligned to the 3D coordinate system of the real-world space, thereby facilitating detection of the location of the fiducials in the real-world space.

More specifically, the location of the fiducials in the real-world space (e.g., the 3D coordinate system) is known, and the fiducials and structures, including the irradiation target, from the CT image are mapped into the 3D coordinate system in the simulation. As part of the mapping, the fiducials from the CT image are aligned to the location of the fiducials in the real-world (3D coordinate) space. Furthermore, the location of the irradiation target relative to the fiducials in the CT image is known. For example, the distances and angles of the irradiation target relative to each fiducial are known. Given this information, it is possible to determine the location of the irradiation target in the real-world (3D coordinate) space based on the locations of the fiducials in the real-world (3D coordinate) space. Specifically, the location of the irradiation target in the real-world (3D coordinate) space is at the same distances and angles from the fiducials as the irradiation target is from the fiducials in the CT image. Accordingly, using the information from the CT image, and the locations of the fiducials in real-world space, the location of the irradiation target in real-world space can be determined. Thus, determining the location of the irradiation target relative to the treatment system includes: determining, from the CT image, a location of the irradiation target relative to locations of the fiducials in the CT image; determining locations of the fiducials relative to a reference point in the 3D coordinate space that is external to the CT image (e.g., relative to the reference coordinate system); and determining the location of the irradiation target relative to the treatment system based on the locations of the fiducials relative to the reference point (e.g., relative to the reference coordinate system) and the location of the irradiation target from the CT image. The location, as used herein, may, or may not, include the orientation of the fiducials and/or the target. In this context, the orientation includes, but is not limited to, angular position in space.

As noted above, in some implementations, the numbers of fiducials used enables a computer system to use triangulation to determine the location of the irradiation target. However, any appropriate process or processes may be used to determine the location of the irradiation target. Furthermore, the CT image models a shape of the irradiation target. The shape of the irradiation target may be regular (e.g., substantially spherical) or irregular. The fiducials may be used also to determine the shape of the irradiation target by determining locations of the surfaces of the irradiation target in the real-world (3D coordinate) space. More specifically, the distances and angles between various fiducials and irradiation target surfaces may be obtained from the CT image, and that information may be used, in the manner described above, to determine the locations of surfaces of the irradiation target in the real-world (e.g., 3D coordinate) space. This information may be provided to the computer system that controls the proton therapy system in order to control application of proton beam to the irradiation target.

In this regard, some proton therapy systems scan a proton beam across depth-wise cross-sections of an irradiation target. The shape of the irradiation target, and its location in real-world space, are used in determining where the proton beam is to be applied, both in the lateral and longitudinal directions. Some proton therapy systems scatter a proton beam across the irradiation target. In those systems, the shape of the irradiation target, and its location in real-world space, are also used in determining where the scattered proton beam is to be applied.

Figure 7:
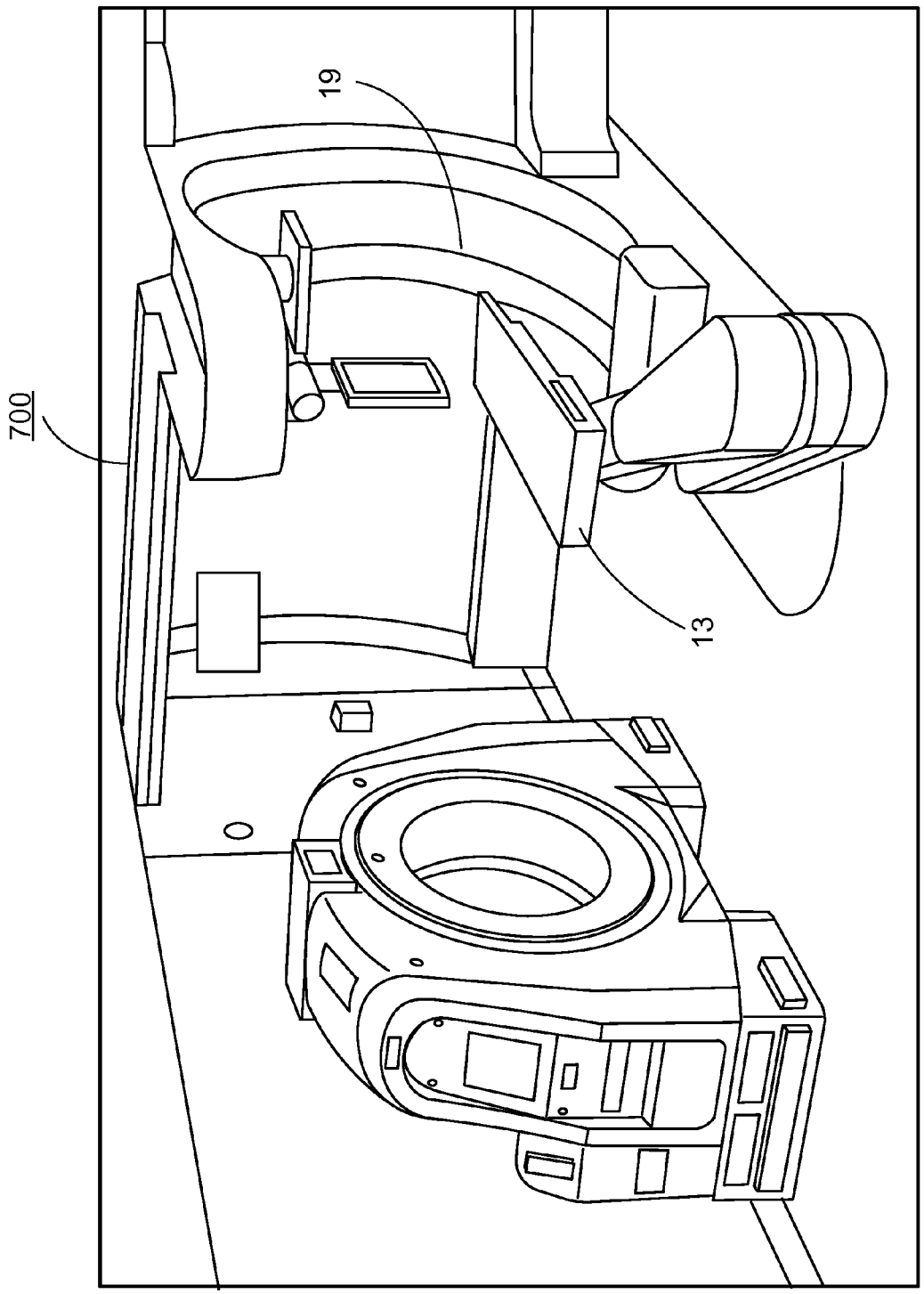
FIG. 7 is a diagram showing a perspective view of the treatment system of FIG. 1 in a configuration to perform treatment.

Referring to FIG. 7, after the location of the irradiation target in real-world space is known, it is possible to move (38) the treatment couch so that the irradiation target is in an appropriate treatment position. In some implementations, the treatment position is the isocenter of proton therapy system 15. The location of this isocenter may be predefined in the real-world (3D coordinate) space. Accordingly, to move the treatment couch, the computer system determines the difference between a current location of the irradiation target (or a point on the target) and the isocenter, and controls the movement mechanism, and thus robotic arm 16, so that the treatment couch moves the irradiation target to the treatment position. Furthermore, as part of the movement, the local 3D coordinate system established during treatment planning is aligned to the 3D coordinate system of the real-world space, thereby establishing a proper orientation of the target.

In some implementations, movement may be controlled automatically and solely by the computer system that controls the treatment system. In some implementations, movement may be triggered manually, e.g., by a technician, and subsequently controlled by the computer system either automatically or interactively.

Once the treatment couch, and thus the irradiation target in the patient, is in the treatment position, treatment (39) may be performed. In this example implementation, treatment comprises irradiating the patient with protons using proton therapy system 15. In other implementations, a different type of particle therapy system may be used. In other implementations, treatment may be performed using systems other than particle therapy systems or non-radiotherapy systems.

In some implementations, the treatment couch may be moved during treatment based on the location of the irradiation target. In other implementations, the treatment couch is not movable during treatment. In this regard, in some implementations, images are captured at different points in time, and the treatment is controlled based on the captured images. For example, the location of an irradiation target may change when the patient breathes (e.g., in response to movement of the patient's chest). The rhythm of the patient's breathing may be detected, and treatment may be controlled so as to provide proton therapy only at particular times, e.g., in between breaths.

In some implementations, the location or orientation of the irradiation target may require further system adjustment. For example, in some implementations, there may be six degrees of freedom through which the position of the treatment couch, and thus the patient, may be controlled. The six degrees typically are expressed as forward/backward motion, up/down motion, left/right motion (i.e., translation in three perpendicular axes) combined with rotation about three perpendicular axes, called yaw, pitch, and roll. Movement of the patient couch in this manner may be advantageous, e.g., in the event of patient movement. For example, if patient movement is detected, or if the irradiation target is not at the expected location, the patient couch may be adjusted accordingly.

In some implementations, the second imaging system may regularly capture images of the patient. These images may be compared to prior images to determine if the patient has moved. If movement is detected, adjustments to the patient couch, such as those described above, may be made. In this way, the system may track patient motion and make appropriate adjustments. For example, the system may determine an orientation of the irradiation target, and make appropriate rotational and/or translational adjustments to the patient couch so that the particle beam impacts the correct area(s) of the irradiation target. In another example, the system may determine that fiducials have moved over time (e.g., by comparing two images taken at different times), and then make appropriate adjustments to the patient couch so that the irradiation target is at the appropriate position for treatment—in this example, the system isocenter.

Described below is an example of a particle accelerator for use in a system, such as proton therapy system 15. The example particle therapy system includes a particle accelerator—in this example, a synchrocyclotron—mounted on a gantry. The gantry enables the accelerator to be rotated around a patient position, as explained in more detail below. In some implementations, the gantry is steel and has two legs mounted for rotation on two respective bearings that lie on opposite sides of a patient. The particle accelerator is supported by a steel truss that is long enough to span a treatment area in which the patient lies and that is attached at both ends to the rotating legs of the gantry. As a result of rotation of the gantry around the patient, the particle accelerator also rotates.

In an example implementation, the particle accelerator (e.g., the synchrocyclotron) includes a cryostat that holds one or more superconducting coils, each for conducting a current that generates a magnetic field (B). In this example, the cryostat uses liquid helium (He) to maintain each coil at superconducting temperatures, e.g., 4° Kelvin (K). Magnetic yokes or smaller magnetic pole pieces are located inside the cryostat, and define a cavity in which particles are accelerated.

In this example implementation, the particle accelerator includes a particle source (e.g., a Penning Ion Gauge—PIG source) to provide a plasma column to the cavity. Hydrogen gas is ionized to produce the plasma column. A voltage source provides a radio frequency (RF) voltage to the cavity to accelerate pulses of particles from the plasma column.

As noted, in an example, the particle accelerator is a synchrocyclotron. Accordingly, the RF voltage is swept across a range of frequencies to account for relativistic effects on the particles (e.g., increasing particle mass) when accelerating particles from the plasma column. The magnetic field produced by running current through a superconducting coil causes particles accelerated from the plasma column to accelerate orbitally within the cavity. In other implementations, a particle accelerator other than a synchrocyclotron may be used. For example, a cyclotron, a synchrotron, a linear accelerator, and so forth may be substituted for the synchrocyclotron described herein.

In the example synchrocyclotron, a magnetic field regenerator ("regenerator") is positioned near the outside of the cavity (e.g., at an interior edge thereof) to adjust the existing magnetic field inside the cavity to thereby change locations (e.g., the pitch and angle) of successive orbits of the particles accelerated from the plasma column so that, eventually, the particles output to an extraction channel that passes through the cryostat. The regenerator may increase the magnetic field at a point in the cavity (e.g., it may produce a magnetic field "bump" at an area of the cavity), thereby causing each successive orbit of particles at that point to precess outwardly toward the entry point of the extraction channel until it reaches the extraction channel. The extraction channel receives particles accelerated from the plasma column and outputs the received particles from the cavity as a particle beam.

The superconducting ("main") coils can produce relatively high magnetic fields. The magnetic field generated by a main coil may be within a range of 4 T to 20 T or more. For example, a main coil may be used to generate magnetic fields at, or that exceed, one or more of the following magnitudes: 4.0 T, 4.1 T, 4.2 T, 4.3 T, 4.4 T, 4.5 T, 4.6 T, 4.7 T, 4.8 T, 4.9 T, 5.0 T, 5.1 T, 5.2 T, 5.3 T, 5.4 T, 5.5 T, 5.6 T, 5.7 T, 5.8 T, 5.9 T, 6.0 T, 6.1 T, 6.2 T, 6.3 T, 6.4 T, 6.5 T, 6.6 T, 6.7 T, 6.8 T, 6.9 T, 7.0 T, 7.1 T, 7.2 T, 7.3 T, 7.4 T, 7.5 T, 7.6 T, 7.7 T, 7.8 T, 7.9 T, 8.0 T, 8.1 T, 8.2 T, 8.3 T, 8.4 T, 8.5 T, 8.6 T, 8.7 T, 8.8 T, 8.9 T, 9.0 T, 9.1 T, 9.2 T, 9.3 T, 9.4 T, 9.5 T, 9.6 T, 9.7 T, 9.8 T, 9.9 T, 10.0 T, 10.1 T, 10.2 T, 10.3 T, 10.4 T, 10.5 T, 10.6 T, 10.7 T, 10.8 T, 10.9 T, 11.0 T, 11.1 T, 11.2 T, 11.3 T, 11.4 T, 11.5 T, 11.6 T, 11.7 T, 11.8 T, 11.9 T, 12.0 T, 12.1 T, 12.2 T, 12.3 T, 12.4 T, 12.5 T, 12.6 T, 12.7 T, 12.8 T, 12.9 T, 13.0 T, 13.1 T, 13.2 T, 13.3 T, 13.4 T, 13.5 T, 13.6 T, 13.7 T, 13.8 T, 13.9 T, 14.0 T, 14.1 T, 14.2 T, 14.3 T, 14.4 T, 14.5 T, 14.6 T, 14.7 T, 14.8 T, 14.9 T, 15.0 T, 15.1 T, 15.2 T, 15.3 T, 15.4 T, 15.5 T, 15.6 T, 15.7 T, 15.8 T, 15.9 T, 16.0 T, 16.1 T, 16.2 T, 16.3 T, 16.4 T, 16.5 T, 16.6 T, 16.7 T, 16.8 T, 16.9 T, 17.0 T, 17.1 T, 17.2 T, 17.3 T, 17.4 T, 17.5

T, 17.6 T, 17.7 T, 17.8 T, 17.9 T, 18.0 T, 18.1 T, 18.2 T, 18.3 T, 18.4 T, 18.5 T, 18.6 T, 18.7 T, 18.8 T, 18.9 T, 19.0 T, 19.1 T, 19.2 T, 19.3 T, 19.4 T, 19.5 T, 19.6 T, 19.7 T, 19.8 T, 19.9 T, 20.0 T, 20.1 T, 20.2 T, 20.3 T, 20.4 T, 20.5 T, 20.6 T, 20.7 T, 20.8 T, 20.9 T, or more. Furthermore, a main coil may be used to generate magnetic fields that are within the range of 4 T to 20 T (or more, or less) that are not specifically listed above.

Figure 8:
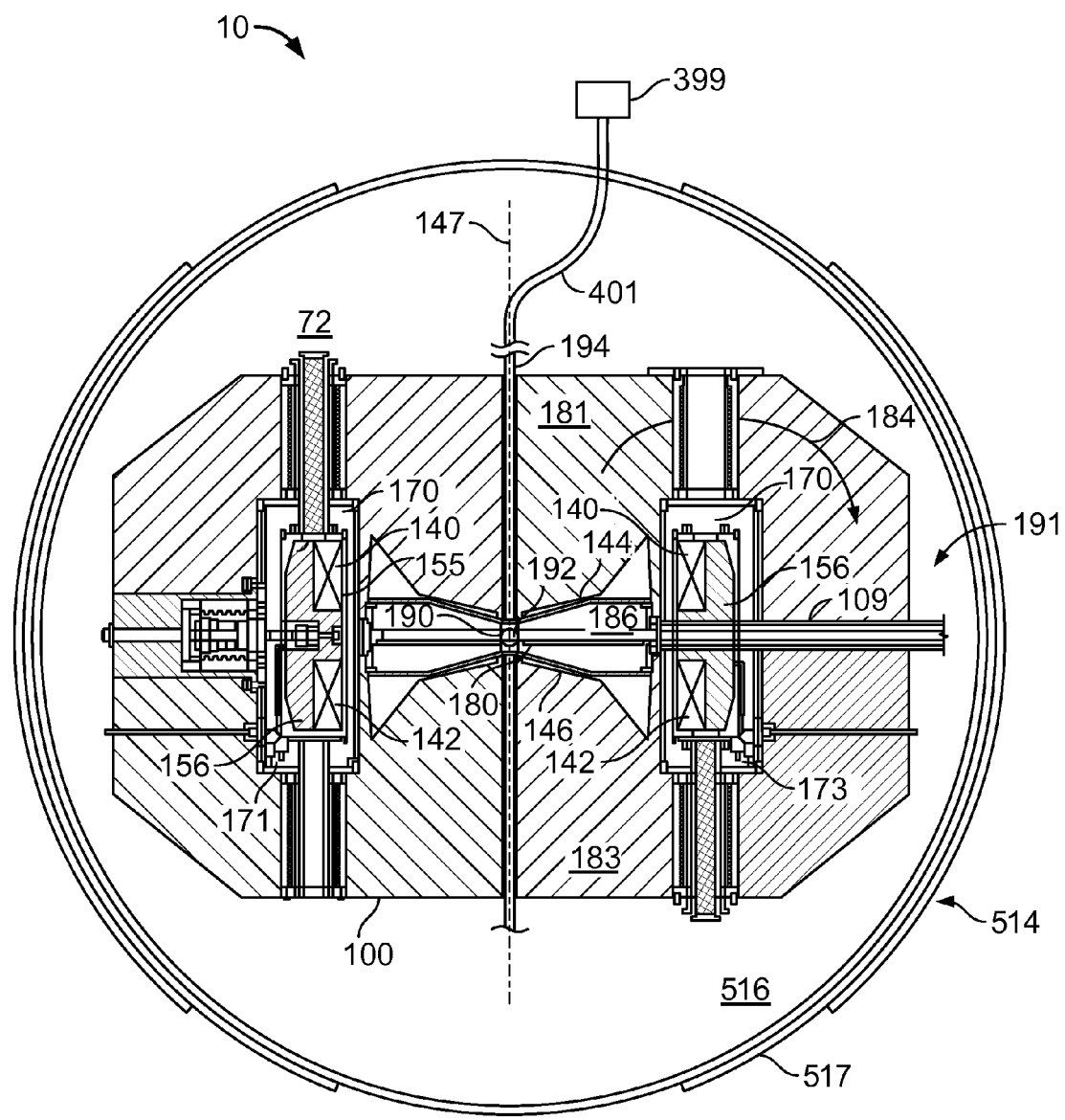
FIGS. 8 and 9 are a cross-sectional views of an example synchrocyclotron for use in a particle therapy system.
Figure 9:
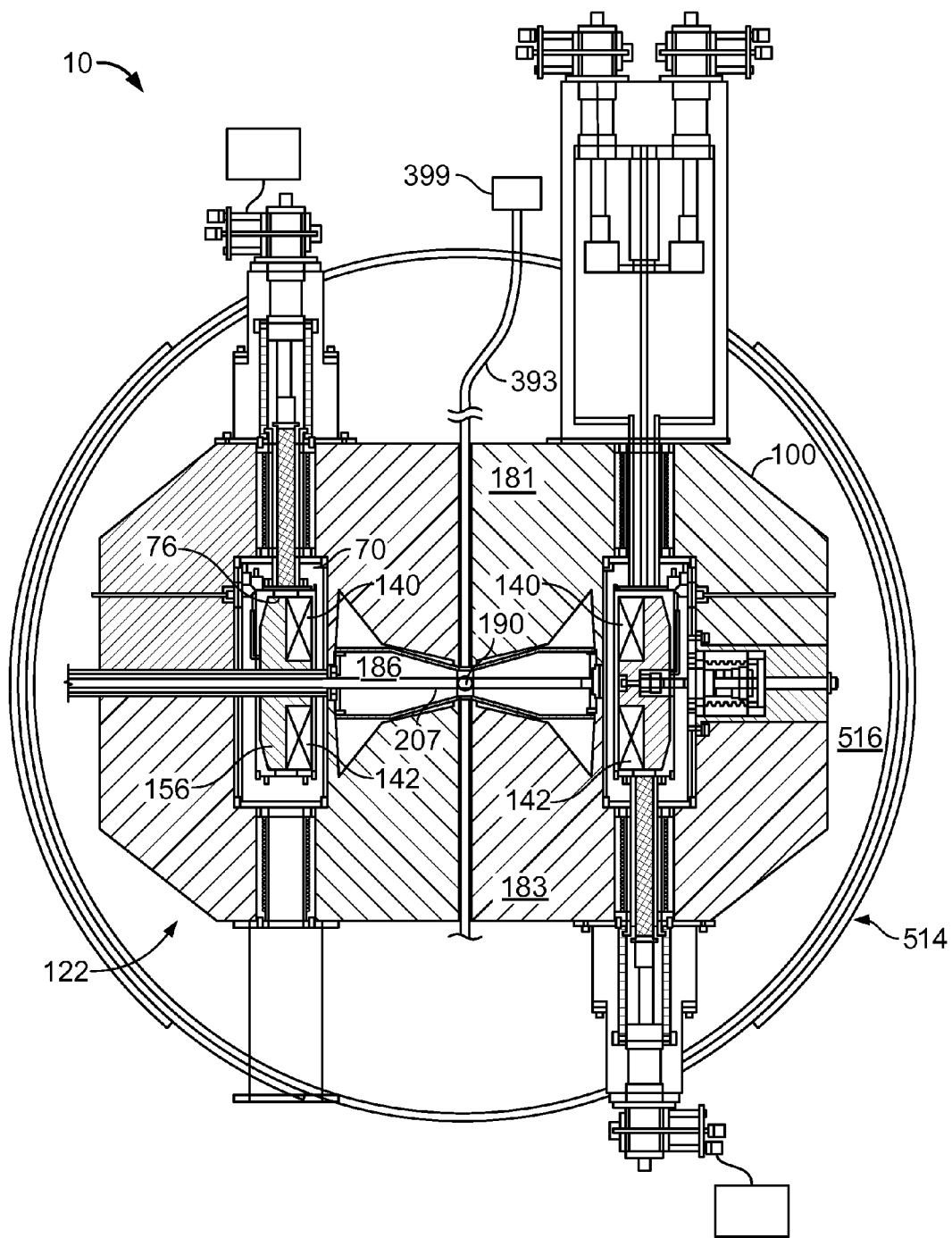

In some implementations, such as the implementation shown in FIGS. 8 and 9, large ferromagnetic magnetic yokes act as a return for stray magnetic field produced by the superconducting coils. For example, in some implementations, the superconducting magnet can generate a relatively high magnetic field of, e.g., 4 T or more, resulting in considerable stray magnetic fields. In some systems, such as that shown in FIGS. 8 and 9, the relatively large ferromagnetic return yoke 100 is used as a return for the magnetic field generated by superconducting coils. A magnetic shield surrounds the yoke. The return yoke and the shield together dissipated stray magnetic field, thereby reducing the possibility that stray magnetic fields will adversely affect the operation of the accelerator.

In some implementations, the return yoke and shield may be replaced by, or augmented by, an active return system. An example active return system includes one or more active return coils that conduct current in a direction opposite to current through the main superconducting coils. In some example implementations, there is an active return coil for each superconducting coil, e.g., two active return coils—one for each superconducting coil (referred to as a "main" coil). Each active return coil may also be a superconducting coil that surrounds the outside of a corresponding main superconducting coil.

Current passes through the active return coils in a direction that is opposite to the direction of current passing through the main coils. The current passing through the active return coils thus generates a magnetic field that is opposite in polarity to the magnetic field generated by the main coils. As a result, the magnetic field generated by an active return coil is able to dissipate at least some of the relatively strong stray magnetic field resulting from the corresponding main coil. In some implementations, each active return may be used to generate a magnetic field of between 2.5 T and 12 T or more.

Figure 10:
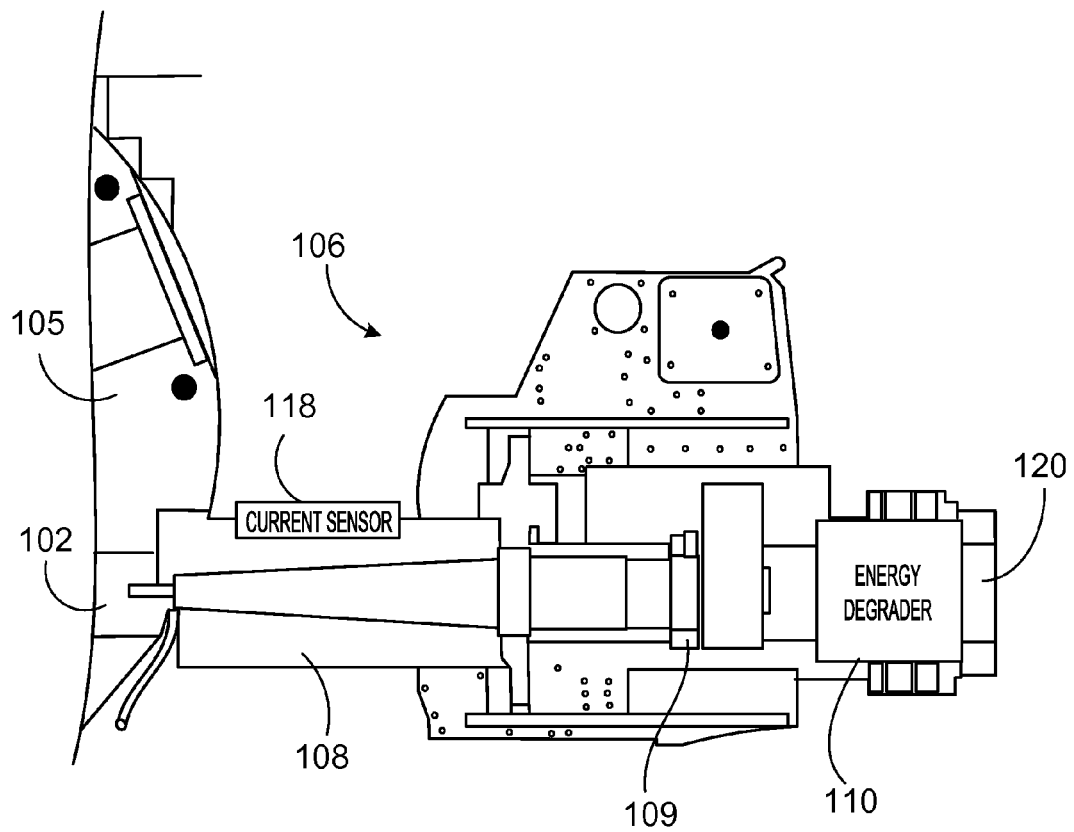
FIG. 10 is a side view of an example particle beam scanning system.
Figure 11:
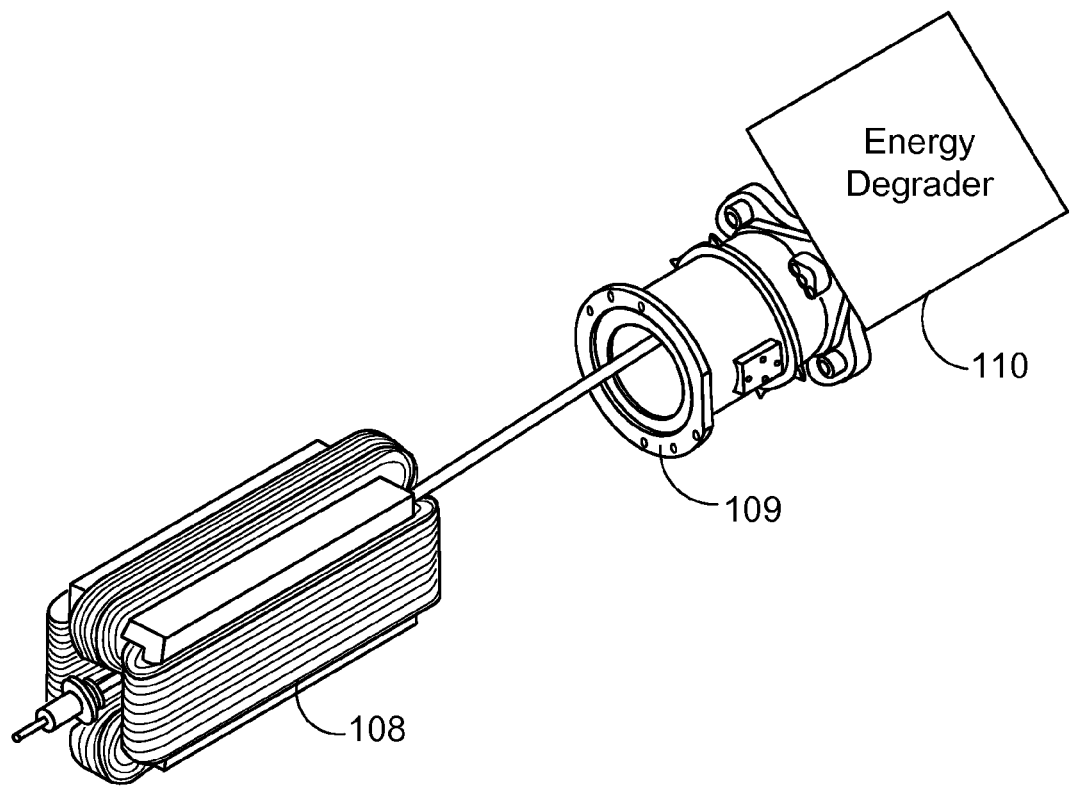
FIG. 11 is a perspective view of components of an example particle beam scanning system.

Referring to FIG. 10, at the output of extraction channel 102 of particle accelerator 105 (which may have the configuration shown in FIGS. 8 and 9), is an example scanning system 106 that may be used to scan the particle beam across at least part of an irradiation target. FIG. 11 also shows examples of components of the scanning system. These include, but are not limited to, a scanning magnet 108, an ion chamber 109, and an energy degrader 110. Other components that may be incorporated into the scanning system are not shown in FIG. 11, including, e.g., one or more scatterers for changing beam spot size.

In an example operation, scanning magnet 108 is controllable in two dimensions (e.g., Cartesian XY dimensions) to direct the particle beam across a part (e.g., a cross-section) of an irradiation target. Ion chamber 109 detects the dosage of the beam and feeds-back that information to a control system to adjust beam movement. Energy degrader 110 is controllable to move material (e.g., one or more individual plates) into, and out of, the path of the particle beam to change the energy of the particle beam and therefore the depth to which the particle beam will penetrate the irradiation target. In this way, the energy degrader selects a depth-wise layer of an irradiation target to scan in two dimensions.

In some implementations, ion chamber 109 detects dosage (e.g., one or more individual doses) applied by the particle beam to positions on an irradiation target by detecting the numbers of ion pairs created within a gas caused by incident radiation. The numbers of ion pairs correspond to the dose provided by the particle beam. That information is fed-back to the computer system and stored in memory along with the time that the dose is provided. This information may be correlated to, and stored in association with, the location at which the dose was provided and/or The processes described herein may be used with a single particle accelerator, and any two or more of the features thereof described herein may be used with the single particle accelerator. The particle accelerator may be used in any type of medical or non-medical application. An example of a particle therapy system that may be used is provided below. Notably, the concepts described herein may be used in other systems not specifically described.

Figure 12:
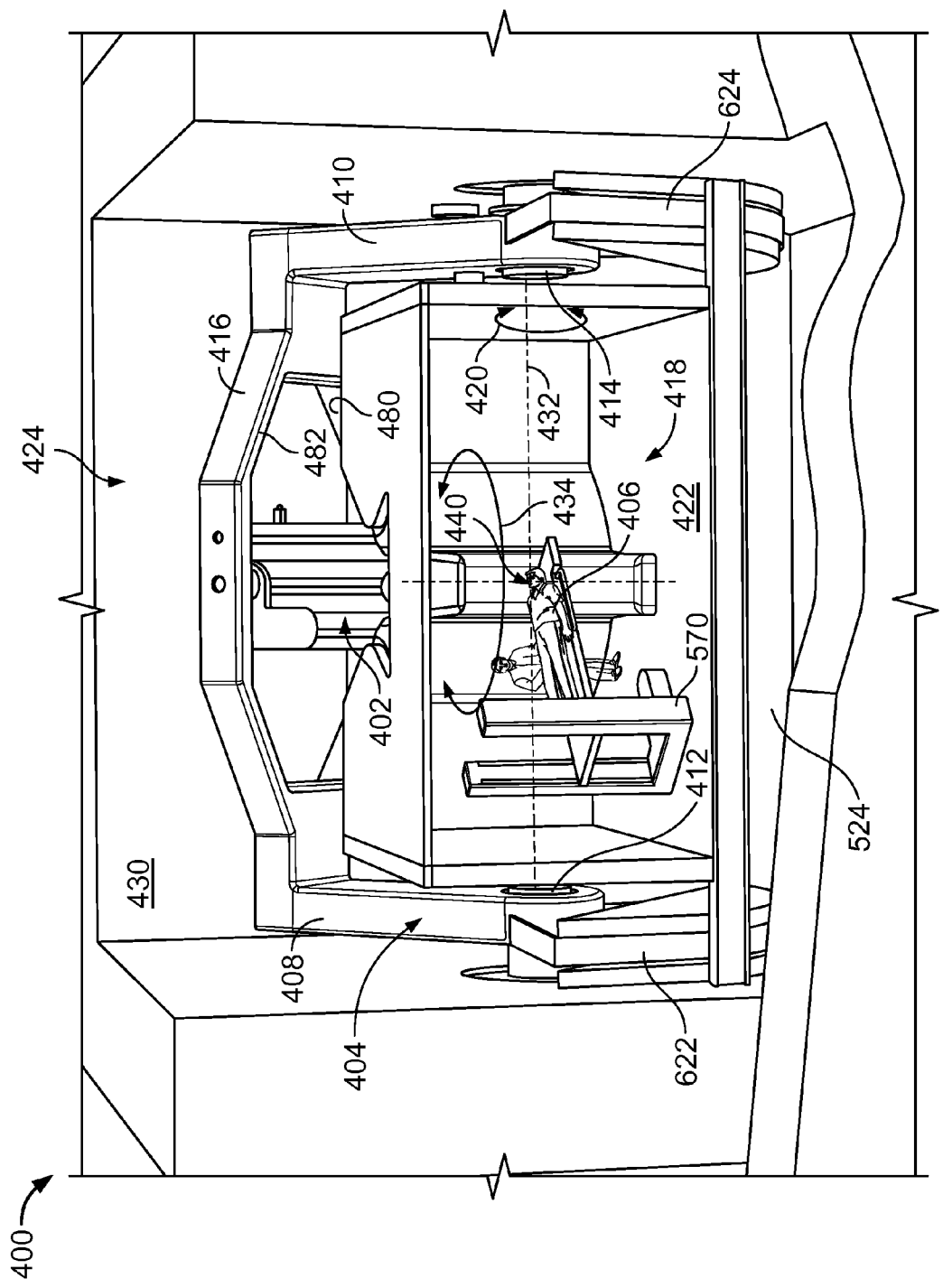
FIG. 12 is a perspective view of an example therapy system.
Figure 13:
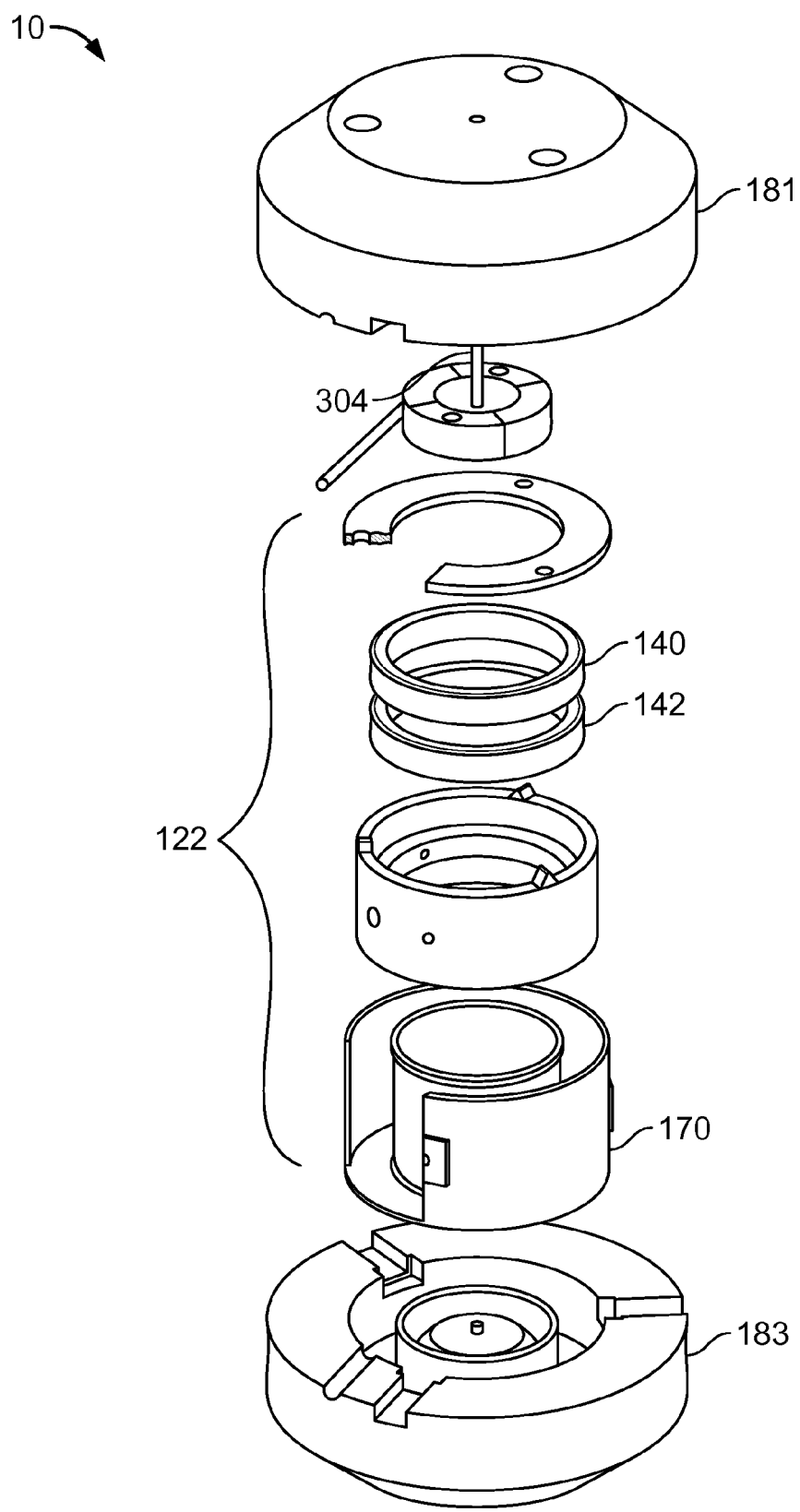
FIG. 13 is an exploded perspective view of components of an example synchrocyclotron for use in the particle therapy system.

Referring to FIG. 12, an example implementation of a charged particle radiation therapy system 400 includes a beam-producing particle accelerator 402 (e.g., the particle accelerator of FIGS. 8, 9) having a weight and size small enough to permit it to be mounted on a rotating gantry 404 with its output directed straight (that is, essentially directly) from the accelerator housing toward a patient 406. Particle accelerator 402 also includes a scanning system of a type described herein (e.g., FIGS. 10 and 11).

In some implementations, the steel gantry has two legs 408, 410 mounted for rotation on two respective bearings 412, 414 that lie on opposite sides of the patient. The accelerator is supported by a steel truss 416 that is long enough to span a treatment area 418 in which the patient lies (e.g., twice as long as a tall person, to permit the person to be rotated fully within the space with any desired target area of the patient remaining in the line of the beam) and is attached stably at both ends to the rotating legs of the gantry.

In some examples, the rotation of the gantry is limited to a range 420 of less than 360 degrees, e.g., about 180 degrees, to permit a floor 422 to extend from a wall of the vault 424 that houses the therapy system into the patient treatment area. The limited rotation range of the gantry also reduces the required thickness of some of the walls (which are not directly aligned with the beam, e.g., wall 430), which provide radiation shielding of people outside the treatment area. A range of 180 degrees of gantry rotation is enough to cover all treatment approach angles, but providing a larger range of travel can be useful. For example the range of rotation may be between 180 and 330 degrees and still provide clearance for the therapy floor space. In other implementations, rotation is not limited as described above.

The horizontal rotational axis 432 of the gantry is located nominally one meter above the floor where the patient and therapist interact with the therapy system. This floor is positioned about 3 meters above the bottom floor of the therapy system shielded vault. The accelerator can swing under the raised floor for delivery of treatment beams from below the rotational axis. The patient couch moves and rotates in a substantially horizontal plane parallel to the rotational axis of the gantry. The couch can rotate through a range 434 of about 270 degrees in the horizontal plane with this configuration. This combination of gantry and patient rotational ranges and degrees of freedom allow the therapist to select virtually any approach angle for the beam. If needed, the patient can be placed on the couch in the opposite orientation and then all possible angles can be used.

In some implementations, the accelerator uses a synchrocyclotron configuration having a high magnetic field superconducting electromagnetic structure. Because the bend radius of a charged particle of a given kinetic energy is reduced in direct proportion to an increase in the magnetic field applied to it, the high magnetic field superconducting magnetic structure permits the accelerator to be made smaller and lighter. The synchrocyclotron uses a magnetic field that is uniform in rotation angle and falls off in strength with increasing radius. Such a field shape can be achieved regardless of the magnitude of the magnetic field, so in theory there is no upper limit to the magnetic field strength (and therefore the resulting particle energy at a fixed radius) that can be used in a synchrocyclotron.

The synchrocyclotron is supported on the gantry so that the beam is generated directly in line with the patient. The gantry permits rotation of the synchrocyclotron about a horizontal rotational axis that contains a point (isocenter 440) within, or near, the patient. The split truss that is parallel to the rotational axis, supports the synchrocyclotron on both sides.

Because the rotational range of the gantry is limited in some example implementations, a patient support area can be accommodated in a wide area around the isocenter. Because the floor can be extended broadly around the isocenter, a patient support table can be positioned to move relative to and to rotate about a vertical axis 442 through the isocenter so that, by a combination of gantry rotation and table motion and rotation, any angle of beam direction into any part of the patient can be achieved. In some implementations, the two gantry arms are separated by more than twice the height of a tall patient, allowing the couch with patient to rotate and translate in a horizontal plane above the raised floor.

Limiting the gantry rotation angle allows for a reduction in the thickness of at least one of the walls surrounding the treatment room. Thick walls, typically constructed of concrete, provide radiation protection to individuals outside the treatment room. A wall downstream of a stopping proton beam may be about twice as thick as a wall at the opposite end of the room to provide an equivalent level of protection. Limiting the range of gantry rotation enables the treatment room to be sited below earth grade on three sides, while allowing an occupied area adjacent to the thinnest wall reducing the cost of constructing the treatment room.

In the example implementation shown in FIG. 12, the superconducting synchrocyclotron 402 operates with a peak magnetic field in a pole gap of the synchrocyclotron of 8.8 Tesla. The synchrocyclotron produces a beam of protons having an energy of 250 MeV. In some implementations, the synchrocyclotron is a variable-energy machine, and is capable of outputting proton beams having different energies. In some implementations, the synchrocyclotron may produce a beam having a fixed energy. In some implementations the field strength could be in the range of 4 T to 20 T and the proton energy could be in the range of 150 to 300 MeV.

The radiation therapy system described in this example is used for proton radiation therapy, but the same principles and details can be applied in analogous systems for use in heavy ion (ion) treatment systems.

As shown in FIGS. 8, 9, 12, 13, and 14, an example synchrocyclotron 10 (e.g., 402 in FIG. 12) includes a magnet system 122 that contains a particle source 190, a radiofrequency drive system 191, and a beam extraction system. In this example, the magnetic field established by the magnet system has a shape appropriate to maintain focus of a contained proton beam using a combination of a split pair of annular superconducting coils 140, 142 and a pair of shaped ferromagnetic (e.g., low carbon steel) pole faces 144, 146.

The two superconducting magnet coils are centered on a common axis and are spaced apart along the axis. The coils may be formed by of $Nb_3Sn$-based superconducting 0.8 mm diameter strands (that initially comprise a niobium-tin core surrounded by a copper sheath) deployed in a twisted cable-in-channel conductor geometry. After seven individual strands are cabled together, they are heated to cause a reaction that forms the final (brittle) superconducting material of the wire. After the material has been reacted, the wires are soldered into the copper channel (outer dimensions 3.18×2.54 mm and inner dimensions 2.08×2.08 mm) and covered with insulation (in this example, a woven fiberglass material). The copper channel containing the wires is then wound in a coil having a rectangular cross-section. The wound coil is then vacuum impregnated with an epoxy compound. The finished coils are mounted on an annular stainless steel reverse bobbin. Heater blankets may be placed at intervals in the layers of the windings to protect the assembly in the event of a magnet quench.

The entire coil can then be covered with copper sheets to provide thermal conductivity and mechanical stability and then contained in an additional layer of epoxy. The precompression of the coil can be provided by heating the stainless steel reverse bobbin and fitting the coils within the reverse bobbin. The reverse bobbin inner diameter is chosen so that when the entire mass is cooled to 4 K, the reverse bobbin stays in contact with the coil and provides some compression. Heating the stainless steel reverse bobbin to approximately 50 degrees C. and fitting coils at a temperature of 100 degrees Kelvin can achieve this.

Figure 14:
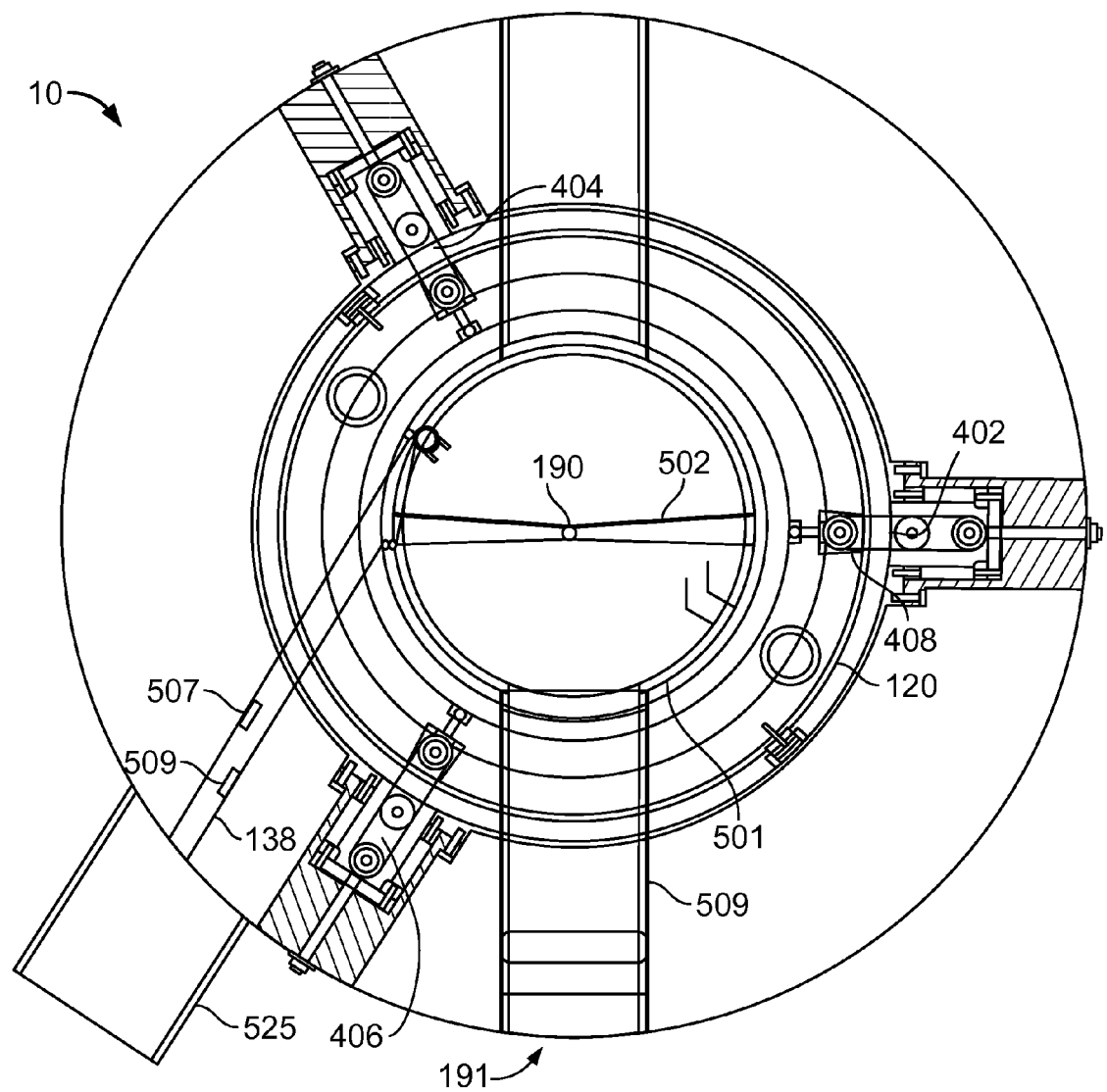
FIG. 14 is a cross-sectional view of the example synchrocyclotron.

The geometry of the coil is maintained by mounting the coils in a "reverse" rectangular bobbin to exert a restorative force that works against the distorting force produced when the coils are energized. As shown in FIG. 14, in some implementations, coil position is maintained relative to corresponding magnet pole pieces and the cryostat using a set of warm-to-cold support straps 402, 404, 406. Supporting the cold mass with thin straps reduces the heat leakage imparted to the cold mass by the rigid support system. The straps are arranged to withstand the varying gravitational force on the coil as the magnet rotates on board the gantry. They withstand the combined effects of gravity and the large de-centering force realized by the coil when it is perturbed from a perfectly symmetric position relative to the magnet yoke. Additionally, the links act to reduce dynamic forces imparted on the coil as the gantry accelerates and decelerates when its position is changed. Each warm-to-cold support may include one S2 fiberglass link and one carbon fiber link. The carbon fiber link is supported across pins between the warm yoke and an intermediate temperature (50-70 K), and the S2 fiberglass link 408 is supported across the intermediate temperature pin and a pin attached to the cold mass. Each pin may be made of high strength stainless steel.

Referring to FIG. 8, the field strength profile as a function of radius is determined largely by choice of coil geometry and pole face shape. The pole faces 144, 146 of the permeable yoke material can be contoured to fine tune the shape of the magnetic field to ensure that the particle beam remains focused during acceleration.

The superconducting coils are maintained at temperatures near absolute zero (e.g., about 4 degrees Kelvin) by enclosing the coil assembly (the coils and the bobbin) inside an evacuated annular aluminum or stainless steel cryostatic chamber 170 (the cryostat) that provides a free space around the coil structure, except at a limited set of support points 171, 173. In an alternate version (e.g., FIG. 9) the outer wall of the cryostat may be made of low carbon steel to provide an additional return flux path for the magnetic field.

In some implementations, the temperature near absolute zero is achieved and maintained using one single-stage Gifford-McMahon cryo-cooler and three two-stage Gifford McMahon cryo-coolers. Each two stage cryo-cooler has a second stage cold end attached to a condenser that recondenses Helium vapor into liquid Helium. In some implementations, the temperature near absolute zero is achieved and maintained using a cooling channel (not shown) containing liquid helium, which is formed inside a superconducting coil support structure (e.g., the reverse bobbin), and which contains a thermal connection between the liquid helium in the channel and the corresponding superconducting coil.

In some implementations, the coil assembly and cryostatic chambers are mounted within and fully enclosed by two halves 181, 183 of a pillbox-shaped magnet yoke 100. The yoke 100 provides a path for the return magnetic field flux 184 and magnetically shields the volume 186 between the pole faces 144, 146 to prevent external magnetic influences from perturbing the shape of the magnetic field within that volume. The yoke also serves to decrease the stray magnetic field in the vicinity of the accelerator. In other implementations, the coil assembly and cryostatic chambers are mounted within and fully enclosed by a non-magnetic enclosure, and the path for return magnetic field flux is implemented using an active return system, an example of which is described above.

Figure 15:
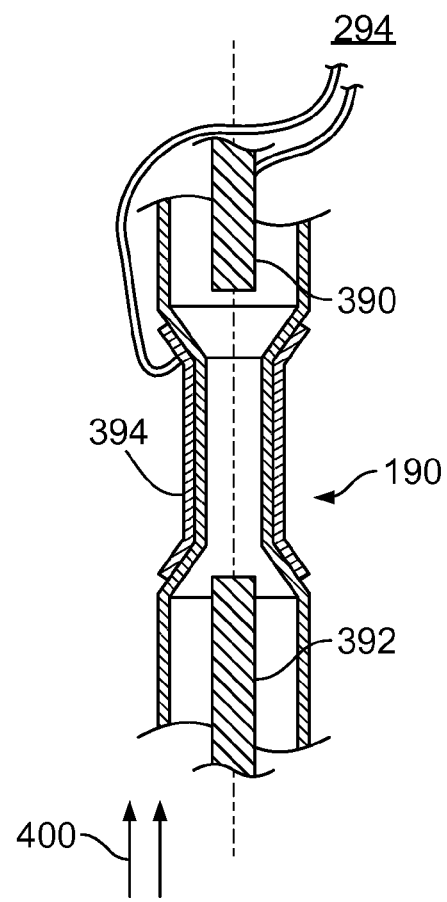
FIG. 15 is a cross-sectional view of an example ion source for use in the synchrocyclotron.

As shown in FIGS. 9, 14 and 15, the synchrocyclotron includes a particle source 190 of a Penning ion gauge geometry located near the geometric center 192 of the magnet structure. The particle source may be as described below.

Particle source 190 is fed from a supply 399 of hydrogen through a gas line 393 and tube 394 that delivers gaseous hydrogen. Electric cables 294 carry an electric current from a current source to stimulate electron discharge from cathodes 392, 390 that are aligned with the magnetic field.

In this example, the discharged electrons ionize the gas exiting through a small hole from tube 394 to create a supply of positive ions (protons) for acceleration by one semicircular (dee-shaped) radio-frequency plate that spans half of the space enclosed by the magnet structure and one dummy dee plate. Some implementations may use an interrupted particle source. In the case of an interrupted particle source all (or a substantial part, e.g., a majority) of the tube containing plasma is removed (not present) at the acceleration region.

Figure 16:
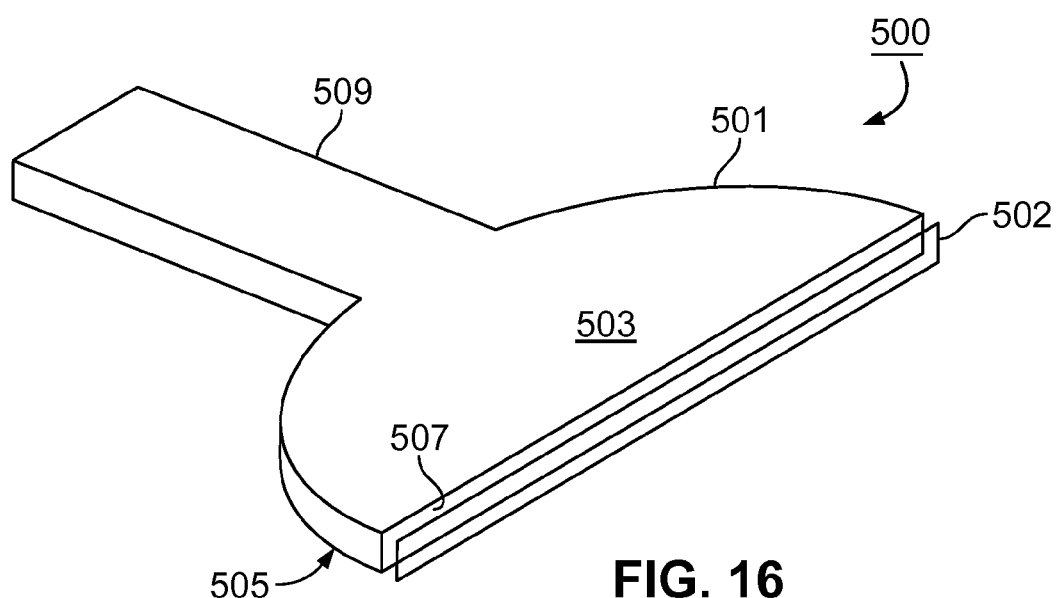
FIG. 16 is a perspective view of an example dee plate and an example dummy dee for use in the synchrocyclotron.

As shown in FIG. 16, the dee plate 500 is a hollow metal structure that has two semicircular surfaces 503, 505 that enclose a space 507 in which the protons are accelerated during half of their rotation around the space enclosed by the magnet structure. A duct 509 opening into the space 507 extends through the enclosure (e.g., the yoke or pole piece(s)) to an external location from which a vacuum pump can be attached to evacuate the space 507 and the rest of the space within a vacuum chamber in which the acceleration takes place. The dummy dee 502 comprises a rectangular metal ring that is spaced near to the exposed rim of the dee plate. The dummy dee is grounded to the vacuum chamber and magnet yoke. The dee plate 500 is driven by a radio-frequency signal that is applied at the end of a radio-frequency transmission line to impart an electric field in the space 507. The radio frequency electric field is made to vary in time as the accelerated particle beam increases in distance from the geometric center.

For the beam emerging from the centrally located particle source to clear the particle source structure as it begins to spiral outward, a large voltage difference may be applied across the radio frequency plates. 20,000 Volts is applied across the radio frequency plates. In some versions from 8,000 to 20,000 Volts may be applied across the radio frequency plates. To reduce the power required to drive this large voltage, the magnet structure is arranged to reduce the capacitance between the radio frequency plates and ground. This may be done by forming holes with sufficient clearance from the radio frequency structures through the outer yoke and the cryostat housing and making sufficient space between the magnet pole faces.

The high voltage alternating potential that drives the dee plate has a frequency that is swept downward during the accelerating cycle to account for the increasing relativistic mass of the protons and the decreasing magnetic field. The dummy dee does not require a hollow semi-cylindrical structure as it is at ground potential along with the vacuum chamber walls. Other plate arrangements could be used such as more than one pair of accelerating electrodes driven with different electrical phases or multiples of the fundamental frequency. The RF structure can be tuned to keep the Q high during the required frequency sweep by using, for example, a rotating capacitor having intermeshing rotating and stationary blades. During each meshing of the blades, the capacitance increases, thus lowering the resonant frequency of the RF structure. The blades can be shaped to create a precise frequency sweep required. A drive motor for the rotating condenser can be phase locked to the RF generator for precise control. One bunch of particles may be accelerated during each meshing of the blades of the rotating condenser.

The vacuum chamber in which the acceleration occurs is a generally cylindrical container that is thinner in the center and thicker at the rim. The vacuum chamber encloses the RF plates and the particle source and is evacuated by a vacuum pump. Maintaining a high vacuum reduces the chances that accelerating ions are not lost to collisions with gas molecules and enables the RF voltage to be kept at a higher level without arcing to ground.

Protons (or other ions) traverse a generally spiral orbital path beginning at the particle source. In half of each loop of the spiral path, the protons gain energy as they pass through the RF electric field. As the protons gain energy, the radius of the central orbit of each successive loop of their spiral path is larger than the prior loop until the loop radius reaches the maximum radius of the pole face. At that location a magnetic and electric field perturbation directs protons into an area where the magnetic field rapidly decreases, and the protons depart the area of the high magnetic field and are directed through an evacuated tube, referred to herein as the extraction channel, to exit the synchrocyclotron. A magnetic regenerator may be used to change the magnetic field perturbation to direct the protons. The protons exiting will tend to disperse as they enter an area of markedly decreased magnetic field that exists in the room around the synchrocyclotron. Beam shaping elements 507, 509 in the extraction channel 138 (FIG. 14) redirect the protons so that they stay in a straight beam of limited spatial extent.

As the beam exits the extraction channel it is passed through a beam formation system 525 (FIG. 14), which may include a scanning system of the type described herein.

Beam formation system 525 may be used in conjunction with an inner gantry that controls application of the beam.

Stray magnetic fields exiting from the synchrocyclotron may be limited by both a magnet yoke (which also serves as a shield) and a separate magnetic shield 514 (e.g., FIG. 8). The separate magnetic shield includes of a layer 517 of ferromagnetic material (e.g., steel or iron) that encloses the pillbox yoke, separated by a space 516. This configuration that includes a sandwich of a yoke, a space, and a shield achieves adequate shielding for a given leakage magnetic field at lower weight. As described above, in some implementations, an active return system may be used in place of, or to augment, the operation of the magnetic yoke and shield.

Referring to FIG. 12, the gantry allows the synchrocyclotron to be rotated about a horizontal rotational axis 432. The truss structure 416 has two generally parallel spans 480, 482. The synchrocyclotron is cradled between the spans about midway between the legs. The gantry is balanced for rotation about the bearings using counterweights 622, 624 mounted on ends of the legs opposite the truss.

The gantry is driven to rotate by an electric motor mounted to one or both of the gantry legs and connected to the bearing housings by drive gears. The rotational position of the gantry is derived from signals provided by shaft angle encoders incorporated into the gantry drive motors and the drive gears.

At the location at which the ion beam exits the synchrocyclotron, the beam formation system 525 acts on the ion beam to give it properties suitable for patient treatment. For example, the beam may be spread and its depth of penetration varied to provide uniform radiation across a given target volume. The beam formation system may include active scanning elements as described herein.

All of the active systems of the synchrocyclotron (the current driven superconducting coils, the RF-driven plates, the vacuum pumps for the vacuum acceleration chamber and for the superconducting coil cooling chamber, the current driven particle source, the hydrogen gas source, and the RF plate coolers, for example), may be controlled by appropriate synchrocyclotron control electronics (not shown), which may include, e.g., one or more processing devices executing instructions from non-transitory memory to effect control.

Figure 17:
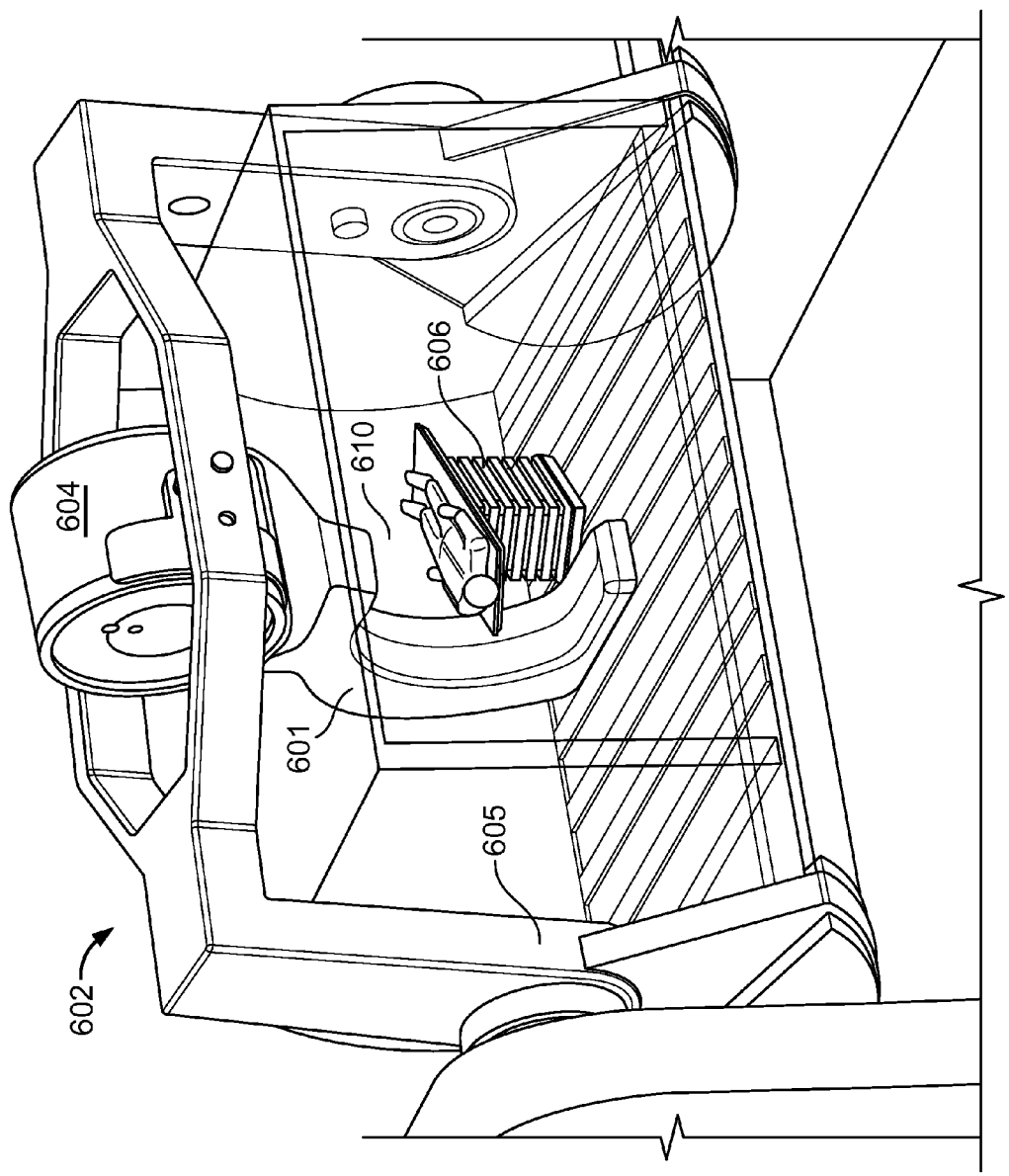
FIG. 17 shows a patient positioned within an example inner gantry of the example particle therapy system in a treatment room.

As explained above, referring to system 602 of FIG. 17, a beam-producing particle accelerator, in this case synchrocyclotron 604 (which may include any and all features described herein), may be mounted on rotating gantry 605. Rotating gantry 605 is of the type described herein, and can angularly rotate around patient support 606. This feature enables synchrocyclotron 604 to provide a particle beam essentially directly to the patient from various angles. For example, as in FIG. 17, if synchrocyclotron 604 is above patient support 606, the particle beam may be directed downwards toward the patient. Alternatively, if synchrocyclotron 604 is below patient support 606, the particle beam may be directed upwards toward the patient. The particle beam is applied essentially directly to the patient in the sense that an intermediary beam routing mechanism is not required. A routing mechanism, in this context, is different from a shaping or sizing mechanism in that a shaping or sizing mechanism does not re-route the beam, but rather sizes and/or shapes the beam while maintaining the same general trajectory of the beam.

Variable-Energy Particle Accelerator

Figure 18:
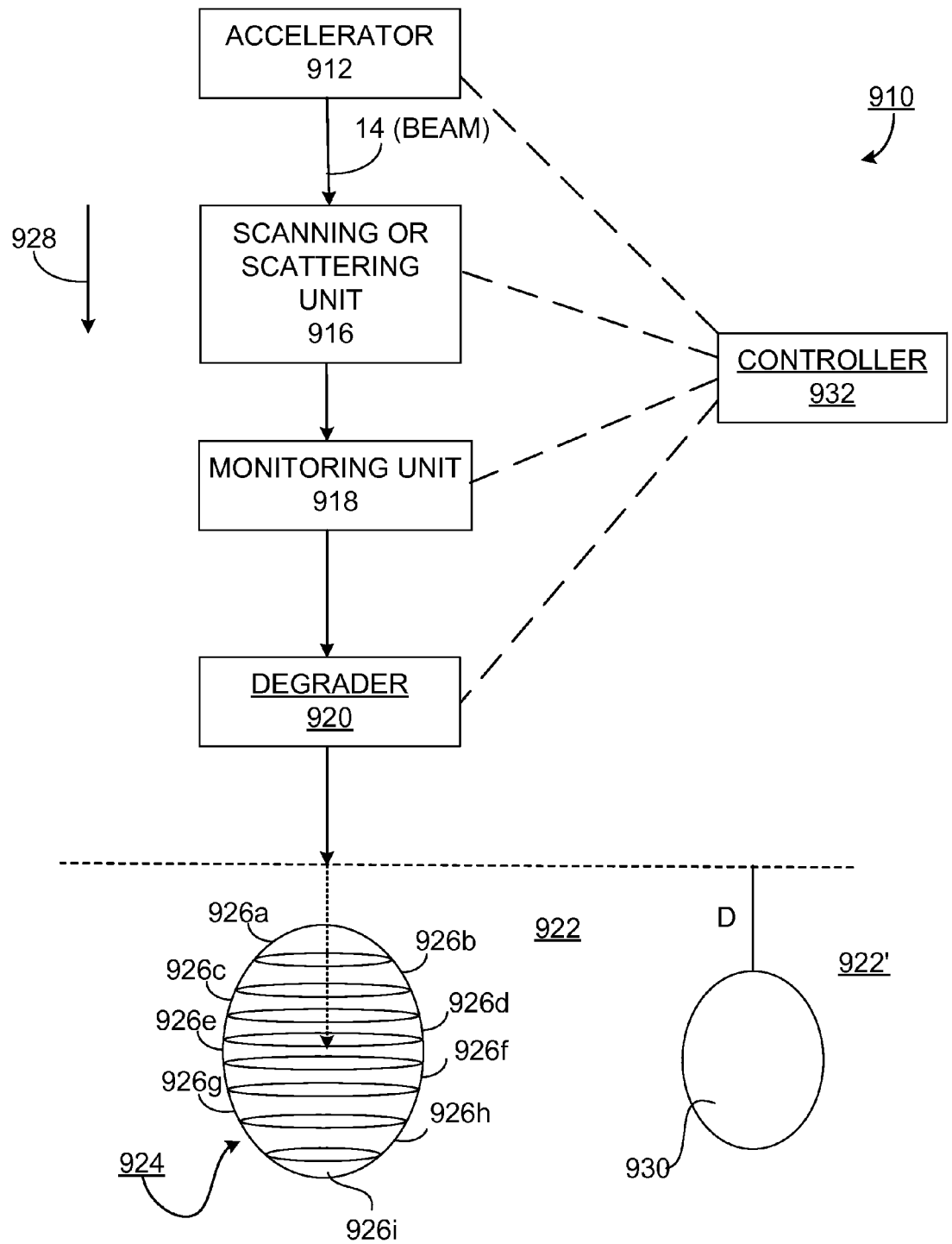
FIG. 18 is a conceptual view of an example particle therapy system that may use a variable-energy particle accelerator.

The particle accelerator used in the example particle therapy systems and example scanning systems described herein may be a variable-energy particle accelerator, an example of which is described below The energy of an extracted particle beam (the particle beam output from the accelerator) can affect the use of the particle beam during treatment. In some machines, the energy of the particle beam (or particles in the particle beam) does not increase after extraction. However, the energy may be reduced based on treatment needs after the extraction and before the treatment. Referring to FIG. 18, an example treatment system 910 includes an accelerator 912, e.g., a synchrocyclotron, from which a particle (e.g., proton) beam 914 having a variable energy is extracted to irradiate a target volume 924 of a body 922. Optionally, one or more additional devices, such as a scanning unit 916 or a scattering unit 916, one or more monitoring units 918, and an energy degrader 920, are placed along the irradiation direction 928. The devices intercept the cross-section of the extracted beam 914 and alter one or more properties of the extracted beam for the treatment.

A target volume to be irradiated (an irradiation target) by a particle beam for treatment typically has a three-dimensional configuration. In some examples, to carry-out the treatment, the target volume is divided into layers along the irradiation direction of the particle beam so that the irradiation can be done on a layer-by-layer basis. For certain types of particles, such as protons, the penetration depth (or which layer the beam reaches) within the target volume is largely determined by the energy of the particle beam. A particle beam of a given energy does not reach substantially beyond a corresponding penetration depth for that energy. To move the beam irradiation from one layer to another layer of the target volume, the energy of the particle beam is changed.

In the example shown in FIG. 18, the target volume 924 is divided into nine layers 926a-926i along the irradiation direction 928. In an example process, the irradiation starts from the deepest layer 926i, one layer at a time, gradually to the shallower layers and finishes with the shallowest layer 926a. Before application to the body 922, the energy of the particle beam 914 is controlled to be at a level to allow the particle beam to stop at a desired layer, e.g., the layer 926d, without substantially penetrating further into the body or the target volume, e.g., the layers 926e-926i or deeper into the body. In some examples, the desired energy of the particle beam 914 decreases as the treatment layer becomes shallower relative to the particle acceleration. In some examples, the beam energy difference for treating adjacent layers of the target volume 924 is about 3 MeV to about 100 MeV, e.g., about 10 MeV to about 80 MeV, although other differences may also be possible, depending on, e.g., the thickness of the layers and the properties of the beam.

The energy variation for treating different layers of the target volume 924 can be performed at the accelerator 912 (e.g., the accelerator can vary the energy) so that, in some implementations, no additional energy variation is required after the particle beam is extracted from the accelerator 912. So, the optional energy degrader 920 in the treatment system 10 may be eliminated from the system. In some implementations, the accelerator 912 can output particle beams having an energy that varies between about 100 MeV and about 300 MeV, e.g., between about 115 MeV and about 250 MeV. The variation can be continuous or non-continuous, e.g., one step at a time. In some implementations, the variation, continuous or non-continuous, can take place at a relatively high rate, e.g., up to about 50 MeV per second or up to about 20 MeV per second. Non-continuous variation can take place one step at a time with a step size of about 10 MeV to about 90 MeV.

When irradiation is complete in one layer, the accelerator 912 can vary the energy of the particle beam for irradiating a next layer, e.g., within several seconds or within less than one second. In some implementations, the treatment of the target volume 924 can be continued without substantial interruption or even without any interruption. In some situations, the step size of the non-continuous energy variation is selected to correspond to the energy difference needed for irradiating two adjacent layers of the target volume 924. For example, the step size can be the same as, or a fraction of, the energy difference.

In some implementations, the accelerator 912 and the degrader 920 collectively vary the energy of the beam 914. For example, the accelerator 912 provides a coarse adjustment and the degrader 920 provides a fine adjustment or vice versa. In this example, the accelerator 912 can output the particle beam that varies energy with a variation step of about 10-80 MeV, and the degrader 920 adjusts (e.g., reduces) the energy of the beam at a variation step of about 2-10 MeV.

The reduced use (or absence) of the energy degrader, such as a range modulator, may help to maintain properties and quality of the output beam from the accelerator, e.g., beam intensity. The control of the particle beam can be performed at the accelerator. Side effects, e.g., from neutrons generated when the particle beam passes the degrader 920 can be reduced or eliminated.

The energy of the particle beam 914 may be adjusted to treat another target volume 930 in another body or body part 922' after completing treatment in target volume 924. The target volumes 924, 930 may be in the same body (or patient), or in different patients. It is possible that the depth D of the target volume 930 from a surface of body 922' is different from that of the target volume 924. Although some energy adjustment may be performed by the degrader 920, the degrader 912 may only reduce the beam energy and not increase the beam energy.

In this regard, in some cases, the beam energy required for treating target volume 930 is greater than the beam energy required to treat target volume 924. In such cases, the accelerator 912 may increase the output beam energy after treating the target volume 924 and before treating the target volume 930. In other cases, the beam energy required for treating target volume 930 is less than the beam energy required to treat target volume 924. Although the degrader 920 can reduce the energy, the accelerator 912 can be adjusted to output a lower beam energy to reduce or eliminate the use of the degrader 920. The division of the target volumes 924, 930 into layers can be different or the same. The target volume 930 can be treated similarly on a layer by layer basis to the treatment of the target volume 924.

The treatment of the different target volumes 924, 930 on the same patient may be substantially continuous, e.g., with the stop time between the two volumes being no longer than about 30 minutes or less, e.g., 25 minutes or less, 20 minutes or less, 15 minutes or less, 10 minutes or less, 5 minutes or less, or 1 minute or less. As explained herein, the accelerator 912 can be mounted on a movable gantry and the movement of the gantry can move the accelerator to aim at different target volumes. In some situations, the accelerator 912 can complete the energy adjustment of the output beam 914 during the time the treatment system makes adjustment (such as moving the gantry) after completing the treatment of the target volume 924 and before starting treating the target volume 930. After the alignment of the accelerator and the target volume 930, the treatment can begin with the adjusted, desired beam energy. Beam energy adjustment for different patients can also be completed relatively efficiently. In some examples, all adjustments, including increasing/reducing beam energy and/or moving the gantry are done within about 30 minutes, e.g., within about 25 minutes, within about 20 minutes, within about 15 minutes, within about 10 minutes or within about 5 minutes.

In the same layer of a target volume, an irradiation dose may be applied by moving the beam across the two-dimensional surface of the layer (which is sometimes called scanning beam) using a scanning unit 916. Alternatively, the layer can be irradiated by passing the extracted beam through one or more scatterers of the scattering unit 16 (which is sometimes called scattering beam).

Beam properties, such as energy and intensity, can be selected before a treatment or can be adjusted during the treatment by controlling the accelerator 912 and/or other devices, such as the scanning unit/scatterer(s) 916, the degrader 920, and others not shown in the figures. In example implementations, system 910 includes a controller 932, such as a computer, in communication with one or more devices in the system. Control can be based on results of the monitoring performed by the one or more monitors 918, e.g., monitoring of the beam intensity, dose, beam location in the target volume, etc. Although the monitors 918 are shown to be between the device 916 and the degrader 920, one or more monitors can be placed at other appropriate locations along the beam irradiation path. Controller 932 can also store a treatment plan for one or more target volumes (for the same patient and/or different patients). The treatment plan can be determined before the treatment starts and can include parameters, such as the shape of the target volume, the number of irradiation layers, the irradiation dose for each layer, the number of times each layer is irradiated, etc. The adjustment of a beam property within the system 910 can be performed based on the treatment plan. Additional adjustment can be made during the treatment, e.g., when deviation from the treatment plan is detected.

In some implementations, the accelerator 912 is configured to vary the energy of the output particle beam by varying the magnetic field in which the particle beam is accelerated. In an example implementation, one or more sets of coils receives variable electrical current to produce a variable magnetic field in the cavity. In some examples, one set of coils receives a fixed electrical current, while one or more other sets of coils receives a variable current so that the total current received by the coil sets varies. In some implementations, all sets of coils are superconducting. In other implementations, some sets of coils, such as the set for the fixed electrical current, are superconducting, while other sets of coils, such as the one or more sets for the variable current, are non-superconducting. In some examples, all sets of coils are non-superconducting.

Generally, the magnitude of the magnetic field is scalable with the magnitude of the electrical current. Adjusting the total electric current of the coils in a predetermined range can generate a magnetic field that varies in a corresponding, predetermined range. In some examples, a continuous adjustment of the electrical current can lead to a continuous variation of the magnetic field and a continuous variation of the output beam energy. Alternatively, when the electrical current applied to the coils is adjusted in a non-continuous, step-wise manner, the magnetic field and the output beam energy also varies accordingly in a non-continuous (stepwise) manner. The scaling of the magnetic field to the current can allow the variation of the beam energy to be carried out relatively precisely, although sometimes minor adjustment other than the input current may be performed.

In some implementations, to output particle beams having a variable energy, the accelerator 912 is configured to apply RF voltages that sweep over different ranges of frequencies, with each range corresponding to a different output beam energy. For example, if the accelerator 912 is configured to produce three different output beam energies, the RF voltage is capable of sweeping over three different ranges of frequencies. In another example, corresponding to continuous beam energy variations, the RF voltage sweeps over frequency ranges that continuously change. The different frequency ranges may have different lower frequency and/or upper frequency boundaries.

The extraction channel may be configured to accommodate the range of different energies produced by the variable-energy particle accelerator. For example the extraction channel may be large enough to support the highest and lowest energies produced by the particle accelerator. That is, the extraction channel may be sized or otherwise configured to receive and to transmit particles within that range of energies. Particle beams having different energies can be extracted from the accelerator 912 without altering the features of the regenerator that is used for extracting particle beams having a single energy. In other implementations, to accommodate the variable particle energy, the regenerator can be moved to disturb (e.g., change) different particle orbits in the manner described above and/or iron rods (magnetic shims) can be added or removed to change the magnetic field bump provided by the regenerator. More specifically, different particle energies will typically be at different particle orbits within the cavity. By moving the regenerator, it is possible to intercept a particle orbit at a specified energy and thereby provide the correct perturbation of that orbit so that particles at the specified energy reach the extraction channel. In some implementations, movement of the regenerator (and/or addition/removal of magnetic shims) is performed in real-time to match real-time changes in the particle beam energy output by the accelerator. In other implementations, particle energy is adjusted on a per-treatment basis, and movement of the regenerator (and/or addition/removal of magnetic shims) is performed in advance of the treatment. In either case, movement of the regenerator (and/or addition/removal of magnetic shims) may be computer controlled. For example, a computer may control one or more motors that effect movement of the regenerator and/or magnetic shims.

In some implementations, the regenerator is implemented using one or more magnetic shims that are controllable to move to the appropriate location(s).

As an example, table 1 shows three example energy levels at which example accelerator 912 can output particle beams. The corresponding parameters for producing the three energy levels are also listed. In this regard, the magnet current refers to the total electrical current applied to the one or more coil sets in the accelerator 912; the maximum and minimum frequencies define the ranges in which the RF voltage sweeps; and "r" is the radial distance of a location to a center of the cavity in which the particles are accelerated.

TABLE 1

Examples of beam energies and respective parameters.

| Beam Energy (MeV) | Magnet Current (Amps) | Maximum Frequency (MHz) | Minimum Frequency (MHz) | Magnetic Field at r = 0 mm (Tesla) | Magnetic Field at r = 298 mm (Tesla) |
|---|---|---|---|---|---|
| 250 | 1990 | 132 | 99 | 8.7 | 8.2 |
| 235 | 1920 | 128 | 97 | 8.4 | 8.0 |
| 211 | 1760 | 120 | 93 | 7.9 | 7.5 |

Details that may be included in an example particle accelerator that produces charged particles having variable energies are described below. The accelerator can be a synchrocyclotron and the particles may be protons. The particles may be output as pulsed beams. The energy of the beam output from the particle accelerator can be varied during the treatment of one target volume in a patient, or between treatments of different target volumes of the same patient or different patients. In some implementations, settings of the accelerator are changed to vary the beam energy when no beam (or particles) is output from the accelerator. The energy variation can be continuous or non-continuous over a desired range.

Referring to the example shown in FIG. 8 (and in FIG. 12), the particle accelerator, which may be a variable-energy particle accelerator like accelerator 912 described above, may be configured to output particle beams that have a variable energy. The range of the variable energy can have an upper boundary that is about 200 MeV to about 300 MeV or higher, e.g., 200 MeV, about 205 MeV, about 210 MeV, about 215 MeV, about 220 MeV, about 225 MeV, about 230 MeV, about 235 MeV, about 240 MeV, about 245 MeV, about 250 MeV, about 255 MeV, about 260 MeV, about 265 MeV, about 270 MeV, about 275 MeV, about 280 MeV, about 285 MeV, about 290 MeV, about 295 MeV, or about 300 MeV or higher. The range can also have a lower boundary that is about 100 MeV or lower to about 200 MeV, e.g., about 100 MeV or lower, about 105 MeV, about 110 MeV, about 115 MeV, about 120 MeV, about 125 MeV, about 130 MeV, about 135 MeV, about 140 MeV, about 145 MeV, about 150 MeV, about 155 MeV, about 160 MeV, about 165 MeV, about 170 MeV, about 175 MeV, about 180 MeV, about 185 MeV, about 190 MeV, about 195 MeV, about 200 MeV.

In some examples, the variation is non-continuous and the variation step can have a size of about 10 MeV or lower, about 15 MeV, about 20 MeV, about 25 MeV, about 30 MeV, about 35 MeV, about 40 MeV, about 45 MeV, about 50 MeV, about 55 MeV, about 60 MeV, about 65 MeV, about 70 MeV, about 75 MeV, or about 80 MeV or higher. Varying the energy by one step size can take no more than 30 minutes, e.g., about 25 minutes or less, about 20 minutes or less, about 15 minutes or less, about 10 minutes or less, about 5 minutes or less, about 1 minute or less, or about 30 seconds or less. In other examples, the variation is continuous and the accelerator can adjust the energy of the particle beam at a relatively high rate, e.g., up to about 50 MeV per second, up to about 45 MeV per second, up to about 40 MeV per second, up to about 35 MeV per second, up to about 30 MeV per second, up to about 25 MeV per second, up to about 20 MeV per second, up to about 15 MeV per second, or up to about 10 MeV per second. The accelerator can be configured to adjust the particle energy both continuously and non-continuously. For example, a combination of the continuous and non-continuous variation can be used in a treatment of one target volume or in treatments of different target volumes. Flexible treatment planning and flexible treatment can be achieved.

A particle accelerator that outputs a particle beam having a variable energy can provide accuracy in irradiation treatment and reduce the number of additional devices (other than the accelerator) used for the treatment. For example, the use of degraders for changing the energy of an output particle beam may be reduced or eliminated for all or part of the treatment. The properties of the particle beam, such as intensity, focus, etc. can be controlled at the particle accelerator and the particle beam can reach the target volume without substantial disturbance from the additional devices. The relatively high variation rate of the beam energy can reduce treatment time and allow for efficient use of the treatment system.

Figure 19:
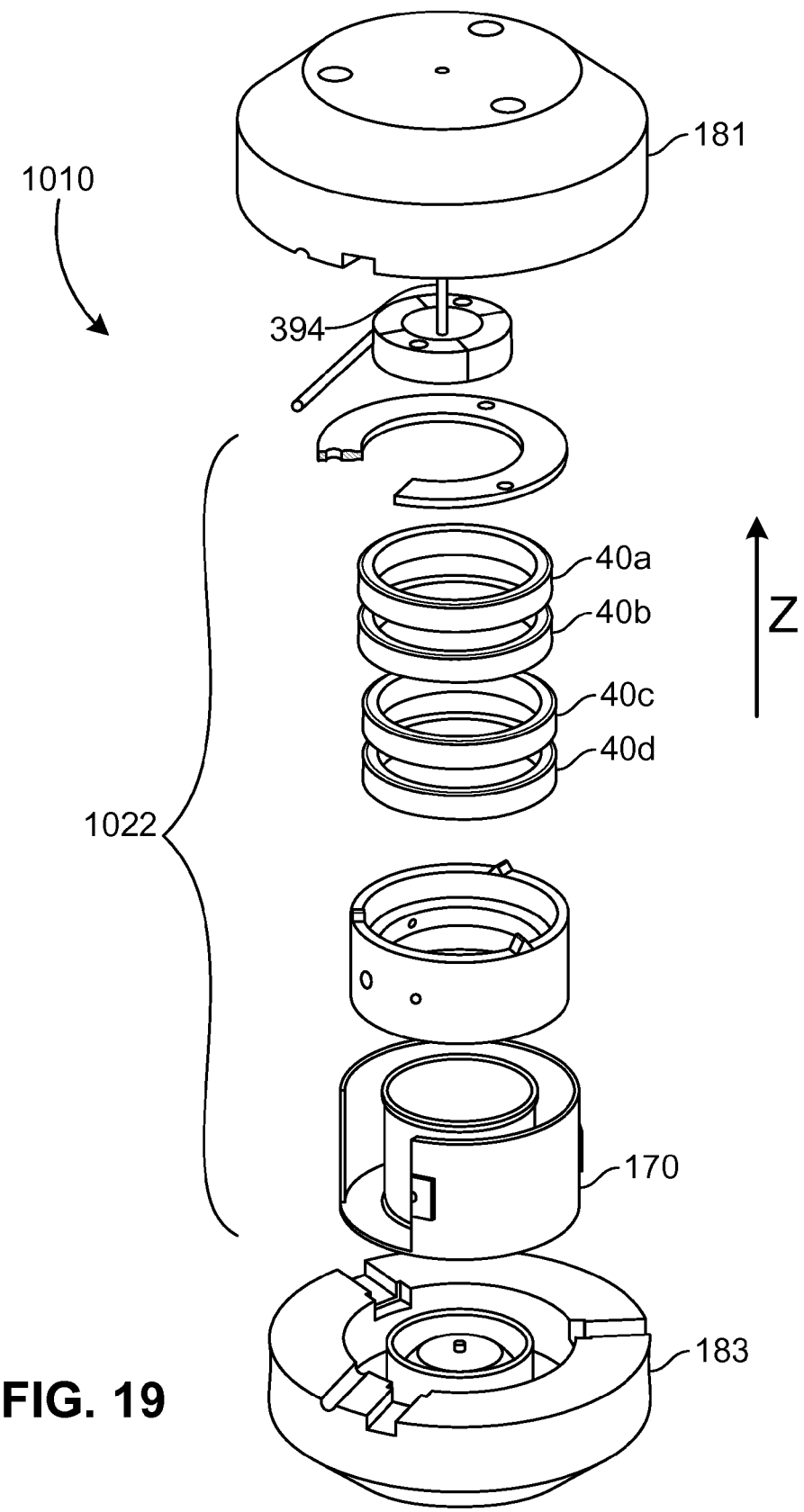
FIG. 19 is a perspective, exploded view of an example magnet system that may be used in a variable-energy particle accelerator.

In some implementations, the accelerator, such as the synchrocyclotron of FIG. 8, accelerates particles or particle beams to variable energy levels by varying the magnetic field in the accelerator, which can be achieved by varying the electrical current applied to coils for generating the magnetic field. As explained above, an example synchrocyclotron (e.g., the synchrocyclotron of FIG. 8) includes a magnet system that contains a particle source, a radiofrequency drive system, and a beam extraction system. FIG. 19 shows an example of a magnet system that may be used in a variable-energy accelerator. In this example implementation, the magnetic field established by the magnet system 1012 can vary by about 5% to about 35% of a maximum value of the magnetic field that two sets of coils 40a and 40b, and 42a and 42b are capable of generating. The magnetic field established by the magnet system has a shape appropriate to maintain focus of a contained proton beam using a combination of the two sets of coils and a pair of shaped ferromagnetic (e.g., low carbon steel) structures, examples of which are provided above.

Each set of coils may be a split pair of annular coils to receive electrical current. In some situations, both sets of coils are superconducting. In other situations, only one set of the coils is superconducting and the other set is non-superconducting or normal conducting (also discussed further below). It is also possible that both sets of coils are non-superconducting. Suitable superconducting materials for use in the coils include niobium-3 tin (Nb3Sn) and/or niobium-titanium. Other normal conducting materials can include copper. Examples of the coil set constructions are described further below.

The two sets of coils can be electrically connected serially or in parallel. In some implementations, the total electrical current received by the two sets of coils can include about 2 million ampere turns to about 10 million ampere turns, e.g., about 2.5 to about 7.5 million ampere turns or about 3.75 million ampere turns to about 5 million ampere turns. In some examples, one set of coils is configured to receive a fixed (or constant) portion of the total variable electrical current, while the other set of coils is configured to receive a variable portion of the total electrical current. The total electrical current of the two coil sets varies with the variation of the current in one coil set. In other situations, the electrical current applied to both sets of coils can vary. The variable total current in the two sets of coils can generate a magnetic field having a variable magnitude, which in turn varies the acceleration pathways of the particles and produces particles having variable energies.

Generally, the magnitude of the magnetic field generated by the coil(s) is scalable to the magnitude of the total electrical current applied to the coil(s). Based on the scalability, in some implementations, linear variation of the magnetic field strength can be achieved by linearly changing the total current of the coil sets. The total current can be adjusted at a relatively high rate that leads to a relatively high-rate adjustment of the magnetic field and the beam energy.

In the example reflected in Table 1 above, the ratio between values of the current and the magnetic field at the geometric center of the coil rings is: 1990:8.7 (approximately 228.7:1); 1920:8.4 (approximately 228.6:1); 1760:7.9 (approximately 222.8:1). Accordingly, adjusting the magnitude of the total current applied to a superconducting coil(s) can proportionally (based on the ratio) adjust the magnitude of the magnetic field.

Figure 20:
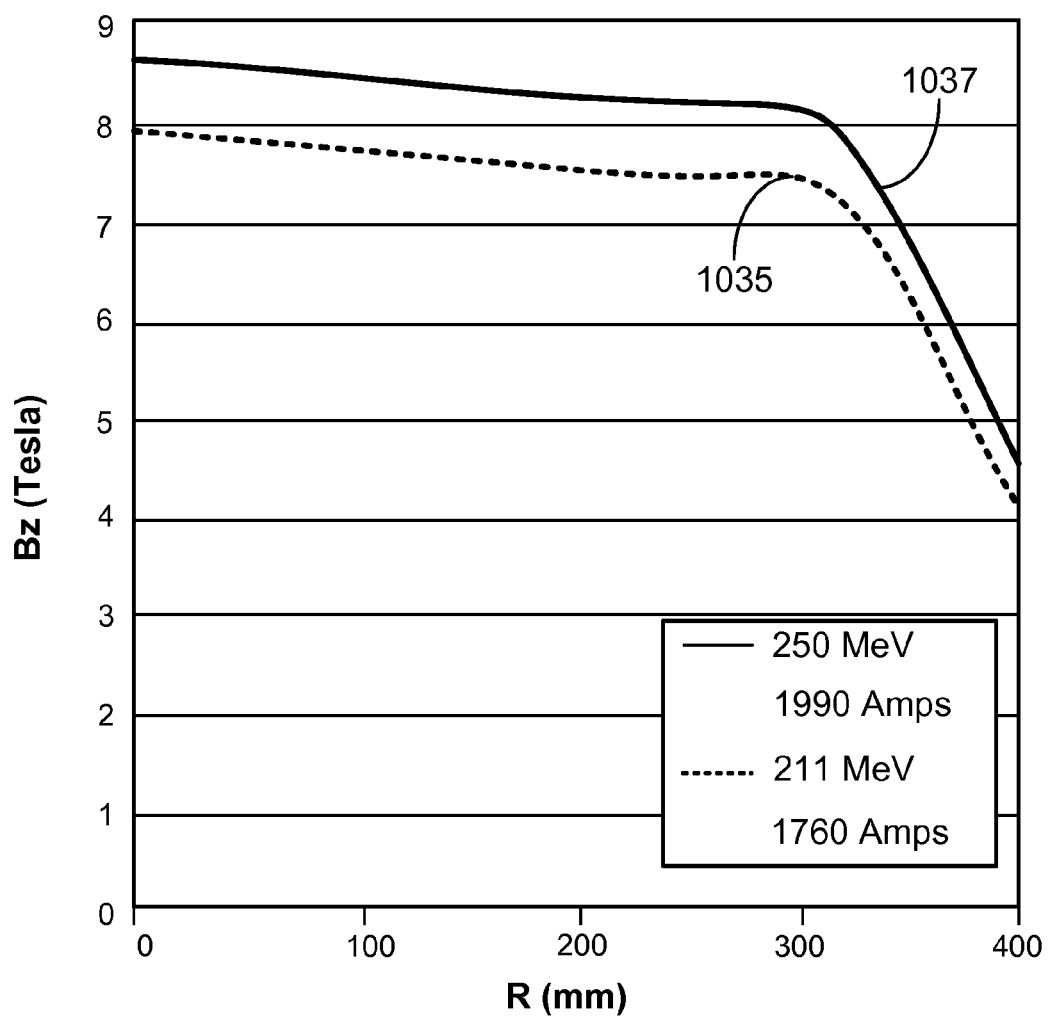
FIG. 20 is an example graph showing energy and current for variations in magnetic field and distance in a particle accelerator.

The scalability of the magnetic field to the total electrical current in the example of Table 1 is also shown in the plot of FIG. 20, where BZ is the magnetic field along the Z direction; and R is the radial distance measured from a geometric center of the coil rings along a direction perpendicular to the Z direction. The magnetic field has the highest value at the geometric center, and decreases as the distance R increases. The curves 1035, 1037 represent the magnetic field generated by the same coil sets receiving different total electrical current: 1760 Amperes and 1990 Amperes, respectively. The corresponding energies of the extracted particles are 211 MeV and 250 MeV, respectively. The two curves 1035, 1037 have substantially the same shape and the different parts of the curves 1035, 1037 are substantially parallel. As a result, either the curve 1035 or the curve 1037 can be linearly shifted to substantially match the other curve, indicating that the magnetic field is scalable to the total electrical current applied to the coil sets.

In some implementations, the scalability of the magnetic field to the total electrical current may not be perfect. For example, the ratio between the magnetic field and the current calculated based on the example shown in table 1 is not constant. Also, as shown in FIG. 20, the linear shift of one curve may not perfectly match the other curve. In some implementations, the total current is applied to the coil sets under the assumption of perfect scalability. The target magnetic field (under the assumption of perfect scalability) can be generated by additionally altering the features, e.g., geometry, of the coils to counteract the imperfection in the scalability. As one example, ferromagnetic (e.g., iron) rods (magnetic shims) can be inserted or removed from one or both of the magnetic structures (e.g., yokes, pole pieces, and the like). The features of the coils can be altered at a relatively high rate so that the rate of the magnetic field adjustment is not substantially affected as compared to the situation in which the scalability is perfect and only the electrical current needs to be adjusted. In the example of iron rods, the rods can be added or removed at the time scale of seconds or minutes, e.g., within 5 minutes, within 1 minute, less than 30 seconds, or less than 1 second.

In some implementations, settings of the accelerator, such as the current applied to the coil sets, can be chosen based on the substantial scalability of the magnetic field to the total electrical current in the coil sets.

Generally, to produce the total current that varies within a desired range, any appropriate combination of current applied to the two coil sets can be used. In an example, the coil set 42a, 42b can be configured to receive a fixed electrical current corresponding to a lower boundary of a desired range of the magnetic field. In the example shown in table 1, the fixed electrical current is 1760 Amperes. In addition, the coil set 40a, 40b can be configured to receive a variable electrical current having an upper boundary corresponding to a difference between an upper boundary and a lower boundary of the desired range of the magnetic field. In the example shown in table 1, the coil set 40a, 40b is configured to receive electrical current that varies between 0 Ampere and 230 Amperes.

In another example, the coil set 42a, 42b can be configured to receive a fixed electrical current corresponding to an upper boundary of a desired range of the magnetic field. In the example shown in table 1, the fixed current is 1990 Amperes. In addition, the coil set 40a, 40b can be configured to receive a variable electrical current having an upper boundary corresponding to a difference between a lower boundary and an upper boundary of the desired range of the magnetic field. In the example shown in table 1, the coil set 40a, 40b is configured to receive electrical current that varies between −230 Ampere and 0 Ampere.

The total variable magnetic field generated by the variable total current for accelerating the particles can have a maximum magnitude greater than 4 Tesla, e.g., greater than 5 Tesla, greater than 6 Tesla, greater than 7 Tesla, greater than 8 Tesla, greater than 9 Tesla, or greater than 10 Tesla, and up to about 20 Tesla or higher, e.g., up to about 18 Tesla, up to about 15 Tesla, or up to about 12 Tesla. In some implementations, variation of the total current in the coil sets can vary the magnetic field by about 0.2 Tesla to about 4.2 Tesla or more, e.g., about 0.2 Tesla to about 1.4 Tesla or about 0.6 Tesla to about 4.2 Tesla. In some situations, the amount of variation of the magnetic field can be proportional to the maximum magnitude.

Figure 21:
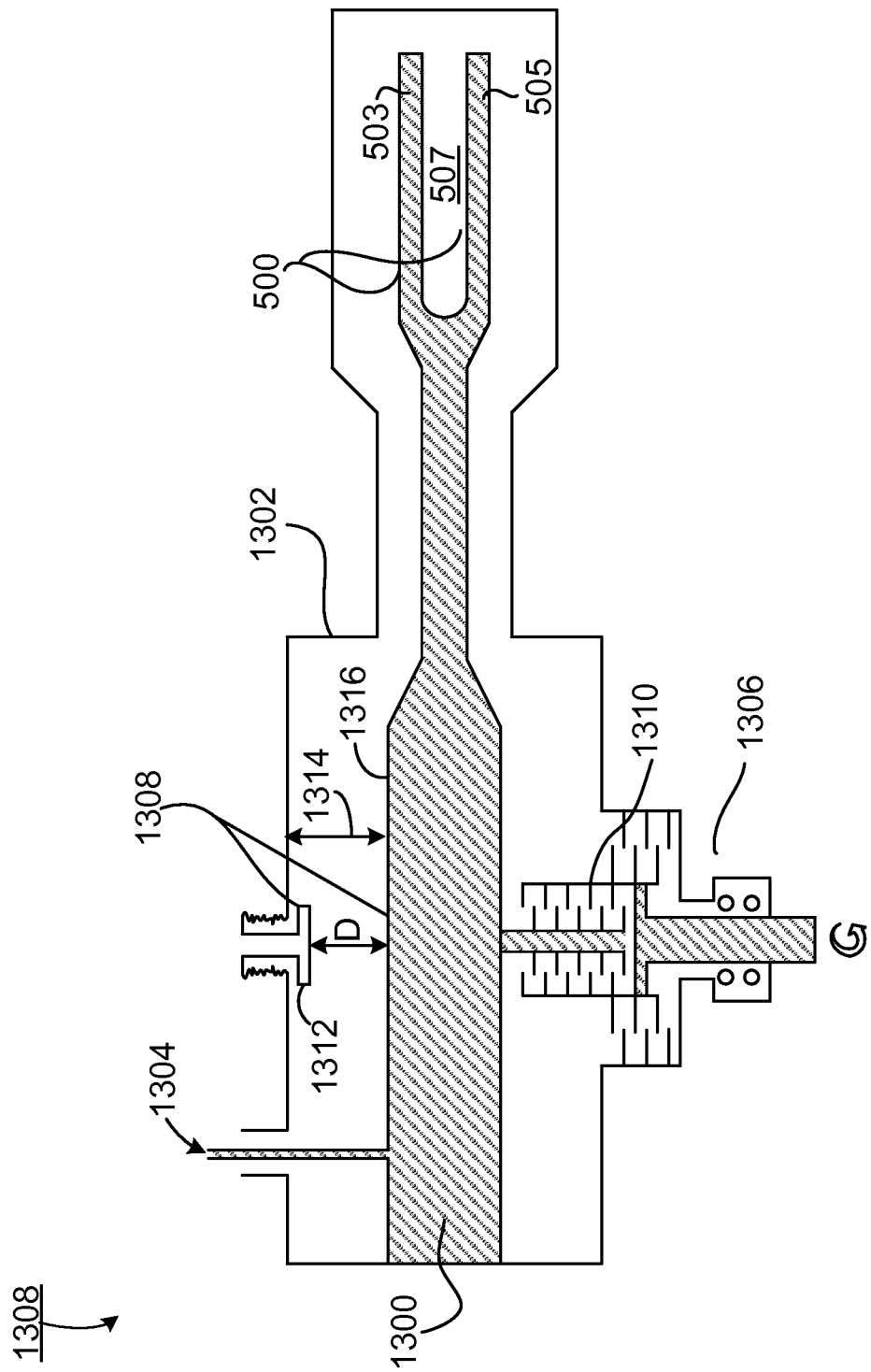
FIG. 21 is a side view of an example structure for sweeping voltage on a dee plate over a frequency range for each energy level of a particle beam, and for varying the frequency range when the particle beam energy is varied.

FIG. 21 shows an example RF structure for sweeping the voltage on the dee plate 500 over an RF frequency range for each energy level of the particle beam, and for varying the frequency range when the particle beam energy is varied. The semicircular surfaces 503, 505 of the dee plate 500 are connected to an inner conductor 1300 and housed in an outer conductor 1302. The high voltage is applied to the dee plate 500 from a power source (not shown, e.g., an oscillating voltage input) through a power coupling device 1304 that couples the power source to the inner conductor. In some implementations, the coupling device 1304 is positioned on the inner conductor 1300 to provide power transfer from the power source to the dee plate 500. In addition, the dee plate 500 is coupled to variable reactive elements 1306, 1308 to perform the RF frequency sweep for each particle energy level, and to change the RF frequency range for different particle energy levels.

The variable reactive element 1306 can be a rotating capacitor that has multiple blades 1310 rotatable by a motor (not shown). By meshing or unmeshing the blades 1310 during each cycle of RF sweeping, the capacitance of the RF structure changes, which in turn changes the resonant frequency of the RF structure. In some implementations, during each quarter cycle of the motor, the blades 1310 mesh with the each other. The capacitance of the RF structure increases and the resonant frequency decreases. The process reverses as the blades 1310 unmesh. As a result, the power required to generate the high voltage applied to the dee plate 103 and necessary to accelerate the beam can be reduced by a large factor. In some implementations, the shape of the blades 1310 is machined to form the required dependence of resonant frequency on time.

The RF frequency generation is synchronized with the blade rotation by sensing the phase of the RF voltage in the resonator, keeping the alternating voltage on the dee plates close to the resonant frequency of the RF cavity. (The dummy dee is grounded and is not shown in FIG. 21).

The variable reactive element 1308 can be a capacitor formed by a plate 1312 and a surface 1316 of the inner conductor 1300. The plate 1312 is movable along a direction 1314 towards or away from the surface 1316. The capacitance of the capacitor changes as the distance D between the plate 1312 and the surface 1316 changes. For each frequency range to be swept for one particle energy, the distance D is at a set value, and to change the frequency range, the plate 1312 is moved corresponding to the change in the energy of the output beam.

In some implementations, the inner and outer conductors 1300, 1302 are formed of a metallic material, such as copper, aluminum, or silver. The blades 1310 and the plate 1312 can also be formed of the same or different metallic materials as the conductors 1300, 1302. The coupling device 1304 can be an electrical conductor. The variable reactive elements 1306, 1308 can have other forms and can couple to the dee plate 100 in other ways to perform the RF frequency sweep and the frequency range alteration. In some implementations, a single variable reactive element can be configured to perform the functions of both the variable reactive elements 1306, 1308. In other implementations, more than two variable reactive elements can be used.

The control of the gantry, the patient support, the active beam shaping elements, and the synchrocyclotron to perform a therapy session is achieved by appropriate therapy control electronics (not shown).

Control of the particle therapy system described herein and its various features may be implemented using hardware or a combination of hardware and software. For example, a system like the ones described herein may include various controllers and/or processing devices located at various points. A central computer may coordinate operation among the various controllers or processing devices. The central computer, controllers, and processing devices may execute various software routines to effect control and coordination of testing and calibration.

System operation can be controlled, at least in part, using one or more computer program products, e.g., one or more computer program tangibly embodied in one or more non-transitory machine-readable media, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the operations of the particle therapy system described herein can be performed by one or more programmable processors executing one or more computer programs to perform the functions described herein. All or part of the operations can be implemented using special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass PCBs for storing data, e.g., magnetic, magneto-optical disks, or optical disks. Non-transitory machine-readable storage media suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks.

Any "electrical connection" as used herein may imply a direct physical connection or a connection that includes intervening components but that nevertheless allows electrical signals to flow between connected components. Any "connection" involving electrical circuitry mentioned herein, unless stated otherwise, is an electrical connection and not necessarily a direct physical connection regardless of whether the word "electrical" is used to modify "connection".

Any two more of the foregoing implementations may be used in an appropriate combination in an appropriate particle accelerator (e.g., a synchrocyclotron). Likewise, individual features of any two more of the foregoing implementations may be used in an appropriate combination.

Elements of different implementations described herein may be combined to form other implementations not specifically set forth above. Elements may be left out of the processes, systems, apparatus, etc., described herein without adversely affecting their operation. Various separate elements may be combined into one or more individual elements to perform the functions described herein.

The example implementations described herein are not limited to use with a particle therapy system or to use with the example particle therapy systems described herein. Rather, the example implementations can be used in any appropriate system that directs accelerated particles to an output.

Other implementations not specifically described herein are also within the scope of the following claims.

What is claimed is:

1. A method of positioning a patient for treatment using a particle therapy system, comprising:
    associating fiducials with the patient;
    using a first imaging system located at an imaging position to capture a first image of the fiducials and of an irradiation target while the patient is on a treatment couch, the imaging position being in a treatment room where treatment using the particle therapy system is to be performed;
    moving the treatment couch while the patient is on the treatment couch from the imaging position toward a treatment position at which the treatment using the particle therapy system is to be performed, the treatment position being different from the imaging position and being in the treatment room;
    following movement of the treatment couch, using a second imaging system to capture a second image of the fiducials in the treatment room while the patient is on the treatment couch;
    determining locations of the fiducials in the treatment room based on both the first image and the second image;
    determining a location of the irradiation target relative to the particle therapy system based on locations of the fiducials in the treatment room and in the first image; and
    moving the treatment couch into the treatment position in the treatment room based on the location of the irradiation target;
    wherein the patient remains on the treatment couch during capturing the first image, through moving the treatment couch toward the treatment position, through capturing the second image, and through moving the treatment couch into the treatment position.

2. The method of claim 1, wherein the first imaging system is configured to capture internal images of the patient and of the fiducials; and
    wherein the second imaging system is configured to capture external images of the fiducials.

3. The method of claim 1, wherein the first image comprises one or more of the following: an X-ray radiograph image, a computed tomography (CT) image that is captured by a CT imaging device, a magnetic resonance imaging (MRI) image that is captured by an MRI imaging device, a positron emission tomography (PET) image that is captured by a PET device, an image captured by a video surface imaging device, or an image captured by a SPECT/CT device.

4. The method of claim 1, further comprising:
    treating the patient at the treatment position;
    wherein treating the patient comprising irradiating the patient with protons using the particle therapy system.

5. The method of claim 4, wherein the particle therapy system has an isocenter, the isocenter comprising the treatment position.

6. The method of claim 1, wherein the location of the irradiation target relative to the particle therapy system is determined based on a reference coordinate system of the treatment room.

7. The method of claim, wherein the particle therapy system has an isocenter; and
    wherein moving the treatment couch into the treatment position comprises moving the treatment couch so that the location of the irradiation target corresponds to the a location of the isocenter.

8. The method of claim 1, wherein associating fiducials with the patient comprises:
    securing the patient to the treatment couch relative to the fiducials; or
    securing the fiducials relative to the patient.

9. The method of claim 1, wherein moving the treatment couch into the treatment position is performed using a robotic mechanism that moves the treatment couch automatically from the imaging position to the treatment position while the patient remains on the treatment couch.

10. The method of claim 1, wherein moving the treatment couch is performed manually while the patient remains on the treatment couch.

11. The method of claim 1, wherein associating fiducials with the patient comprises arranging fiducials on the patient.

12. The method of claim 1, wherein associating fiducials with the patient comprises identifying anatomical landmarks on the patient, and designating the anatomical landmarks to be the fiducials.

13. The method of claim 1, wherein associating fiducials with the patient comprises arranging a frame over at least part of the patient, and securing the fiducials to the frame.

14. The method of claim 1, wherein the first image comprises a three-dimensional (3D) image or a two-dimensional (2D) image.

15. The method of claim 1, further comprising:
determining an orientation of the irradiation target based on locations of the fiducials in the treatment room and in the first image; and
orienting the treatment based on the orientation of the irradiation target.

16. The method of claim 1, further comprising:
tracking movement of the fiducials over time; and
controlling movement of the treatment couch based on movement of the fiducials.

17. The method of claim 1, further comprising:
tracking movement of the fiducials over time; and
controlling treatment based on movement of the fiducials.

18. The method of claim 1, wherein capturing the first image comprises capturing the first image at different times; and
wherein the method further comprises:
identifying movement of the fiducials based on different positions of the fiducials at different times; and
controlling treatment based on the movement.

19. A treatment system comprising:
a treatment couch for holding a patient;
fiducials associated with the patient;
a first imaging system located at an imaging position to capture a first image of the fiducials and of an irradiation target while the patient is on the treatment couch, the first imaging system being in a treatment room where treatment using a particle therapy system is to be performed;
a mechanism to move the treatment couch while the patient is on the treatment couch from the imaging position toward a treatment position at which the treatment using the particle therapy system is to be performed, the treatment position being different from the imaging position and being in the treatment room;
a second imaging system to capture a second image of the fiducials in the treatment room following movement of the treatment couch toward the treatment position and while the patient is on the treatment couch; and
a computer system programmed to align locations of the fiducials in the second image to locations in the treatment room, to align locations of fiducials in the first image to the locations in the treatment room, and to determine a location of the irradiation target relative to the particle therapy system based on the locations of the fiducials in the treatment room and based on the first image
wherein the mechanism to move the treatment couch is controllable to move the treatment couch based on the location of the irradiation target so that the irradiation target is in the treatment position;
wherein the patient remains on the treatment couch during capturing the first image, through moving the treatment couch toward the treatment position, and during capturing the second image.

20. The system of claim 19, wherein the first imaging system is configured to capture internal images of the patient and of the fiducials; and
wherein the second imaging system is configured to capture external images of the fiducials.

21. The system of claim 19, wherein the first imaging system comprises one or more of the following: an X-ray device to capture a radiograph image, a computed tomography (CT) device to capture a CT image, a magnetic resonance imaging (MRI) device to capture an MM image, a positron emission tomography (PET) device to capture a PET image, a video surface imaging device, or a SPECT/CT device.

22. The system of claim 19, further comprising:
the particle therapy system comprising a particle accelerator system to treat the patient at the treatment position;
wherein treating the patient comprising irradiating the patient with protons output by the particle accelerator.

23. The system of claim 22, wherein the particle therapy system has an isocenter, the isocenter comprising the treatment position.

24. The system of claim 19, wherein the location of the irradiation target relative to the particle therapy system is determined based on a reference coordinate system of the treatment room.

25. The system of claim 24, wherein the particle therapy system has an isocenter; and
wherein moving the treatment couch into the treatment position comprises moving the treatment couch so that the location of the irradiation target corresponds to a location of the isocenter.

26. The system of claim 24, wherein the reference coordinate system is part of a real world space that includes the treatment system.

27. The system of claim 19, further comprising:
restraints to secure the patient to the treatment couch.

28. The system of claim 19, wherein the mechanism comprises a robotic mechanism, the robotic mechanism being configured to automatically move the treatment couch from the imaging position to the treatment position while the patient remains on the treatment couch.

29. The system of claim 19, wherein the mechanism is controllable to manually move the treatment couch while the patient remains on the treatment couch.

30. The system of claim 19, wherein the fiducials are arranged on the patient.

31. The system of claim 19, wherein the fiducials comprise anatomical landmarks on the patient.

32. The system of claim 19, further comprising a frame over at least part of the patient, the fiducials being secured to the frame.

33. The system of claim 19, wherein the first image comprises a three-dimensional (3D) image or a two-dimensional (2D) image.

34. The system of claim 19, wherein the computer system is programmed to perform operations comprising:
determining an orientation of the irradiation target based on locations of the fiducials in the treatment room and in the first image; and
orienting the treatment based on the orientation of the irradiation target.

35. The system of claim 19, wherein the computer system is programmed to perform operations comprising:
tracking movement of the fiducials over time; and
controlling movement of the treatment couch based on movement of the fiducials.

36. The system of claim 19, wherein the computer system is programmed to perform operations comprising:
tracking movement of the fiducials over time; and
controlling treatment based on movement of the fiducials.

37. The system of claim 19, wherein capturing the first image comprises capturing the first image at different times; and
wherein the computer system is programmed to perform operations comprising:

identifying movement of the fiducials based on different positions of the fiducials at different times; and
controlling treatment based on the movement.

\* \* \* \* \*